United States Patent [19]

Hayward et al.

[11] Patent Number: 5,574,828

[45] Date of Patent: Nov. 12, 1996

[54] EXPERT SYSTEM FOR GENERATING GUIDELINE-BASED INFORMATION TOOLS

[75] Inventors: Robert S. A. Hayward, Hamilton, Canada; Michael F. Roizen; David Summerell, both of Chicago, Ill.; Martin Rom, Bloomfield Hills, Mich.

[73] Assignee: TMRC, Bloomfield Hills, Mich.

[21] Appl. No.: 234,982

[22] Filed: Apr. 28, 1994

[51] Int. Cl.$^6$ .............................. G06F 17/00; G06F 15/00
[52] U.S. Cl. .................................. 395/50; 395/75; 395/76; 364/413.02
[58] Field of Search .................................. 395/50, 75, 76; 364/413.02

[56] References Cited

U.S. PATENT DOCUMENTS

| | | | |
|---|---|---|---|
| 4,622,013 | 11/1986 | Cerchio | 434/118 |
| 4,730,259 | 3/1988 | Gallant | 364/513 |
| 4,733,354 | 3/1988 | Potter et al. | 364/415 |
| 4,839,822 | 6/1989 | Dormond et al. | 364/513 |
| 4,872,122 | 10/1989 | Altschuler et al. | 364/554 |
| 4,945,476 | 7/1990 | Bodick et al. | 364/413.02 |
| 5,005,143 | 4/1991 | Altschuler et al. | 364/554 |
| 5,023,785 | 6/1991 | Adrion et al. | 364/413.08 |
| 5,025,374 | 6/1991 | Roizen et al. | 364/413.02 |
| 5,208,898 | 5/1993 | Funabashi et al. | 395/50 |
| 5,255,187 | 10/1993 | Sorenson | 364/413.02 |
| 5,347,614 | 9/1994 | Yamada et al. | 395/75 |

Primary Examiner—Raymond J. Bayerl
Assistant Examiner—A. Katbab
Attorney, Agent, or Firm—Jon L. Roberts; Thomas M. Champagne; Roberts & Associates

[57] ABSTRACT

A system utilizing a software program used to write other software application programs for the implementation of guideline applications for use in situations where a qualification decision or next course of action determination must be made. The system uses questions with limited choice answers. Data provided in answer to the questions causes a second program application to be automatically generated based on the answers. The second application then elicits responses in an interactive manner. Qualification decisions and courses of action are suggested as an output of the second application. Means are provided for evaluating the reliability of the suggestions based on consistency of answers and fatigue of the user. Means are also provided for editing either application program.

9 Claims, 94 Drawing Sheets

FIGURE 14

| 0.0 | Not exists |

101 Have you EVER had any pain or discomfort in your chest?

| 0.5 | Not exists |

102 Do you get any pain or discomfort in your chest on effort or when climbing stairs?

| 143.0 | Not exists |

129 Did you have any trouble reading the HealthQuiz questions?

| 145.0 | Not exists |

149 Were you likely to be as truthful with the HealthQuiz as you would be with your doctor?

| 20.0 | Not exists |

150 Have your relatives EVER had anesthesia?

| 21.0 | Not exists |

151 Did any of your relatives EVER have a problem with anesthesia?

| 103.0 | Not exists |

152 Did the pneumonia result in any permanent lung damage or result in surgery?

| 67.0 | Not exists |

153 Are you allergic to Penicillin?

FIGURE 15

Question
Have you EVER given blood before?

Comments

Author
Roizen, Mike

Citation
No citation

Copyright

Keyword
Transfusion risks;

Last revised: April 12, 1994

Index
Item
Order
Filter

Question number 5903

Status: Not exists

Category: Transfusion

Sub-category: History

Question type: 2

FIGURE 18

| ## | Score Name and Interpretation | Abbrev. | >High | <Low |
|---|---|---|---|---|
| 3 | Activities of Daily Living<br>5 standard ADL questions - 10 point max | ADL | 5 | 3 |

Risk Score

| ## | Question Text | Add to Score on Answer | | | | |
|---|---|---|---|---|---|---|
| | | 1 | 2 | 3 | 4 | 5 |
| 1409: | Are you able to eat without help? | 0 | 2 | 1 | 0 | |
| 1408: | Are you usually able to control your bladder and bowels? | 0 | 2 | 1 | 0 | |
| 1407: | Are you able to move in and out of a bed or chair without help? | 0 | 2 | 1 | 0 | |
| 1406: | Are you able to take a bath or shower without help? | 0 | 2 | 1 | 0 | |
| 1405: | Are you able to dress yourself without help? | 0 | 2 | 1 | 0 | |

Risk Factor

FIGURE 20

| ## | Score Name and Interpretation | Abbrev. | >High | <Low |
|---|---|---|---|---|
| | Patient Fatigue Index<br>(High >5, Moderate 2-5, Low <2) | FAT | 5 | 2 |

Fatigue Score

| ## | Question Text | Add to Score on Answer | 1 | 2 | 3 | 4 | 5 |
|---|---|---|---|---|---|---|---|
| 1465: | You have not finished the HEALTHQUIZ. You can skip any of the sex questions by pressing the NOT SURE button. Are you sure you want to quit? | | 1 | 0 | 0 | 0 | 0 |
| 1464: | You have not finished the HEALTHQUIZ. Are you sure you want to quit? | | 1 | 0 | 0 | 0 | 0 |
| 1463: | You have not finished the HEALTHQUIZ. Are you sure you want to quit? | | 1 | 0 | 0 | 0 | 0 |
| 1462: | You have not finished the HEALTHQUIZ. The next questions are important. Are you sure you want to quit? | | 1 | 0 | 0 | 0 | 0 |
| 1461: | You have not finished the HEALTHQUIZ. Are you sure you want to quit? | | 1 | 0 | 0 | 0 | 0 |

Fatigue Factor

FIGURE 22

```
1
2    <A> year old <sex>                >|     ID #         <PID     >
3                                             BIRTHDATE:   <DOB     >
4                                             DATE:        <HDATE   >
5    PATIENT NAME: _____
6
7    CLINICIAN NAME: _____
8
9        Thank you for completing the HealthQuiz. A summary of your responses has been given to your
10   doctor. Listed below are some (but not necessarily all of the items) that may be of particular concern to
11   your health. Be aware that even the best computer programs can make mistakes so ask your physician or
12   nurse practitioner if you have any questions.
13
14       Please read through these issues and get the advice of your physician or nurse practitioner.
15
16
17   <F9                                                                                              >
18   _____
```

Guideline Application Program - Guidelines Listing       FIGURE 82

Application:         From item: 0 to 0         Index: Intervention
Category: ALL        Subcategory:   all        Ordered by: PRIORD Detailed Guidelines Listing Clinical: Blood Pressure Measurement U.S. Preventive Services Task Force General: MF 18+ every 2 y and at every visit for other reasons
Selective: MF 18+ every 1 y if diastolic BP 85-89 mm Hg. p23
Guideline 832; Published 1989;
(Entered Jan 01 1991; Updated Apr 05 1994; by Hayward, Robert)

Oboler and LaForce

General: MF 20+ every 2 y
Guideline 1120; Published 1989;
(Entered Jan 01 1991; Updated Apr 05 1994; by Hayward, Robert)

Institute of Medicine

General: MF 18+ every 5y
Guideline 1330; Published 1978;
(Entered Jan 01 1991; Updated Apr 05 1994; by Hayward, Robert)

Paul Frame, et. al.

General: MF 18+ every 2y
Guideline 1058; Published 1986;
(Entered Jan 01 1991; Updated Apr 05 1994; by Hayward, Robert)

Joint National Commission and American Heart Association

General: MF 18+ every 2 y
Selective: MF 18+ every 1 y if diastolic BP 80-89 mm Hg; Measure BP more
frequently if diastolic BP>89 mm Hg
Guideline 1144; Published 1988;
(Entered Jan 01 1991; Updated Apr 05 1994; by Hayward, Robert)

Canadian Task Force on the Periodic Health Examination

General: [A] MF 25-64 at least every 5y and at every visit for other reasons
[A] MF 65+ every 2y
Selective: No recommendation
Guideline 552; Published 1984;
(Entered Jan 01 1991; Updated Apr 05 1994; by Hayward, Robert)

Guideline Application Program - Guidelines Listing

| Application: | From item: 0 to 0 | Index: Intervention |
|---|---|---|
| Category: ALL | Subcategory: all | Ordered by: PRIORD |

Detailed Guidelines Listing

American College of Physicians

General: MF 18+ every 1-2y and at every visit for other reasons
Selective: MF 18+ every 1y if diastolic BP 85-89 mmHg.
  MF 18+ at least every 1y; If 1 or more of: prior hypertension, DM, known CAD or other risk factors for cardiovascular disease, moderate or extreme obesity, black race, history of hypertension in parents or siblings
Guideline 1284; Published 1990;
(Entered Jan 01 1991; Updated Apr 05 1994; by Hayward, Robert)

Algorithms pertaining to: Blood pressure measurement

RULE Number: 1362.00
Systolic BP(mmHg) IS LESS THAN 10, OR
Diastolic BP(mmHg) IS LESS THAN 10.

RULE Number: 1364.00
Systolic BP (mmHg) IS LESS THAN 151, AND
Diastolic BP (mmHg) IS MORE THAN 84, AND
Diastolic BP(mmHg) IS LESS THAN 91

RULE Number: 1365.00
Systolic BP (mmHg) IS MORE THAN 150, OR
Diastolic BP (mmHg) IS MORE THAN 90.

Intervention: Blood pressure measurement

FIGURE 83

Guideline Application Program - Risk Score Listing

| | | |
|---|---|---|
| Application: | From item: 0 to 0 | Ordered by: QNUMBER |
| Category: ALL | Subcategory: ALL | |

| Question | Risk Score Type | Response Values |
|---|---|---|

Cardiovascular

Score #1      High > 5, Moderate = 2-5, Low <2

| Question | | | | | |
|---|---|---|---|---|---|
| 10: Sex is Male. | True<br>1 | False<br>0 | NA<br>0 | NA<br>0 | NA<br>0 |
| 1493: Do you smoke more than 20 cigarettes, pipes, or cigars a DAY? | Yes<br>1 | No<br>0 | Unsure<br>0 | NA<br>0 | NA |
| 1341: Have you EVER been told that you have had a stroke? | Yes<br>1 | No<br>0 | Unsure<br>0 | NA<br>0 | NA |
| 1338: Have you EVER been told that you have angina, or narrowing of the blood vessels of the heart? | Yes<br>2 | No<br>0 | Unsure<br>0 | NA<br>0 | NA |
| 1203: Have you ever had menstrual periods (regular or irregular) AFTER you were 40 years old? | Yes<br>0 | No<br>1 | Unsure<br>0 | NA<br>0 | NA |
| 1170: Have you quit smoking for at least the last YEAR? | Yes<br>1 | No<br>2 | Unsure<br>0 | NA<br>0 | NA |
| 1142: Have you EVER been told you have diabetes? | Yes<br>2 | No<br>0 | Unsure<br>0 | NA<br>0 | NA |
| 1124: Do you still smoke NOW? | Yes<br>2 | No<br>0 | Unsure<br>0 | NA<br>0 | NA |
| 1101: Did your mother, father, brother, sister or any of your children have a heart attack, stroke, or heart surgery before they were 60 years old? | Yes<br>1 | No<br>0 | Unsure<br>0 | NA<br>0 | NA |

FIGURE 84

Guideline Application Program - Risk Score Listing

| Application: | From item: 0 to 0 | Ordered by: QNUMBER |
|---|---|---|
| Category: ALL | Subcategory: ALL | |

| Question Number | Risk Score Type | Response Values |
|---|---|---|

| Question Number | | | | | |
|---|---|---|---|---|---|
| 1082: In the last YEAR, have you had angina, heart pains, or chest heaviness? | True<br>6 | False<br>0 | NA<br>0 | NA<br>0 | NA |
| 1077: Do you usually climb 10 or more flights of stairs or walk for more than 1 hour during the DAY? | Yes<br>0 | No<br>1 | Unsure<br>0 | NA<br>0 | NA |
| 1062: Have you EVER been told that you have a high cholesterol level? | Yes<br>2 | No<br>0 | Unsure<br>0 | NA<br>0 | NA |
| 1061: Have you EVER been told that you have high blood pressure? | Yes<br>1 | No<br>0 | Unsure<br>0 | NA<br>0 | NA |
| 1060: Have you EVER been told to diet, or exercise, or take drugs because of high blood pressure? | Yes<br>1 | No<br>0 | Unsure<br>0 | NA<br>0 | NA |
| 1059: Have you EVER been told that you have had a heart attack? | Yes<br>6 | No<br>0 | Unsure<br>0 | NA<br>0 | NA |

FIGURE 85

Guideline Application Program - Risk Score Listing

| Application: | From item: 1631 to 1641 | Index: RULENUM |
|---|---|---|
| Category: ALL | Subcategory: ALL | Ordered by: GROUP TITLE |

| Title | Rule Number | Group 1 | Group 2 | Written | Last Updated |
|---|---|---|---|---|---|
|  | 1638 | 1.06 | 1 | Apr/12/1994 | Apr/12/1994 |
| Note: History of easy or severe sunburn | | | | | |
|  | 1639 | 1.06 | 1 | Apr/13/1994 | Apr/13/1994 |
| Note: History of skin cancer | | | | | |
|  | 1640 | 1.08 | 1 | Apr/13/1994 | Apr/13/1994 |
| Note: Past anti-TB-therapy, possibly incomplete | | | | | |
| affect | 1637 | 1.09 | 1 | Apr/12/1994 | Apr/12/1994 |
| Note: Past suicide attempt | | | | | |
| pregnancy | 1636 | 1.09 | 1 | Apr/12/1994 | Apr/12/1994 |
| Note: Planning pregnancy in next 3 months | | | | | |
|  | 1631 | 1.11 | 1 | Apr/13/1994 | Apr/13/1994 |
| Note: Living partner has problem drinking | | | | | |
|  | 1632 | 1.17 | 1 | Apr/13/1994 | Apr/13/1994 |
| Note: Chronic liver/kidney disorder | | | | | |
|  | 1641 | 1.18 | 1 | Apr/13/1994 | Apr/13/1994 |
| Note: Last urinalysis, <1 yr. | | | | | |

End of Risk Statement Listing

FIGURE 86

Guideline Application Program - Algorithms Listing

| Application: | From item: 1365 to 1375 | Index: RULENUM |
|---|---|---|
| Category: ALL | Subcategory: ALL | Ordered by: RULENUM |

| Rule Number | Written | Last Updated |
|---|---|---|
| 1365 | JAN/01/1991 | Apr/04/1994 |

Systolic BP (mmHg) IS MORE THAN 150, OR
Diastolic BP (mmHg) IS MORE THAN 90.

| 1367 | Jan/01/1991 | Apr/12/1994 |
|---|---|---|

Q1189: Have you EVER been told to take antibiotics before any dental work? IS Yes, OR
Q1141: Have you EVER been told that you have mitral valve prolapse? IS Yes, OR
Q1140: Have you EVER had a heart murmur, rheumatic fever, or a damaged heart valve? IS Yes, OR
Q1139: In the last YEAR have you had irregular heartbeats or palpitations? IS Yes, OR
Q1506: In the last YEAR have you fainted, had a drop attack, or lost consciousness? IS Yes.

| 1368 | Jan/01/1991 | Apr/11/1994 |
|---|---|---|

Age (years) IS MORE THAN 39, AND
Q1341: Have you EVER been told that you have had a stroke? IS Yes, OR
Q1271: In the last YEAR have you been paralyzed or lost control of any part of your body? IS Yes, OR
Q1506: In the last YEAR have you fainted, had a drop attack, or lost consciousness? IS Yes, OR
Cardiovascular score IS MORE THAN 2.

| 1369 | Jan/01/1991 | Apr/09/1994 |
|---|---|---|

Age (years) IS LESS THAN 71, AND
Q1062: Have you EVER been told that you have a high cholesterol level? IS NOT Yes, AND
Q1069: Has your mother, father, brother, sister, or any of your children EVER had high cholesterol: IS NOT Yes, AND
Q1051: In the last 5 YEARS, has your cholesterol been measured? IS NOT Yes, AND
Q1050: In the last YEAR, has your cholesterol been measured? IS NOT Yes, AND
Cardiovascular score IS LESS THAN 2.

| 1370 | Jan/01/1991 | Apr/04/1994 |
|---|---|---|

Age (years) IS LESS THAN 71, AND
Q1069: Has your mother, father, brother, sister, or any of your children EVER had high cholesterol? IS Yes, AND
Q1050: In the last YEAR, has your cholesterol been measured? IS NOT Yes, AND
Q1051: In the last 5 YEARS, has your cholesterol been measured? IS NOT Yes, AND
Cardiovascular score IS LESS THAN 2

| 1371 | Jan/01/1991 | Apr/09/1994 |
|---|---|---|

Age (years) IS LESS THAN 71, AND
Q1050: In the last YEAR, has your cholesterol been measured? IS NOT Yes, AND
Cardiovascular score IS MORE THAN 1, OR
Body Mass Index IS MORE THAN 30

| 1372 | Jan/01/1991 | Apr/02/1994 |
|---|---|---|

Q1048: In your job, are you directly responsible for the safety of others (such as a bus driver or airline pilot)? IS Yes, AND
Q1053: Have you EVER had an EKG (electrocardiogram, or heart tracing)? IS NOT Yes.

| 1373 | Jan/01/1991 | Apr/04/1994 |
|---|---|---|

Age (years) IS MORE THAN 39, AND
Q1053: Have you EVER had an EKG (electrocardiogram, or heart tracing)? IS NOT Yes, AND
Cardiovascular score IS MORE THAN 5, AND
Q1048: In your job, are you directly responsible for the safety of others (such as a bus driver or airline pilot)? IS NOT Yes.

FIGURE 87

Guideline Application Program - Algorithms Listing

| Application: From item: 1365 to 1375 Index: RULENUM |
|---|
| Category: ALL Subcategory: ALL Ordered by: RULENUM |
| Rule Number　　　　Written　　　　　　　Last Updated |

1374　　　　　　　Jan/01/1991　　　　　　　Apr/04/1994

Age (years) IS MORE THAN 39, AND
Q1139: In the last YEAR have you had irregular heart beats or palpitations? IS Yes, OR
Heart Rate (bpm) IS MORE THAN 99, AND
Q1053: Have you EVER had an EKG (electrocardiogram, or heart tracing)? IS NOT Yes, AND
Q1048: In your job, are you directly responsible for the safety of others (such as a bus driver or airline pilot)? IS NOT Yes, AND
Cardiovascular score IS LESS THAN 6.

1375　　　　　　　Jan/01/1991　　　　　　　Apr/04/1994

Age (years) IS MORE THAN 39, AND
Sex IS Male, AND
Q1106: Do you plan to start a program of regular exercise in the next MONTH? IS Yes, AND
Q1232: Have you EVER had an exercise-stress test or treadmill test for your heart? IS NOT Yes.

End of Rules Report

FIGURE 88

Guideline Application Program - Algorithms Listing

| Application: | From item: 1438 to 1500 | Index: RULENUM |
|---|---|---|
| Category: ALL | Subcategory: ALL | Ordered by: RULENUM |

| Rule Number | Written | Last Updated |
|---|---|---|
| 1438 | JAN/01/1991 | Apr/10/1994 |

Age (years) IS LESS THAN 65, AND
Q1433: In the last 10 YEARS, have you had a shot or vaccine to prevent pneumonia? IS NOT Yes, AND
Q1194: Do you have sickle cell anemia (NOT sickle cell train)? IS Yes, OR
Q1142: Have you EVER been told you have diabetes? IS Yes, OR
Q1576: Do you have a continuing or chronic kidney or liver disease? IS Yes, OR
Q1155: Do you become short of breath after climbing one flight of stairs or after walking a short distance? IS yes, OR
Q1505: Has your spleen been damaged or removed? IS Yes, OR
CAGE Alcohol score IS MORE THAN 3.

| 1439 | Jan/01/1991 | Apr/04/1994 |
|---|---|---|

Age (years) IS MORE THAN 64, AND
Q1433: In the last 10 YEARS, have you had a shot or vaccine to prevent pneumonia? IS NOT Yes.

| 1440 | Jan/01/1991 | Apr/04/1994 |
|---|---|---|

Age (years) IS LESS THAN 35, AND
Q1425: Have you EVER had measles or a vaccine for measles? IS NOT Yes.

| 1441 | Jan/01/1991 | Apr/11/1994 |
|---|---|---|

Age (years) IS LESS THAN 46, AND
Q1577: Do you plan to become pregnant in the next 3 MONTHS? IS No, AND
Q1283: Have you EVER had Rubella (German Measles) or a vaccine for Rubella? IS NOT Yes, AND
Q1128: Do you have any reason to believe you may be pregnant now? IS No, AND
Q1348: Were both of your ovaries (2) completely removed? IS NOT Yes.

| 1442 | Jan/01/1991 | Apr/12/1994 |
|---|---|---|

Q1209: In the last 10 YEARS, have you had a tetanus vaccine or booster shot? IS No, OR
Q1209: In the last 10 YEARS, have you had a tetanus vaccine or booster shot? IS Unsure.

| 1443 | Jan/01/1991 | Apr/12/1994 |
|---|---|---|

Q1377: Do any children under 10 years old live with you? IS Yes.

| 1444 | Jan/01/1991 | Apr/04/1994 |
|---|---|---|

Q1383: Do you care for an elderly or infirm person in your own home: IS Yes, OR
Age (years) IS MORE THAN 74.

| 1445 | Jan/01/1991 | Apr/12/1994 |
|---|---|---|

Age (years) IS LESS THAN 40, AND
Q1523: Is there a handgun in your car or home? IS Yes.

| 1446 | Jan/01/1991 | Apr/13/1994 |
|---|---|---|

Q1210: Do you always wear a seatbelt? IS No.

FIGURE 89

Guideline Application Program - Algorithms Listing

| Application: | From item: 1447 to 1451 | Index: RULENUM |
|---|---|---|
| Category: ALL | Subcategory: ALL | Ordered by: RULENUM |

| Rule Number | Written | Last Updated |
|---|---|---|
| 1447 | Jan/01/1991 | Apr/04/1994 |

Q1468: Do you always wear a helmet while riding? IS No.

| 1448 | Jan/01/1991 | Apr/04/1994 |
|---|---|---|

Q1300: In the last YEAR, has the smoke detector been checked to see if it is working? IS No, OR Q1299: Is there a smoke detector in the house or apartment where you live? IS NOT Yes.

| 1449 | Jan/01/1991 | Apr/13/1994 |
|---|---|---|

Age (years) IS LESS THAN 65, AND
Sexually Transmitted Diseases score IS MORE THAN 2.

| 1450 | Jan/01/1991 | Apr/12/1994 |
|---|---|---|

Age (years) IS LESS THAN 46, AND

Q1128: Do you have any reason to believe you may be pregnant now? IS No, AND

Q1357: In the last YEAR have you had sexual relations (intercourse, oral sex, anal sex) with anyone? IS NOT No, AND Q1348: Were both of your ovaries (2) completely removed? IS NOT Yes, AND Q1577: Do you plan to become pregnant in the next 3 MONTHS? IS NOT Yes.

| 1451 | Jan/01/1991 | Apr/13/1994 |
|---|---|---|

Age (years) IS LESS THAN 65, AND

Sexually Transmitted Diseases score IS MORE THAN 4, OR

Q1471: Have you ever used a needle to take a street drug? IS Yes, OR

Q1388: Have you EVER had sexual relations with someone who may use a needle to take street drugs? IS Yes, OR Q1390: In the last 10 YEARS, have you had sexual relations with a man who may be homosexual or bisexual? IS Yes.

End of Rules Report

FIGURE 90

Guideline Application Program - Algorithms Listing

| Application: | From item: 1631 to 1641 | Index: RULENUM |
|---|---|---|
| Category: ALL | Subcategory: ALL | Ordered by: RULENUM |

| Rule Number | Written | Last Updated |
|---|---|---|
| 1631 | Apr/13/1994 | Apr/13/1994 |
| Q17022: Does your spouse or living partner have a drinking problem? IS Yes. | | |
| 1632 | Apr/11/1994 | Apr/11/1994 |
| Q1576: Do you have a continuing or chronic kidney or liver disease? IS Yes. | | |
| 1633 | | Apr/12/1994 |
| Q1229: Have you EVER been told you have a thyroid problem? IS Yes. | | |
| 1634 | | Apr/12/1994 |
| Q1345: In the last 2 YEARS has your eyesight changed? IS Yes. | | |
| 1635 | | Apr/12/1994 |
| Cardiovascular score IS MORE THAN 4. | | |
| 1636 | Apr/12/1994 | Apr/12/1994 |
| Q1577: Do you plan to become pregnant in the next 3 MONTHS? IS Yes. | | |
| 1637 | Apr/12/1994 | Apr/12/1994 |
| Q17006: Have you EVER attempted suicide? IS Yes. | | |
| 1638 | Apr/12/1994 | Apr/12/1994 |
| Q17013: Have you EVER had a severe sunburn that has caused blisters? IS Yes, OR Q17012: Do you tend to burn more than tan when you are in the sun? IS Yes. | | |
| 1639 | Apr/13/1994 | Apr/13/1994 |
| Q1574: Have you EVER had a skin tumor or skin cancer? IS Yes. | | |
| 1640 | Apr/13/1994 | Apr/13/1994 |
| Q17019: Did you complete the full course of INH (isoniazid) therapy to prevent tuberculosis? IS NOT Yes. | | |

FIGURE 91

Guideline Application Program - Algorithms Listing

| Application: | From item: 1631 to 1641 | Index: RULENUM |
| Category: ALL | Subcategory: ALL | Ordered by: RULENUM |
| Rule Number | Written | Last Updated |

| 1641 | Apr/13/1994 | Apr/13/1994 |

| Q1575: In the last YEAR, has your urine been tested by a doctor? IS Yes. |

End of Rules Report

FIGURE 92

Guideline Application Program - Short Patient Note Listing

| Application: | From item: 1365 to 1375 | Index: RULENUM |
|---|---|---|
| Category: ALL | Subcategory: ALL | Ordered by: PRIORD |

| Title | Rule Number | Order Number | Written | Last Updated |
|---|---|---|---|---|
| High Blood Pressure: | 1365 | 1 | Jan/01/1991 | Apr/14/1994 |

Note: Your blood pressure was higher than normal today (over 150/90). Please ask your doctor about rechecking your blood pressure and what to do if it remains high. Uncontrolled high blood pressure can increase your chance of having a heart attack or stroke.

| Cholesterol: | 1369 | 2 | Jan/01/1991 | Apr/14/1994 |

Note: Although your answers to the HealthQuiz do not suggest a higher than normal risk of future heart disease, you should have your blood cholesterol checked every 5 years. Untreated high cholesterol can increase your chance of having a heart attack.

| Cholesterol: | 1370 | 3 | Jan/01/1991 | Mar/21/1994 |

Note: High cholesterol can lead to heart attacks. The Surgeon General has recommended that all Americans over 18 years of age have their cholesterol measured at least once every 5 years. People like you with a family history of high cholesterol levels may need their cholesterol checked more often. You should know whether your cholesterol is high and what you should do about it.

| Cholesterol: | 1371 | 4 | Jan/01/1991 | Mar/21/1994 |

Note: Your answers indicate risk factors for heart problems but you have not had your cholesterol checked. You should have your cholesterol checked more frequently than the recommended once every 5 years because high cholesterol may lead to heart attacks. Talk with your doctor, arrange to have your cholesterol checked and find out what to do if your cholesterol is high.

| Exercise: | 1375 | 5 | Jan/01/1991 | Apr/14/1994 |

Note: You indicate a desire to begin regular exercise. It is recommended that you could benefit from an exercise stress test before you begin. Talk with your doctor about an exercise stress test. A regular exercise program can be very beneficial to your health.

End of Short Patient Note Listing

FIGURE 93

Guideline Application Program - Suggestions Listing

| Application: | From item: 1438 to 1500 | Index: RULENUM |
|---|---|---|
| Category: ALL | Subcategory: ALL | Ordered by: ROUP1.PRIOR |

| Rule Number | Order Number | Written | Last Updated |
|---|---|---|---|
| 1438 | 79 | Jan/01/1991 | Apr/05/1994 |

Title:
Note: Pneumonia immunization

Footnote: Pneumococcal vaccine is indicated for persons at high risk by virtue of sickle cell disease, alcoholism, respiratory compromise, diabetes or chronic disease.

| 1439 | 80 | Jan/01/1991 | Apr/05/1994 |

Title:
Note: Pneumonia immunization

Footnote: Immunization against pneumonia is indicated for persons age 65+.

| 1440 | 81 | Jan/01/1991 | Apr/11/1994 |

Title:
Note: Measles immunization

Footnote: Immunization against measles in adulthood is indicated for persons born after 1956 who cannot document a history of natural disease or immunization.

| 1441 | 82 | Jan/01/1991 | Apr/11/1994 |

Title:
Note: Rubella immunization

Footnote: Rubella immunization may be indicated for women of childbearing age who have no prior immunization or native disease and who are not pregnant or planning pregnancy in the next 3 months.

| 1442 | 83 | Jan/01/1991 | Apr/11/1994 |

Title:
Note: Tetanus toxoid booster

Footnote: All adults should receive a tetanus toxoid booster every 10 years. This patient's response indicates no certain tetanus toxoid administered in the last 10 years.

| 1443 | 84 | Jan/01/1991 | Apr/05/1994 |

Title:
Note: Prevention of childhood injuries

Footnote: Advice regarding hot water temperature, chemicals, medications, firearm safety, and other household dangers may be appropriate; this patient reports children in the home.

| 1444 | 85 | Jan/01/1991 | Apr/05/1994 |

Title:
Note: Prevention of falls in the elderly

Footnote: Advice regarding prevention of falls and injury to the elderly or dependent adults may be appropriate; this patient reports a dependent adult in the home or age 75+.

FIGURE 94

Guideline Application Program - Suggestions Listing

| Application: | From item: 1438 to 1500 | Index: RULENUM |
|---|---|---|
| Category: ALL | Subcategory: ALL | Ordered by: ROUP1.PRIOR |

| Rule Number | Order Number | Written | Last Updated |
|---|---|---|---|
| 1445 | 86 | Jan/01/1991 | Apr/05/1994 |

Title:
Note: Firearm injury prevention

Footnote: Advice regarding the high morbidity/mortality associated with handgun availability, and violent behavior may be appropriate; this patient is in a high risk age group for domestic and public violence.

| 1446 | 87 | Jan/01/1991 | Apr/13/1994 |

Title:
Note: Seat belt use

Footnote: Advice about regular use of seat belts when driving can help reduce the high morbidity and mortality rate associated with automobile use.

| 1447 | 88 | Jan/01/1991 | Apr/12/1994 |

Title:
Note: Helmet use for bicycles, motorbikes

Footnote: Advice about the regular use of helmets while driving a motorcycle or bicycle can help reduce roadside morbidity and mortality.

| 1448 | 89 | Jan/01/1991 | Apr/05/1994 |

Title:
Note: Smoke detector use and maintenance

Footnote: Advice about the installation and regular checking of smoke detectors and the dangers of smoking near beds or upholstery can help reduce morbidity and mortality associated with household fires.

| 1449 | 90 | Jan/01/1991 | Apr/05/1994 |

Title:
Note: Prevention of STDs

Footnote: Advice regarding STD transmission, partner selection, anal intercourse, condom use is particularly important for persons reporting high risk sexual behaviors.

| 1450 | 91 | Jan/01/1991 | Apr/05/1994 |

Title:
Note: Prevention of unintended pregnancy

Footnote: Inquiry regarding contraceptive use and pregnancy planning is particularly important for persons reporting sexual activity and no desire to become pregnant.

| 1451 | 92 | Jan/01/1991 | Apr/05/1994 |

Title:
Note: Prevention of HIV transmission

Footnote: Teaching prevention of HIV transmission is most important for persons reporting high risk sexual behaviors, suspect transfusions, IV drug use, sexual contact with IV drug users, or interest.

FIGURE 95

EXPERT SYSTEM FOR GENERATING GUIDELINE-BASED INFORMATION TOOLS

FIELD OF THE INVENTION

The present invention relates generally to an expert system for providing a response based on inputs processed according to specific guidelines. In particular, the present invention relates to a system including a computer application program which accepts input data based on guidelines of various types and generates a second interactive application program known as a Guideline Application Program ("GAP") based on the input data and on the guidelines. The GAP is used to elicit additional data from an end user, and processes the additional data to generate an appropriate response such as a course of action recommendation or a qualification decision.

BACKGROUND OF THE INVENTION

Information management is an overwhelming task faced by people in many professions. In particular, people who must evaluate data in order to make qualification decisions or to plan a course of action must make decisions based on a great deal of data. In many cases, the data must be evaluated according to certain guidelines. While guidelines are followed during the decision making process to the extent possible to avoid missing details that aid in making the decision, subjective judgements must still be made regarding the parameters of the situation due to the large amounts of data that must be processed and the great number of criteria (dictated by the guidelines) involved in many decisions. Further, not all available data is pertinent to the decision, and much time and effort is wasted by not putting aside this irrelevant data early in the decision making process.

Guidelines used in processing such data can be a valuable aid in making a qualification decision or in planning a course of action. For example, in the last decade, clinical practice guidelines have proliferated widely as professional organizations, academic and private institutions, insurers, hospitals, and governments have developed them in the hope that they will facilitate the development of more consistent, effective, and efficient medical practices. Guidelines that are based upon sound· scientific evidence, and a trustworthy process for judging the value of alternative practices, can be a valuable aid to clinical decision making by health care practitioners.

Good guidelines, however, do not necessarily translate into useable tools. Guidelines have become increasingly complex, and the amount of data processed has grown to overwhelming proportions. For example, instead of using simple checklists to trigger standard medical interventions for all patients of a certain age and gender, health care practitioners must consider a wide range of health risks, the presence of which can mandate changes in the content, timing, and frequency of appropriate medical interventions. To be most effective, decision makers in all fields need practical strategies for applying guidelines in daily practice. They need new tools to facilitate data assessment, documentation of determinations, and individualized implementation of practice guidelines in an objective manner. A system that could actually create a useful tool, based on given guidelines, to aid in such determinations or implementations would therefore be highly desirable.

Systems have previously been designed which process data in order to qualify plan a course of action regarding individuals. For example, U.S. Pat. No. 4,622,013 to Cerchio discloses an interactive software training system. This is an early diagnostic expert system which branches to different paths during a training exercise based on inputs from the user.

U.S. Pat. No. 5,005,143 to Altschuler discloses a rule based computer system for selecting from a set of output actions for combinatory situations defined by a plurality of input parameters. The system employs a decision tree structure that is developed by a particular user. Random values of the input parameters are generated and the random values are biased by a function of preceding responses. The steps are repeated until a sufficient number of responses having a predetermined statistical significance are determined for each node of the decision tree. After this point, the user's response to given input parameters can be predicted based on previous user selections as manifested in the node decisions. U.S. Pat. No. 4,733,354 to Potter et al. also discloses a system for automated medical diagnosis using decision tree analysis. U.S. Pat. No. 4,730,259 to Gallant discloses a similar expert system that will follow an approximate course from input to output if a path is not defined for a particular set of inputs.

U.S. Pat. No. 5,208,898 to Funabashi et al. discloses a knowledge processing system employing a method by which primary events for which no determining means is provided are operated upon by knowledge represented as rules referring to the primary events for estimating or predicting the events by use of the same knowledge so as to enable the knowledge to be adapted to an inference. Events as knowledge representing an object are combined with rules as knowledge so as to establish a relation of combination. A grade representing a degree at which an event is satisfied or unsatisfied is obtained depending on a condition part represented in a form of a logical arithmetic expression including an expression of fuzzy logic.

U.S. Pat. No. 4,945,476 to Bodick et al. discloses a software system for editing a knowledge base which is used as a tool in a diagnostic system. The software system includes stored pictorial images that are linked to case record text files.

U.S. Pat. No. 5,023,785 to Adrion et al. discloses a blood analysis expert system. The system accepts data in the form of hematologic parametric numerics obtained from a patient's blood assay. The system executes instructions stored in a memory and on the basis of the parametric numerics prints out diagnostic and hematologic messages applicable to the patient.

U.S. Pat. No. 4,839,822 to Dormond et al. discloses a computer system which generates suggested courses of treatment for persons who have been physically injured. A user is presented with a series of questions and graphical illustrations of physical trauma, which thee system uses to elicit pointed responses from the user. These responses are used, along with the contents of a stored knowledge base, by an inference engine to determine and generate a suggested treatment for the injury.

U.S. Pat. No. 5,255,187 to Sorensen discloses a computer aided process for diagnosing a patient's disease or illness. A doctor observes the patient's symptoms and extracts the patient's personal, family, and medical histories. These data are entered into a computer. A program resident in the computer manipulates the data and displays determinations of which disease or illness the patient has. Once the illness is identified, suggested treatment for the illness is displayed for the doctor.

These systems are useful in processing large amounts of information in order to determine a reliable result or other output. Some of these systems provide answers based on data provided in response to questions. However, guidelines which give rise to the questions to be asked may not always so simple to administer. Thus, while these existing systems provide general answers based on guidelines, they do not allow a user to create an interactive program based on guidelines that is tailored to particular situations. A more useful system would extract relevant data in an interactive manner from comprehensive guidelines, and process this data to provide another interactive process more suited to individual circumstances. This second process or program that is created could be used to extract further data in a more relevant fashion in order to formulate a qualification decision or a course of action.

SUMMARY OF THE INVENTION

Broadly stated, the present invention is an expert system that allows a person with limited computer skills to design and create an interactive data processing program application which can be used to elicit information based on guidlines. These guideline application programs ("GAPs") are created through the use of another application run by the top level expert system.

It is therefore an object of the present invention to provide a system which is efficient and effective at processing large quantities of data according to guidelines in order to generate an application program of questions to be administered to a data subject, the questions being based on a subset of the original guidelines such that the application program will in turn provide a next course of action suggestion based on the guidelines.

It is also an object of the present invention to provide a system which is efficient and effective at processing large quantities of data according to guidelines in order to generate an application program of questions to be administered to a data subject, the questions being based on a subset of the original guidelines such that the application program will in turn provide a qualification decision based on the guidelines.

It is another object of the present invention to provide a system which determines which input data is not required for a particular result and removes such data from the decision making process and from any subsequent program generated.

It is yet another object of the present invention to provide a system which alters the sequence of questions used to elicit input data according to the answers to previous questions and according to certain guidelines, for the purpose of generating a second, more directed application program.

It is still a further object of the present invention to provide a system which uses the results generated by a first interactive data processing application to generate a second interactive data processing application that is more directed and specific than the first application program.

It is a further object of the present invention to provide a system in which the second interactive data processing application further manipulates input data consisting of responses to questions and other knowledge tools in order to generate a response according to certain guidelines.

It is another object of the present invention to provide a system in which the second interactive data processing application is adaptable to generate a next course of action output according to certain guidelines for a number of different situations calling for such output, such situations including engineering design environments, petrochemical processing, nuclear plant procedures, housing and construction processes, real estate closing procedures, legal procedures, medical diagnosis and treatment, and sports training regimens.

It is also an object of the present invention to provide a system in which the second interactive data processing application is adaptable to generate a qualification decision output according to certain guidelines for a number of different situations calling for such output, such situations including human resource decisions, insurance risk assessments, lending risk assessments, low income housing qualification, educational testing evaluation, occupational testing evaluation, regulatory compliance, and college admissions qualification.

It is yet another object of the present invention to provide a system which includes a means for a user to respond to questions posed by the second interactive data processing application in order to provide input data.

It is still a further object of the present invention to provide a system which evaluates the quality of the data provided by the user in order to assess the reliability of the output generated by both the first and second interactive data processing programs.

It is another object of the present invention to provide a system which is flexible, in that the questions and guidelines may be edited in order to make the first and second interactive data processing programs and the output generated by the system more reliable.

It is a further object of the present invention to provide a system in which the second interactive data processing program is resident in an apparatus that is small and lightweight, enabling easy access to the system by a user.

These and other objects and advantages of the present invention will be apparent to those of ordinary skill in the art after inspection of the detailed description, drawings, and appended claims.

The present invention is a system utilizing a process which facilitates the design and implementation of guideline-based, computerized questionnaires and the preparation of computer-generated feedback reports and suggestions for users. The questionnaires are the GAP computer applications generated by the system level first application.

The system of the present invention includes a computer or other processing means in order to process data. The processing means may be of any type using any type of operating system. In the preferred embodiment, the processing means is an IBM or IBM clone (compatible) type computer operating in a Microsoft Windows environment which adheres to graphical interface conventions. An example of such a computer system that is contemplated to be suitable for use with the system of the present invention is a computer based on an Intel 80386, 80486, or pentium microprocessor, running Microsoft Windows version 3.1. This type of processing means will be used as the example processing means in describing the present invention. The use of this system as an example is not meant to limit the present invention to such a processing means, as it is contemplated that the present invention is suitable for use with any standard computer, and a person of ordinary skill in the art can determine many other data processing systems suitable for use with the system of the present invention.

The processing means includes input means, such as a keyboard, mouse, and/or joystick device. The processing means also includes presentation means for presenting output data to a user, such as a display monitor, printer, and/or other visual output means, and may also include sound output means for producing voice or other sound output to the user. The processing means further includes enough memory, connected to the input means, to store at least any input data accepted by the system, guidelines, and the system application program. The system must also have enough memory to run the system application and to store and run the GAP generated by the system application. The processing means also has logic means necessary for manipulating data and running the application programs according to the guidelines or other algorithms or rules. The logic means may be a microprocessor or other microcontroller. The logic means is connected to the memory means and the presentation means. The processing means may also include a hand-held processing means, particularly for use in running the GAP. The hand-held processing means would also include input means and presentation means.

Further, it is contemplated that the system of the present invention is suitable for use in any situation in which a qualification decision must be made. For example, in a human resource environment where an employee must be hired, an administrator usually has dozens of resumes to process for one job. All applicants may satisfy some requirements of the job and others may satisfy all requirements. These requirements are guidelines for making the hiring decision. However, some applicants are better suited than others, and although the guidelines can be followed to determine the best candidates, following numerous guidelines to organize numerous qualifications listed on numerous resumes can become an unmanageable task. Further questions must also be asked of the applicants in order to determine the best candidates. When directed to particular situations, such as in a federal regulatory environment, some questions may be dictated by law while others may be deemed impermissible by law. Some questions can be automatically obviated based on data already in the possession of the administrator. The system of the present invention automatically narrows the field and presents only a necessary list of second questions for each applicant. The list of questions is presented in the form of an interactive computer application generated by the first system application.

Other example situations in which it is contemplated that the system of the present invention can be used to make a qualification decision include insurance risk assessments, lending risk assessments, low income housing qualification, educational testing evaluation, occupational testing evaluation, government testing according to regulatory guidelines (the system can be used by both the government and by companies subject to the regulations), and college admissions qualification. In all these situations, someone or something is evaluated according to qualification guidelines. A large amount of input data and potential input data must be evaluated according to the guidelines before a qualification decision can be made.

It is also contemplated that the system of the present invention is suitable for use in any situation in which a next course of action must be determined. For example, in an engineering environment, numerous parameters and objectives must be evaluated according to design rules (guidelines) before proceeding with a design. Some components of a design can be borrowed from other designs, whereas other components must be designed from scratch. Further, based on the original parameters and objectives, certain design considerations can be ignored. The system of the present invention automatically distills only those design considerations that must be addressed, compiles input data in response to these considerations, and presents only a necessary list of secondary considerations for each design based on the input data. Again, these considerations take the form of a list of questions presented as an interactive application generated by a first system application.

Other example situations in which it is contemplated that the system of the present invention can be used to determine a next, best course of action include petrochemical processing, nuclear plant procedures, housing and construction processes, real estate closing procedures, legal procedures, medical diagnosis and treatment, and sports training regimens. In all these situations, a next course of action must be determined according to procedural guidelines. A large amount of input data and potential input data must be evaluated according to the guidelines before a decision as to a next step can be made.

For the sake of simplicity, the present invention will be illustrated using a medical diagnosis and treatment environment as an example situation. The present invention is not limited to this particular embodiment, as it is contemplated that the present invention can be used in a myriad number of other situations.

BRIEF DESCRIPTION OF THE DRAWINGS

FIG. 14 shows an example of a Library Reported Data Editor window.

FIG. 15 shows another example of a Library Reported Data Editor window.

FIG. 18 shows the Risk Score Editor window.

FIG. 20 shows the Fatigue Score Editor window.

FIG. 22 shows an example of a preamble message preceding an automatically generated Feedback Report.

FIGS. 82 and 83 show a system Guidelines listing.

FIGS. 84 and 85 show a system Risk Score listing.

FIG. 86 shows a system Risk Statement listing.

FIGS. 87–92 show an Algorithm Listing/Rules Report.

FIG. 93 shows a Short Patient Note Listing.

FIGS. 94 and 95 show a Suggestions Listing.

DETAILED DESCRIPTION OF THE PRESENT INVENTION

The system of the present invention is a data processing system which includes a system computer application program. The system application processes initial input data and other information tools. The input data is processed by the system application to generate a second application program. The second application program is an interactive questionnaire application used to elicit responses from the user in order to make a qualification decision or to recommend a next course of action. Examples of existing application programs and information tools in a health care context include preventive health screening systems, preoperative test selection programs, and geriatric functional status assessment instruments. The system application used with the system of the present invention can be written from scratch, adapted from existing programs, or assembled from pretested components stored in system libraries. All work on a system application may be performed in a temporary workspace on the system computer. Work at the system application level is performed by a skilled user, such as a medical care provider. Work at the questionnaire application level may be performed by an unskilled user, such as a patient.

Figure 1:
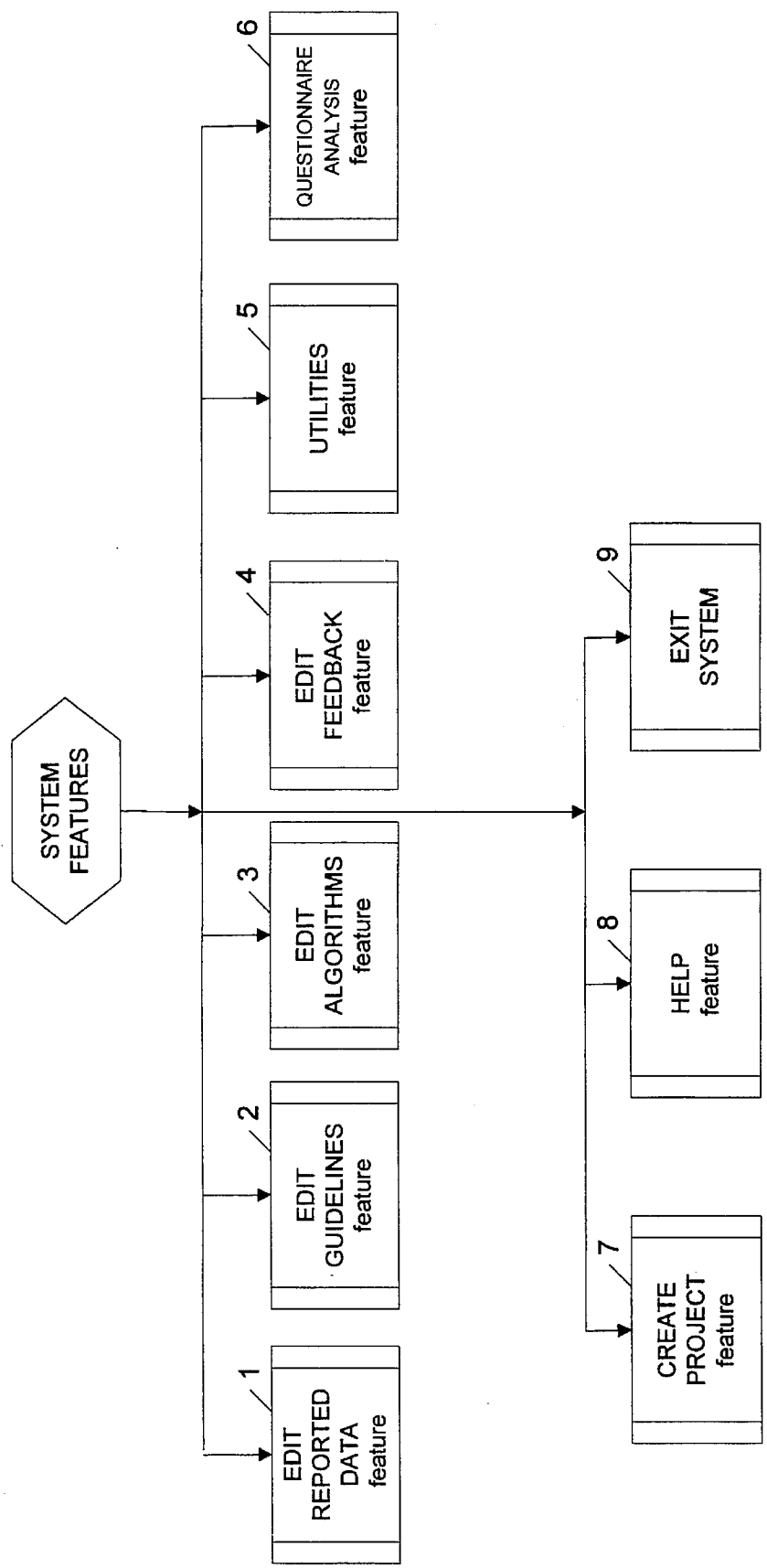
FIG. 1 shows an overview of features of the system of the present invention.

Referring to FIG. 1, an overview of system features is described. As shown, features of the present invention include an Edit Reported Data feature 1, an Edit Guidelines feature 2, an Edit Algorithms feature 3, an Edit Feedback feature 4, a Utilities feature 5, a Questionnaire Analysis feature 6, a Create Project feature 7, a Help feature 8, and an Exit System option 9.

Figure 2:
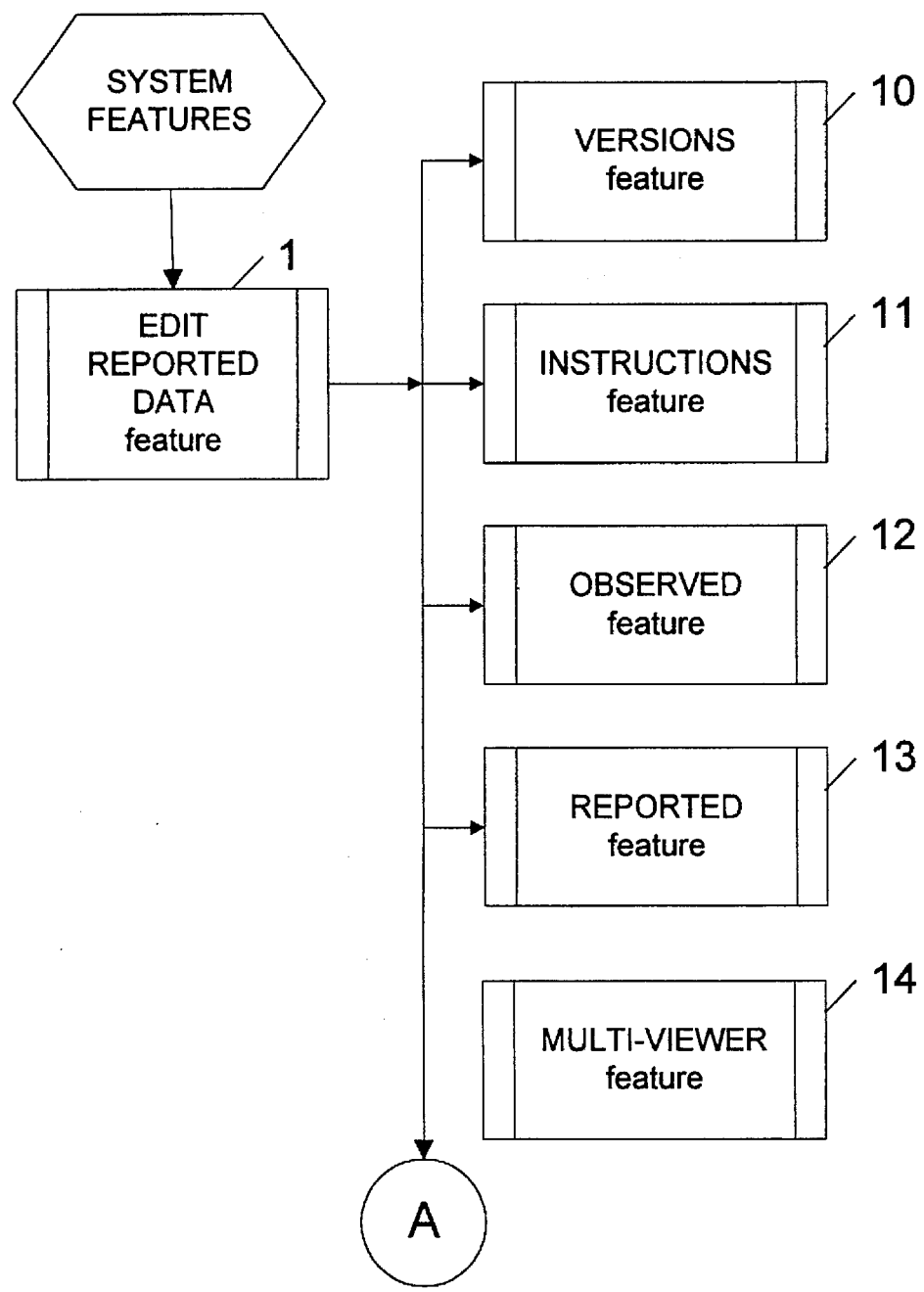
FIG. 2 shows details of the Edit Reported Data feature.
Figure 3:
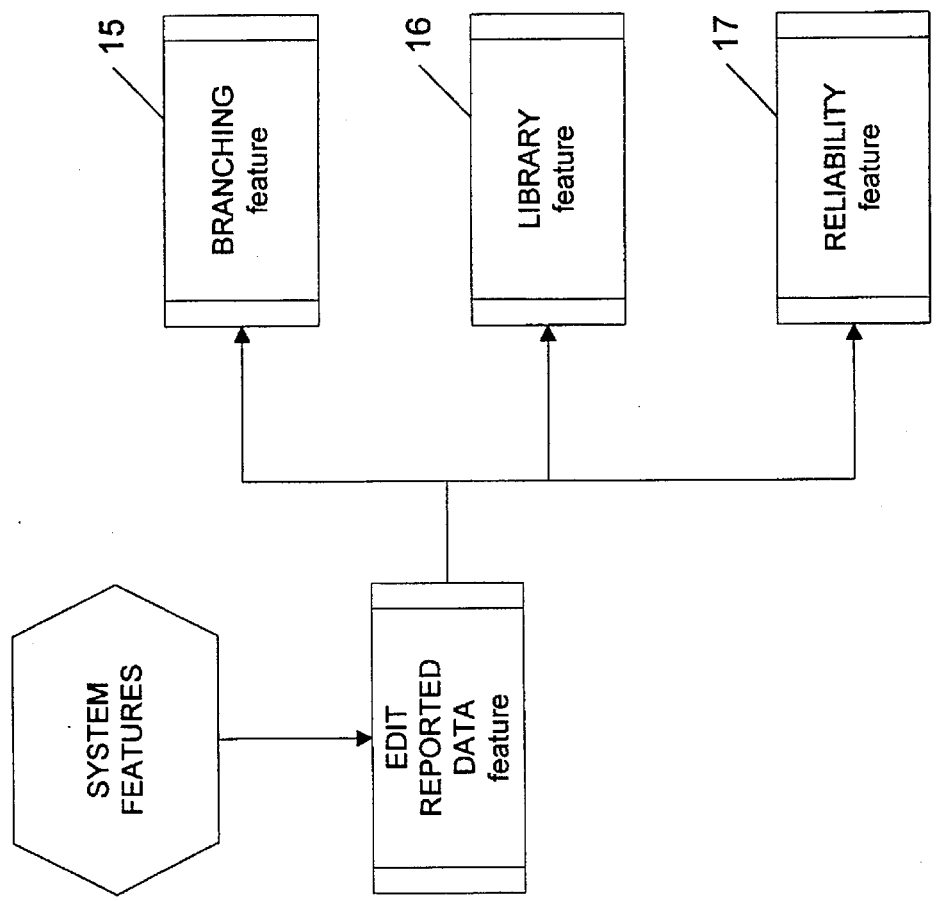
FIG. 3 shows details of the Edit Guidelines feature.

Referring to FIGS. 2 and 3, the Edit Reported Data feature is described. Reported data includes questions asked of the user or subject of the qualification decision, and may include sound and image data. The answers received in response to the questions will cause further questions to be asked, subsequent questions chosen based on answers to previous questions according to stored guidelines. Thus, the guidelines control the branching of the system question sequence as answers and other data are elicited. The Edit Reported Data feature allows the addition of new questions, deletion of questions, and other editing of reported data in order to make the ultimate system output more accurate. The Edit Reported Data feature itself has a number of features, including a Versions feature 10, an Instructions feature 11, an Observed feature 12, a Reported feature 13, a Multi-Viewer feature 14, a Branching feature 15, a Library feature 16, and a Reliability feature 17.

The Versions feature 10 compares and edits application program reported data and corresponding library reported data to ensure that the library reported data is updated when reported data is edited by a user. The Instructions feature 11 creates and modifies instruction text, sound data, and image data. The Observed feature 12 creates and modifies observed data. Observed data is that data which is not necessarily obtained as a result of question and answer procedure. Observed data may include demographic data and health and safety data.

The Reported feature 13 is used to create and modify reported data. As previously noted, this reported data may include multiple choice questions, preferences, likert scales, sound, and pictorial images. Using the Reported feature, reported data is created and modified in a single format. Using the Multi-Viewer feature 14, reported data can be created and modified in multiple formats.

The Branching feature 15 is used to review and modify reported data branch strategy. Using this feature, and using the guidelines as a basis, the logic controlling the order in which reported data is requested from the user or other data subject can be reviewed and modified.

The Library feature 16 is used to review library reported data. Library reported data is a list of all reported data used by all projects. After the library data is reviewed, the Library feature can also be used to capture library reported data of interest in place it in the current application program. The Reliability feature 17 can be used to review reported data reliability data. The reliability data includes data such as fatigue data, data regarding inconsistent answers, and other data related to the reliability of the application.

Figure 4:
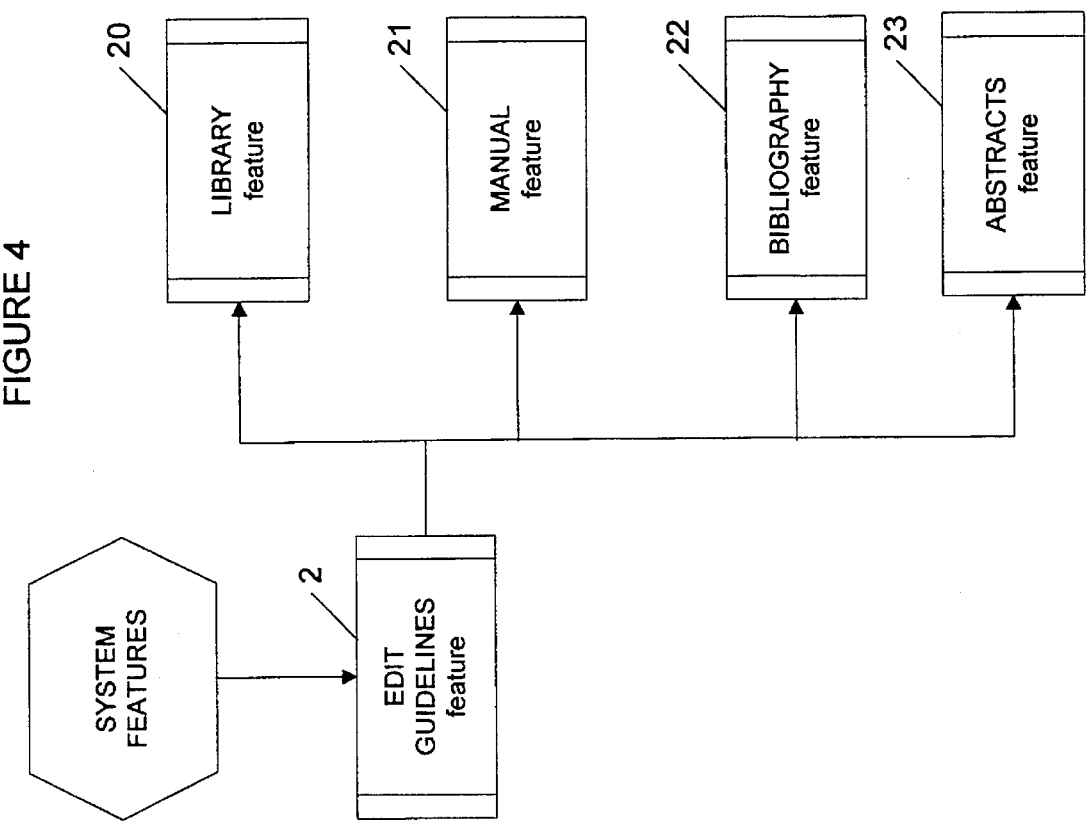
FIG. 4 shows details of the Edit Algorithms feature.

Referring to FIG. 4, the Edit Guidelines feature is described. The Edit Guidelines feature is used to review and modify the guidelines used by the system to control reported data branching logic. The Edit Guidelines feature includes a Library feature 20, a Manual feature 21, a Bibliography feature 22, and an Abstracts feature 23.

The Library feature 20 is used to review and edit the guideline library resource. The guideline library resource includes guidelines used to control the branching logic on a project. The Manual feature 21 is used to create and modify clinical software manuals. These manuals include all the guidelines used by the system for a particular project, and can be used to periodically evaluate the reliability of the system as applied to a particular project.

The Bibliography feature 22 is used to update and maintain the bibliography library. The bibliography library contains scientific evidence in the form of abstracts and articles that support the use of particular guidelines. The guidelines are referenced to the supporting evidence in the bibliography library. The Abstracts feature 23 is used to update and maintain the abstracts library. The abstracts library contains scientific evidence in the form of abstracts that support the use of particular guidelines. The guidelines are referenced to the supporting evidence in the abstracts library.

Figure 5:
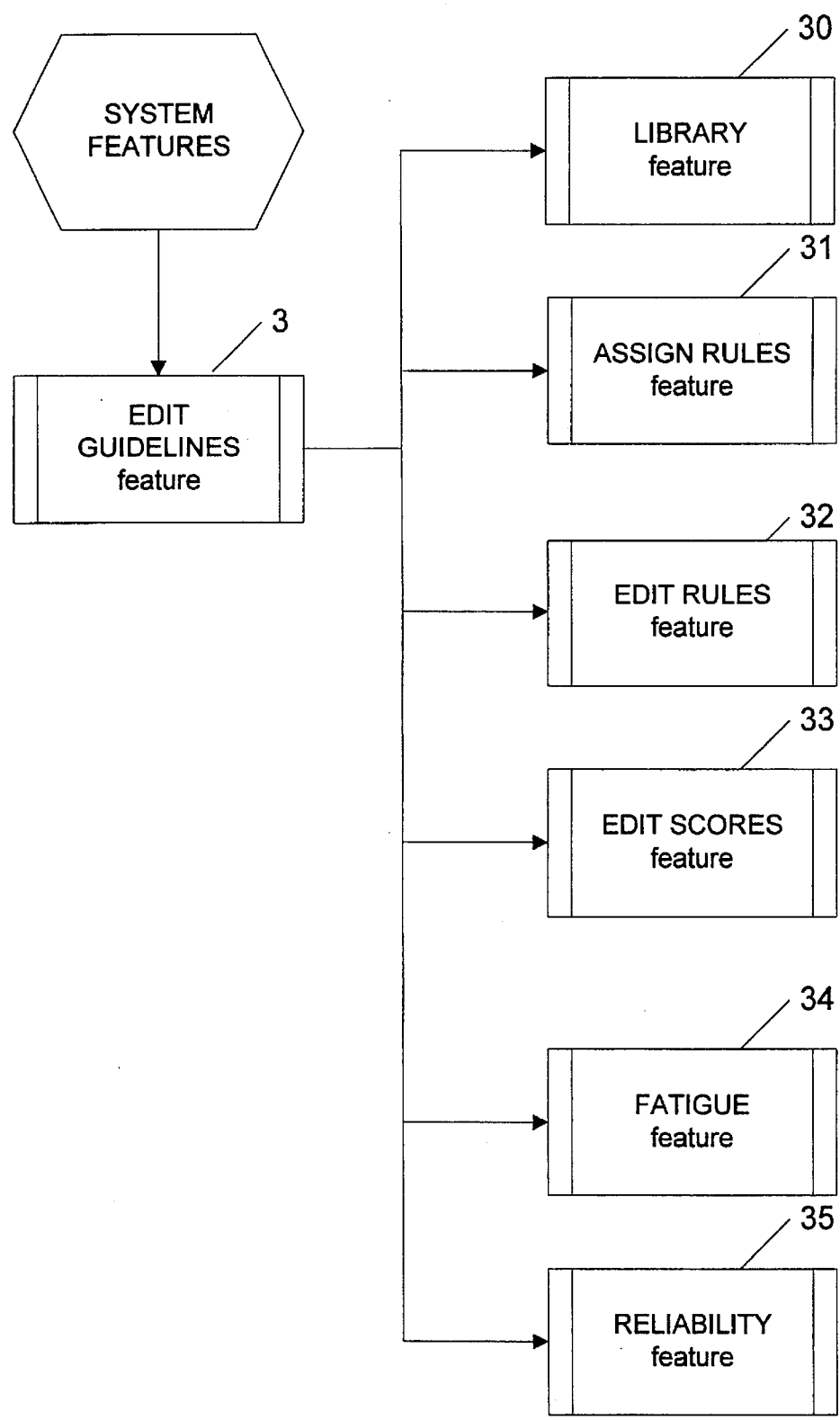
FIG. 5 shows details of the Edit Feedback feature.

Referring to FIG. 5, the Edit Algorithms feature 3 is described. The Edit Algorithms feature 3 is used to create, modify, update, and maintain the application outputs, such as recommendations, health risk statements, education materials, scores, fatigue data, and reliability data. These system outputs are based on the stored guidelines. The Edit Algorithms feature 3 includes a Library feature 30, an Assign Rules feature 31, an Edit Rules feature 32, an Edit Scores feature 33, a Fatigue feature 34, and a Reliability feature 35.

The Library feature 30 is used to update and maintain the library resource of guideline-based recommendations, health risk statements, and education materials. The Assign Rules feature 31 is used to assign decision-rules to the guideline library resource. The Edit Rules feature 32 is used to create and modify the application program guideline-based recommendations, health risk statements, and education materials.

The Edit Scores feature 33 is used to create and modify system scores which are calculated based on reported and observed data. These scores include risk scores and health status scores. The Fatigue feature 34 is used to create and modify fatigue index data. the fatigue index data is an indication of the reliability of reported data as the user or data subject becomes fatigued toward the end of the data elicitation process, and therefore measures the quality of the reported data. The Reliability feature 35 also measures the quality of the reported data and is used to create and modify the reliability index data. The reliability index data may be based in part on a measure of the consistency of responses elicited from a user or data subject.

Figure 6:
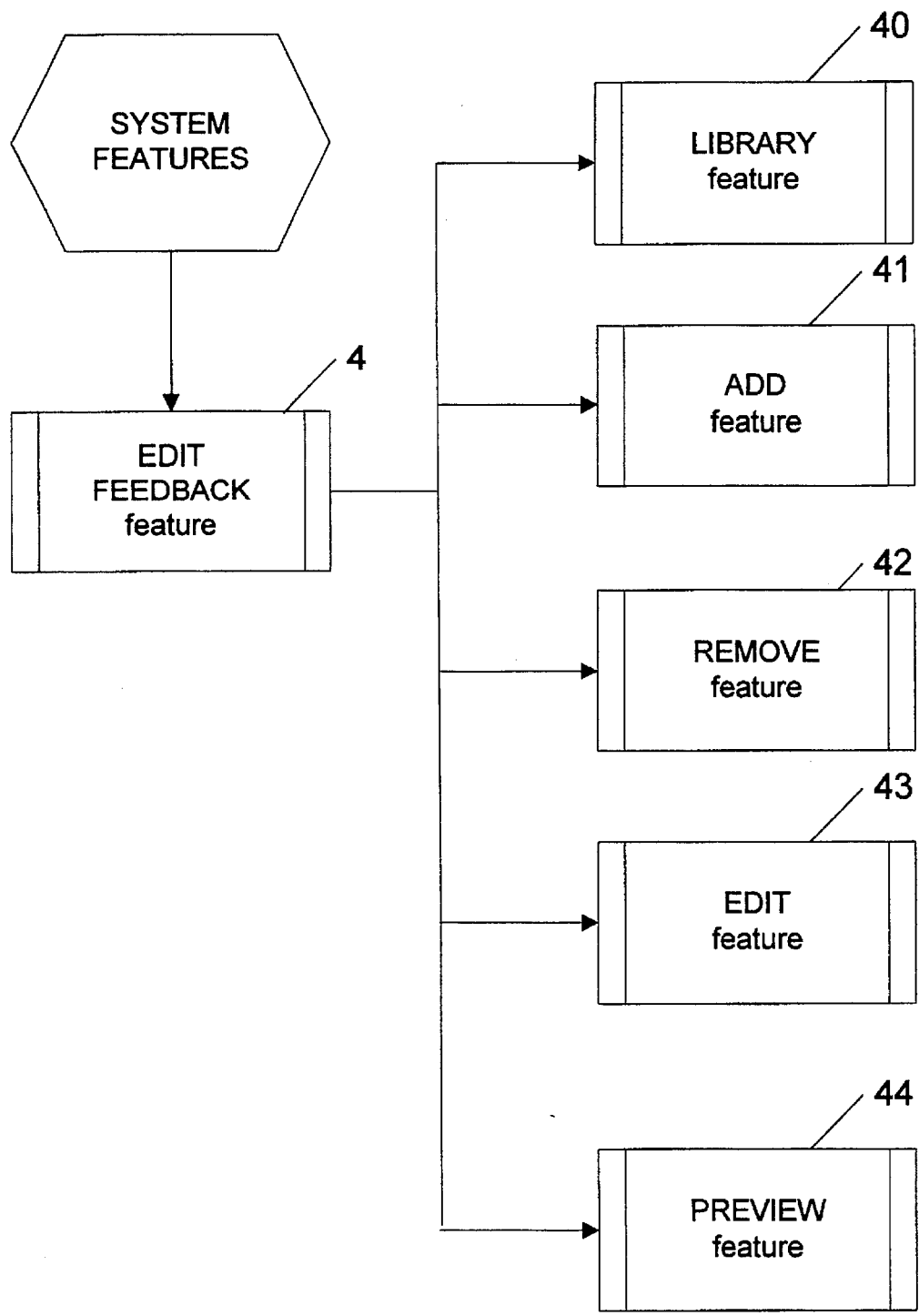
FIG. 6 shows details of the Utilities feature.

Referring to FIG. 6, the Edit Feedback feature 4 is described. The Edit Feedback feature 4 includes a Library feature 40, an Add feature 41, a Remove feature 42, an Edit feature 43, and a Preview feature 44.

The Library feature 40 is used to update and maintain a library of feedback reports. Feedback reports refers to any of several forms of data organization and presentation. The data presented depends on the needs given a particular project. If the report is to be printed, the system of the present invention is compatible with IBM-type personal computers, Macintosh computers, and computers running UNIX, among others. Further, the feedback reports can be in the form of electronic data records, images, or sound technology.

The Add feature 41 is used to create a new feedback report, and to switch to the Edit feature 43 after the report is created. The Remove feature 42 is used to remove a feedback report. The Edit feature 43 is used to modify the layout of the feedback report, and the Preview feature 44 is used to preview the feedback report with actual information.

Figure 7:
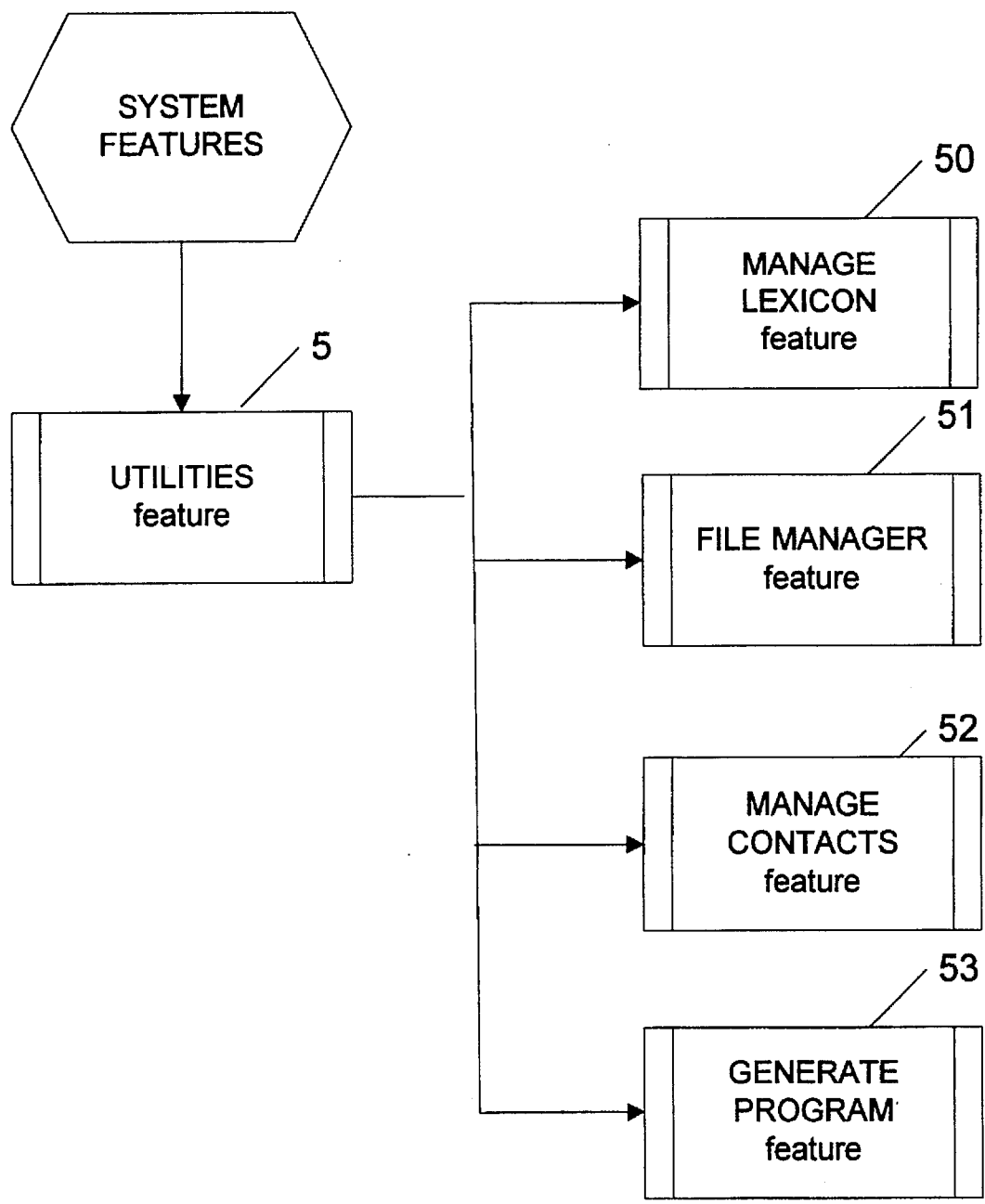
FIG. 7 shows details of the Questionnaire Analysis feature.

Referring to FIG. 7, the Utilities feature is described. The Utilities feature 5 includes system utilities for performing certain system level tasks. The Utilities feature includes a Manage Lexicon feature 50, a File Manager feature 51, a Manage Contacts feature 52, and a Generate Program feature 53.

The Manage Lexicon feature 50 is used to update and maintain classification lexicons. The File Manager feature 51 is used to update, archive, or backup system files. The Manage Contacts feature 52 is used to update and maintain contact lists and user lists. The Generate Program feature 53 is used to produce a software model for a specified hardware platform.

Figure 8:
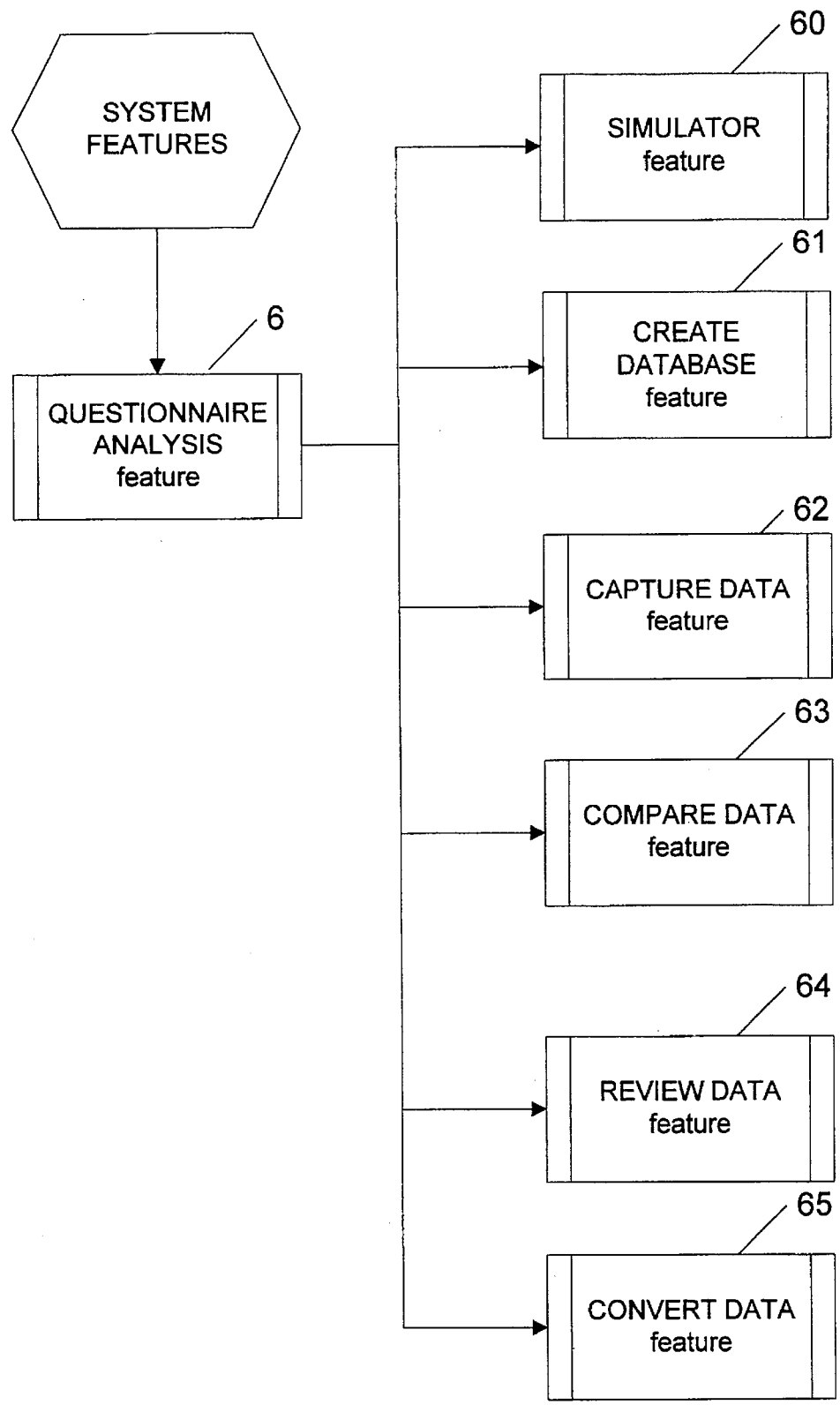
FIG. 8 shows details of the Create Project feature.

Referring to FIG. 8, the Questionnaire Analysis feature is described. The Questionnaire Analysis feature 6 is used to simulate an actual questionnaire application so that it can be checked for reliability and so that problems can be fixed before it is used by an actual data subject. The Questionnaire Analysis feature 6 includes a Simulator feature 60, a Create Database feature 61, a Capture Data feature 62, a Compare Data feature 63, a Review Data feature 64, and a Convert Data feature 65.

The Simulator feature 60 is used to simulate the software model using one of the many available hardware platform interfaces. The Create Database feature 61 is used to create a database for maintaining validity data for a particular software model and hardware platform. The Capture Data feature 62 is used to store the actual validity data.

The Compare Data feature 63 is used to compare the validity data with reported data in order to determine the reliability of reported data. The Review Data feature 64 is used to review the validity data used during the analysis of the questionnaire. The Convert Data feature 65 is used to convert the validity data into other data formats for further analysis.

Figure 9:
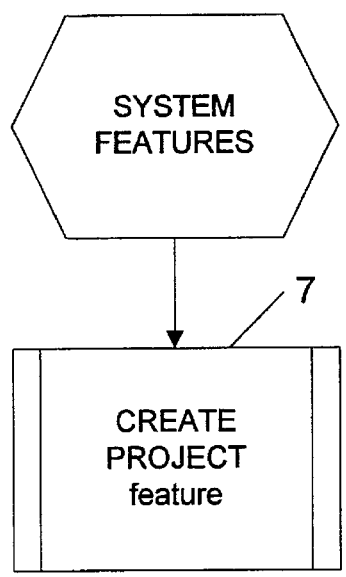
FIG. 9 shows details of the Help feature.

Referring to FIG. 9, the Create Project feature 7 is described. The Create Project feature 7 is used to select, create, or modify a project. Each project is a set of databases forming a software model.

Figure 10:
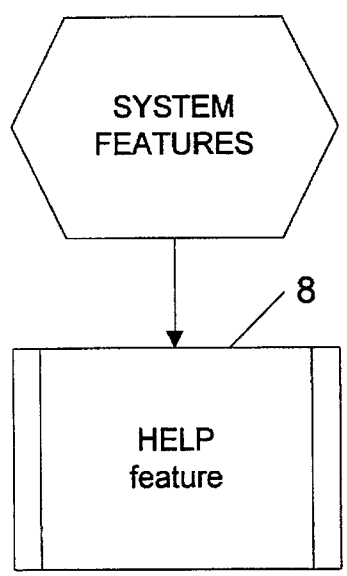
FIG. 10 shows details of the Exit System option.

Referring to FIG. 10, the Help feature 8 is described. The Help feature is used to provide on-line user help.

The Exit System option is used to shut down the system and return to the operating system, program manager, or desktop of the computer used to run the system.

Figure 11:
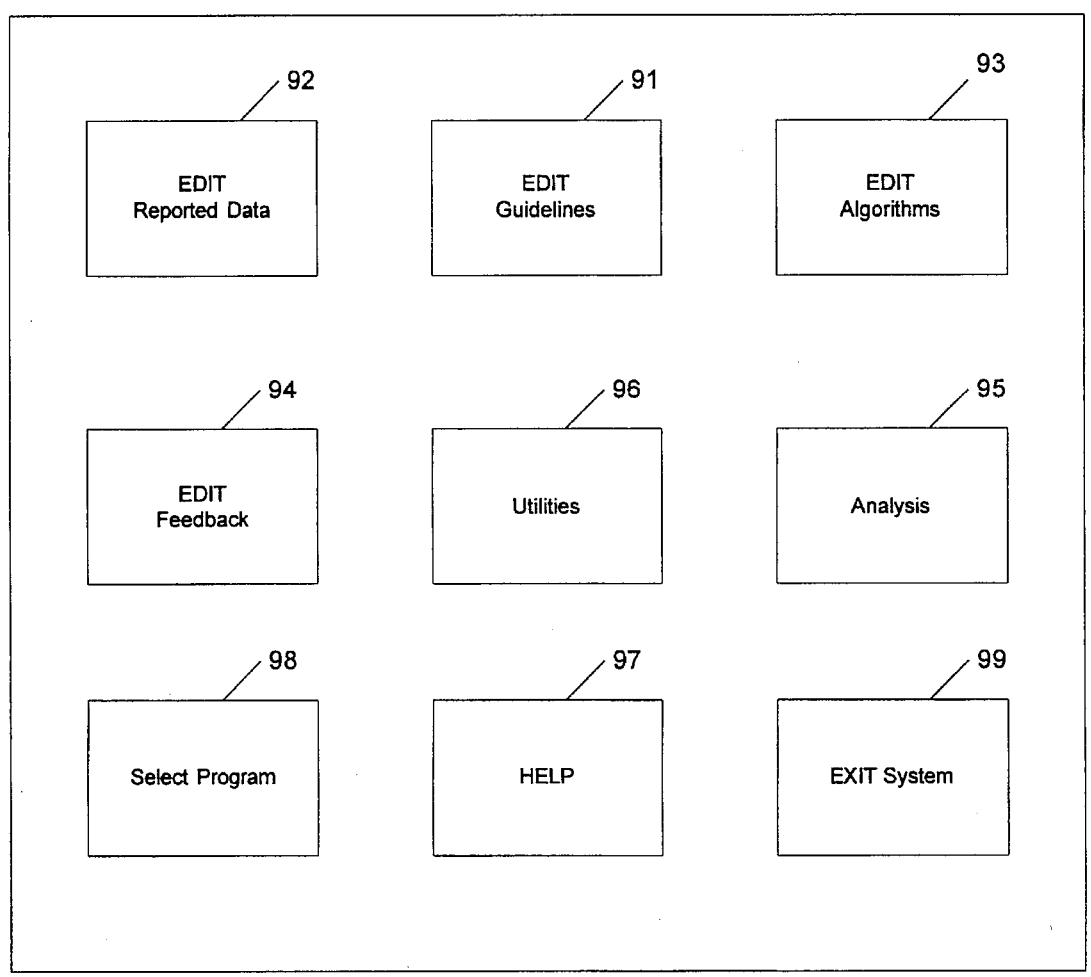
FIG. 11 shows an example system Main Menu window.

After launching the system, skilled users identify themselves and may be required to enter a password or comply with other access control requirements before an information window and main menu appear. As shown in FIG. 11, the Main Menu window, in the preferred embodiment, consists of large mouse or keyboard-activated command buttons, hereinafter referred to as pushbuttons, representing the five major system tools. These tools are: Edit Guidelines 91, Edit Reported Data 92, Edit Algorithms 93, Edit Feedback 94, and Questionnaire Analysis 95. A Utility Command pushbutton 96 accesses windows for file, vocabulary, and user registration utilities, a Help pushbutton 97 launches a context-sensitive help program, a Select Program pushbutton 98 selects applications to modify or defines new applications, and an Exit pushbutton 99 causes the system program to end. These pushbuttons access the features shown in FIGS. 1–10 and described above.

Although users may switch back and forth between system functions when modifying existing applications, new applications are built using system tools sequentially. First, clinical practice guidelines are abstracted and codified using Guideline Editor tools. Second, questions are written to solicit pertinent information from patients and/or health care providers using Edit Reported Data tools. Third, algorithms are generated using the Algorithm Editor. Fourth, Feedback Editor tools are used to prepare messages for clinicians and/or patients that will appear on printouts generated by the application program. Finally, a draft application program is tested using the Simulator function.

Guideline Editor

Figure 12:
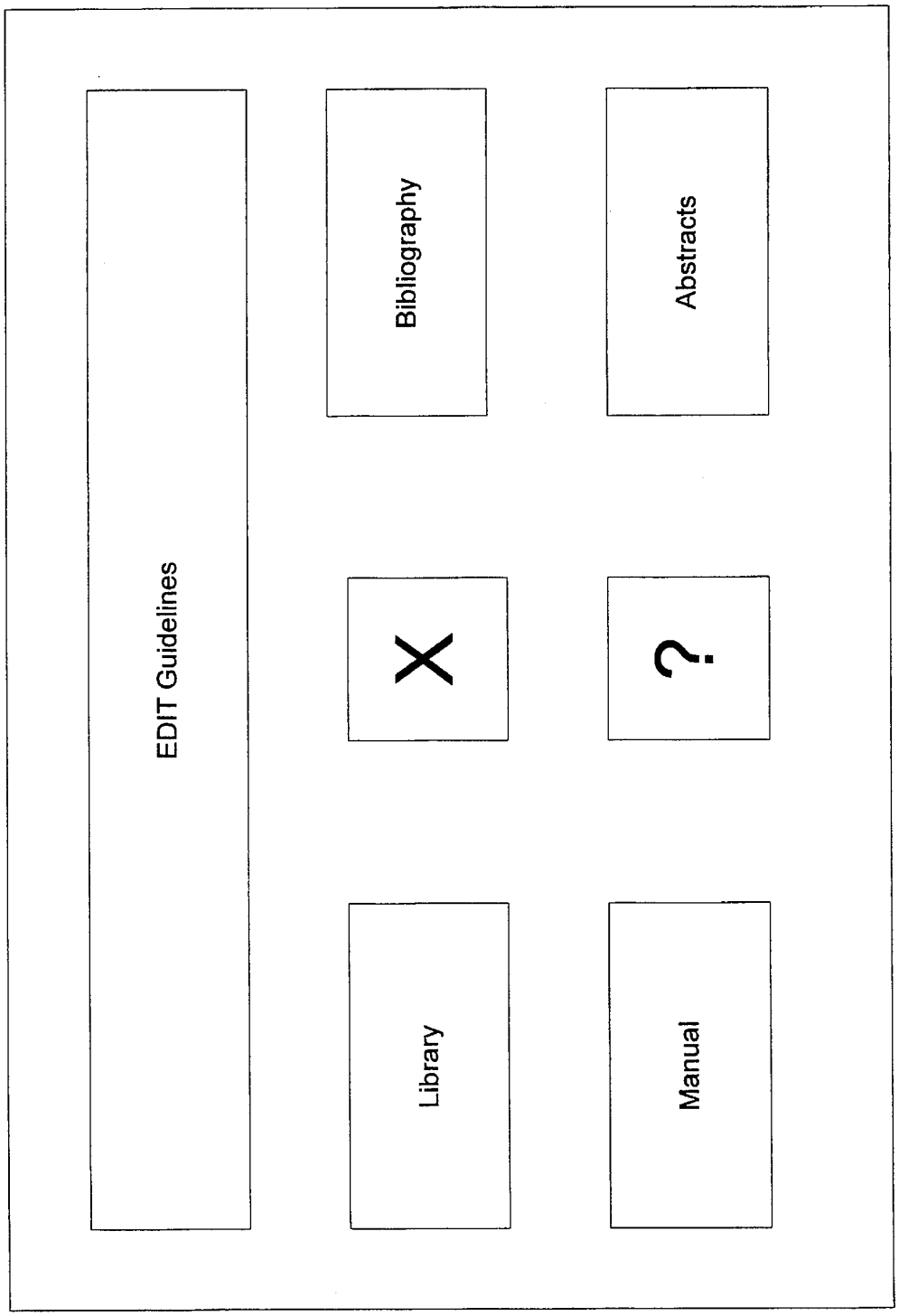
FIG. 12 shows an example of an Edit Guideline window.

The Guideline Editor is the centerpiece of the system of the present invention. FIG. 12 shows the window that is displayed to a user when the Edit Guidelines pushbutton 91 is selected from the Main Menu. In a health care context, the Guideline Editor includes a library of preventative care guidelines from health organizations which have critically appraised available scientific evidence before drafting the guidelines. Guidelines for other clinical domains are added as new applications are developed. Guideline summaries identify the source, sponsors, endorsers, and date of publication of a guideline. Targeted clinicians and patients are defined, and inclusion or exclusion criteria for guideline implementation are shown. These can be general (for example, sex and age) or selective (for example, personal or family past illnesses, present symptoms, and self-reported behaviors or concerns). Codes grading the strength of evidence supporting recommendations are shown, when available. In many cases, users can review structured abstracts of clinical practice guidelines and can retrieve original documents using information from a bibliographic database or using a serial number that indexes guideline documents in our archives. Guideline library entries attributed to the system represent the synthesis of recommendations from more than one source pertaining to a single medical intervention.

The guideline editor is also used to update published or system guideline digests. Printouts can be generated to tabulate related guidelines and to help clinicians review the evidence underlying system information tools. System libraries are dynamically linked to files that support the preparation of user manuals for application programs. In the preferred embodiment, these are Microsoft Publisher files.

Reported Data Editor

Figure 13:
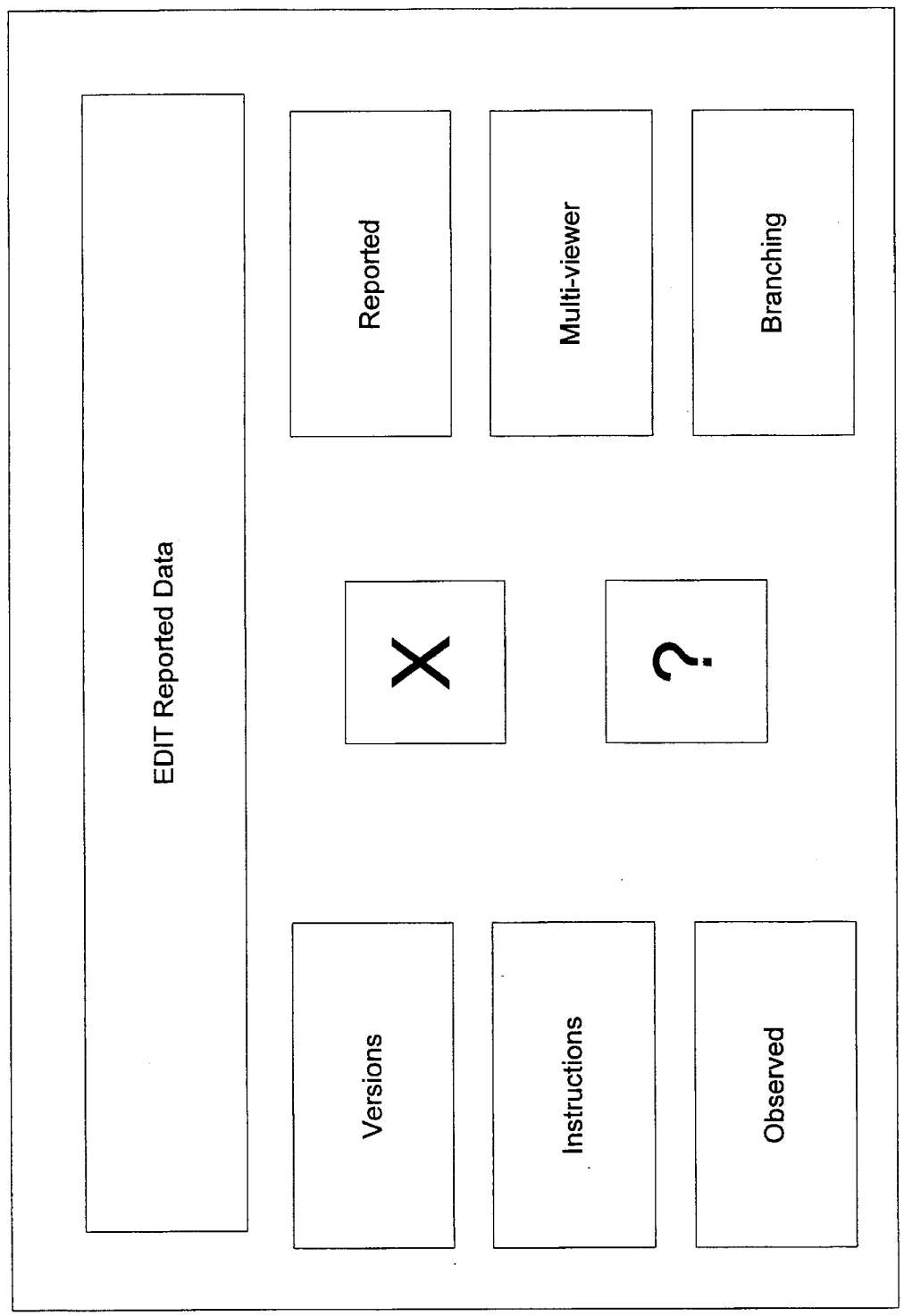
FIG. 13 shows an example of an Edit Reported Data window.

Reported Data Editor tools facilitate the writing and revision of interactive questionnaire applications. In a health care context, these are patient-administered questionnaires. FIG. 13 shows the window that is displayed to a user when the Edit Reported Data pushbutton 92 is selected from the main menu.

As with other system modules, users can query a resource library and draw upon previously administered and validated guideline-based questionnaires. The reported data library holds recent versions of all successful field-tested questions. Some reported data are also derived from validated health survey instruments. Most system reported data are written specifically for human-computer dialogue and have been tested for comprehensibility and test-retest reliability where patients or other unskilled users interact directly with a computer.

Figure 16:
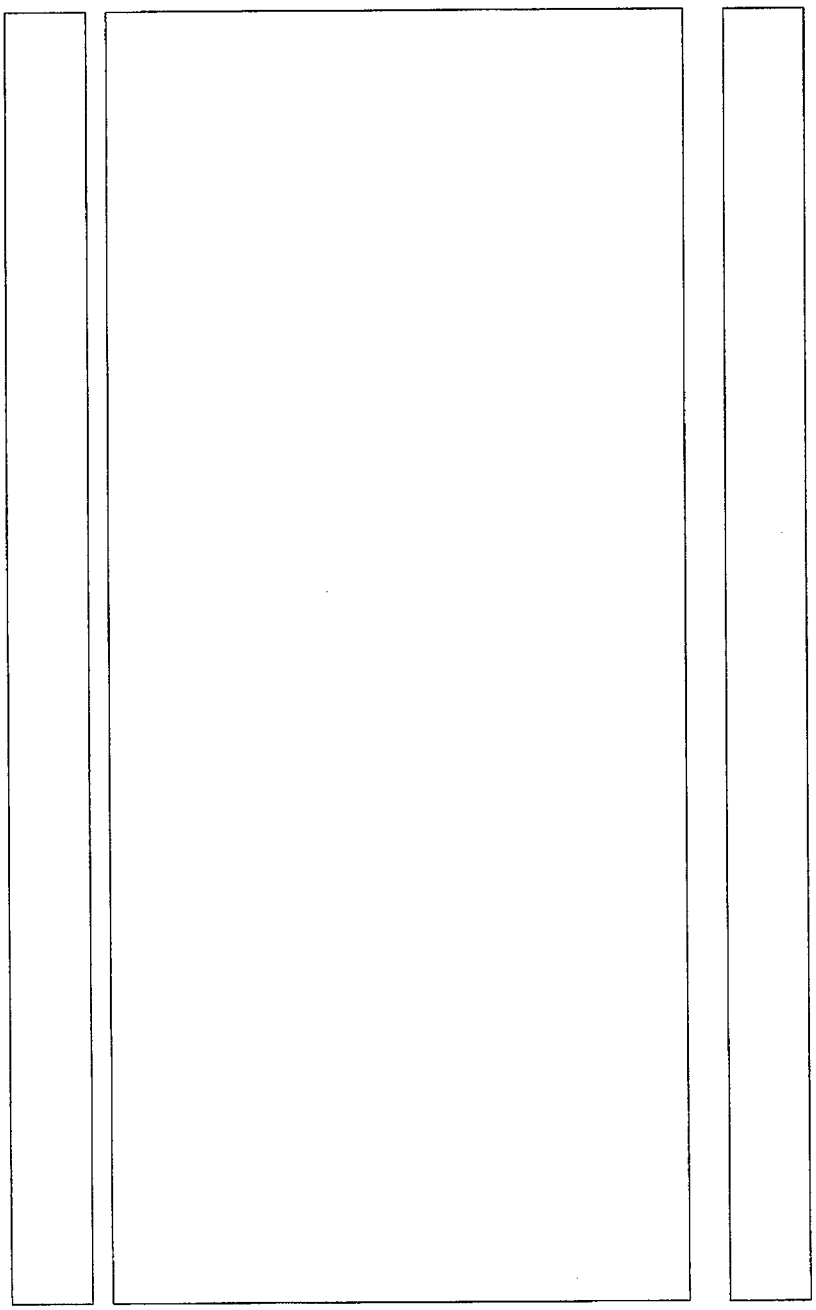
FIG. 16 shows a Library Question Data window for entering data from clinical trials.

Users can scan the contents of the Reported Data Library using multi-question windows, and filters can be used to restrict the view to questions matching specific categories, subcategories, and keywords. FIG. 14 shows a Question Library window. In the preferred embodiment, users can select reported data for export to an application program using point-and-click techniques. FIG. 15 shows the library Reported Data Editor, which shows the dates reported data questions were written and updated, commentary of expert reviewers, citations to the clinical literature, copyright notices, and editing tools for modifying library questions. FIG. 16 shows a window for entering data from clinical trails and structured abstracts of original studies. Frequency tables show how different age and sex-specified patient groups have answered particular questions in the past, and test-retest reliability tables show the stability of particular patient responses. Because all system information tools capture patient data electronically, system Question Libraries continually grow in size and power and as clinical outcomes data are captured from clinical studies, the library will be populated with indicators of the probability that reported data will identify patients at risk for specific health outcomes.

Thus, the Reported Data Editor offers other tools for writing and revising questionnaires. One window facilitates writing instructions for patients. Another is optimized for adding, copying, deleting, and editing questions. Two multi-question windows help users to quickly alter the order and branching paths for groups of questions.

Users can write questions that employ a number of different response formats, such as "yes/no/not sure", multiple choice, and likert scales. The program can branch to a number of different places contingent on patient answers; these are set quickly from pop-up requestors that list all questions in the application. User choices are audited and warnings are posted if an item exists in the library in a different form or if branching rules, algorithms, or feedback reports could be affected by the alteration or deletion of a question.

An Objective Data Editor is used to write dialogue for capturing quantitative data from patients or clinicians (for example, the patient's weight, blood pressure, or serum cholesterol level) and to define application-specific variables.

Questionnaires are assembled using conventional questions that are presented to patients or clinicians and special "group questions" that remain invisible during application program execution. Special group questions contain logic strings that are evaluated before executing a calculation, branching to a different part of the questionnaire, or executing a subroutine. Any objective data variable, previous question response, or health risk score can be used in special group statements.

Algorithm Editor

Figure 17:
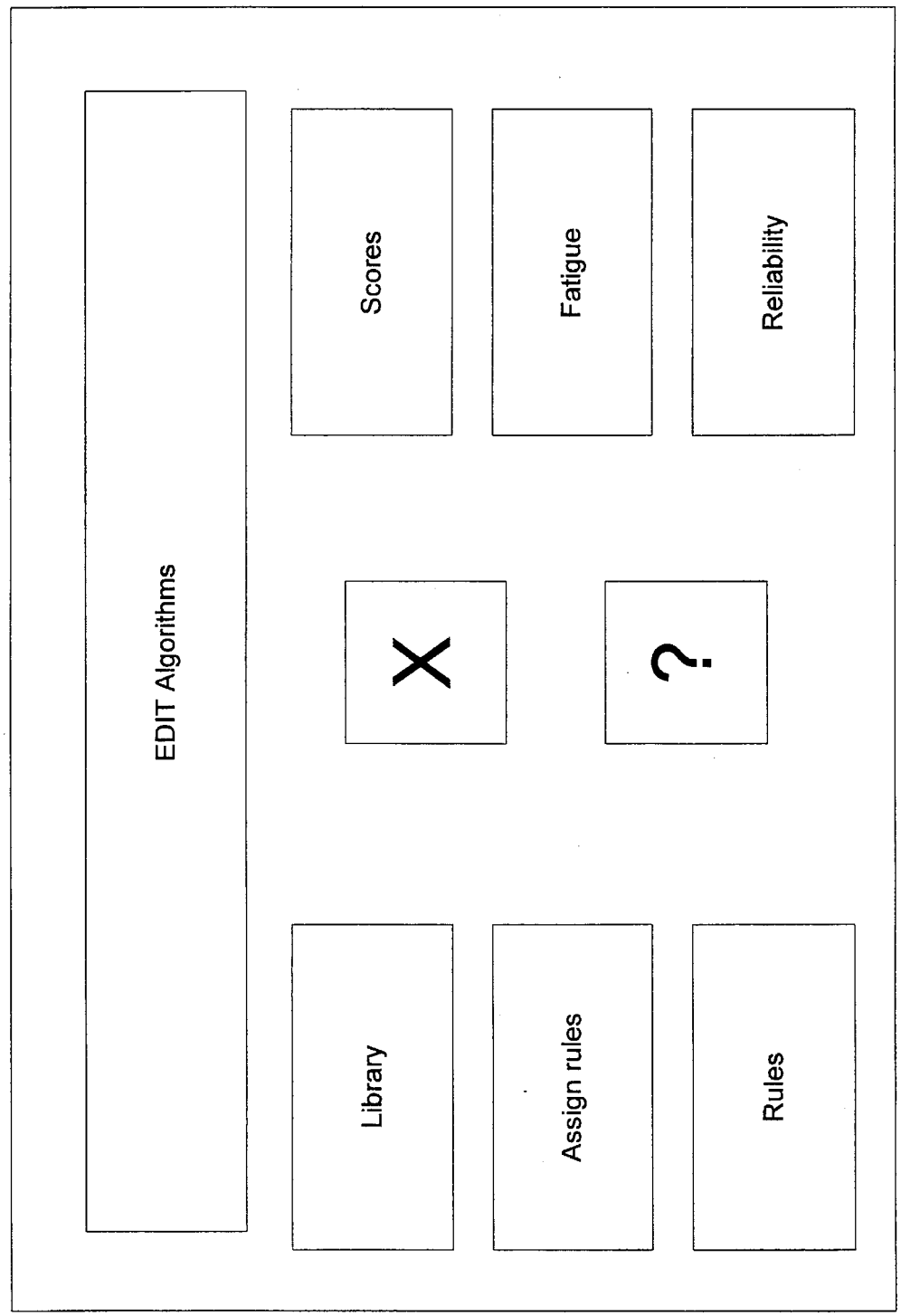
FIG. 17 shows an example of an Edit Algorithms window.

When all questions and other reported data for a new application have been written, the Algorithm Editor is used to define how responses to questions, other reported data, and objective data variables will be used to match guideline-based recommendations to individual patients. FIG. 17 shows the window that is displayed to a user when the Edit Algorithms pushbutton 93 is selected from the Main Menu.

A Risk Score Editor facilitates the definition of risk scores by assigning positive or negative weights to different patient answers. These weights are summed to yield the risk score. For example, a cardiovascular risk score may increase by 2 points if a first degree relative suffered a heart attack before age 50 and may decrease by 1 point if a post-menopausal woman reports use of estrogen replacement hormones. FIG. 18 shows a typical Risk Score Editor window.

Figure 19:
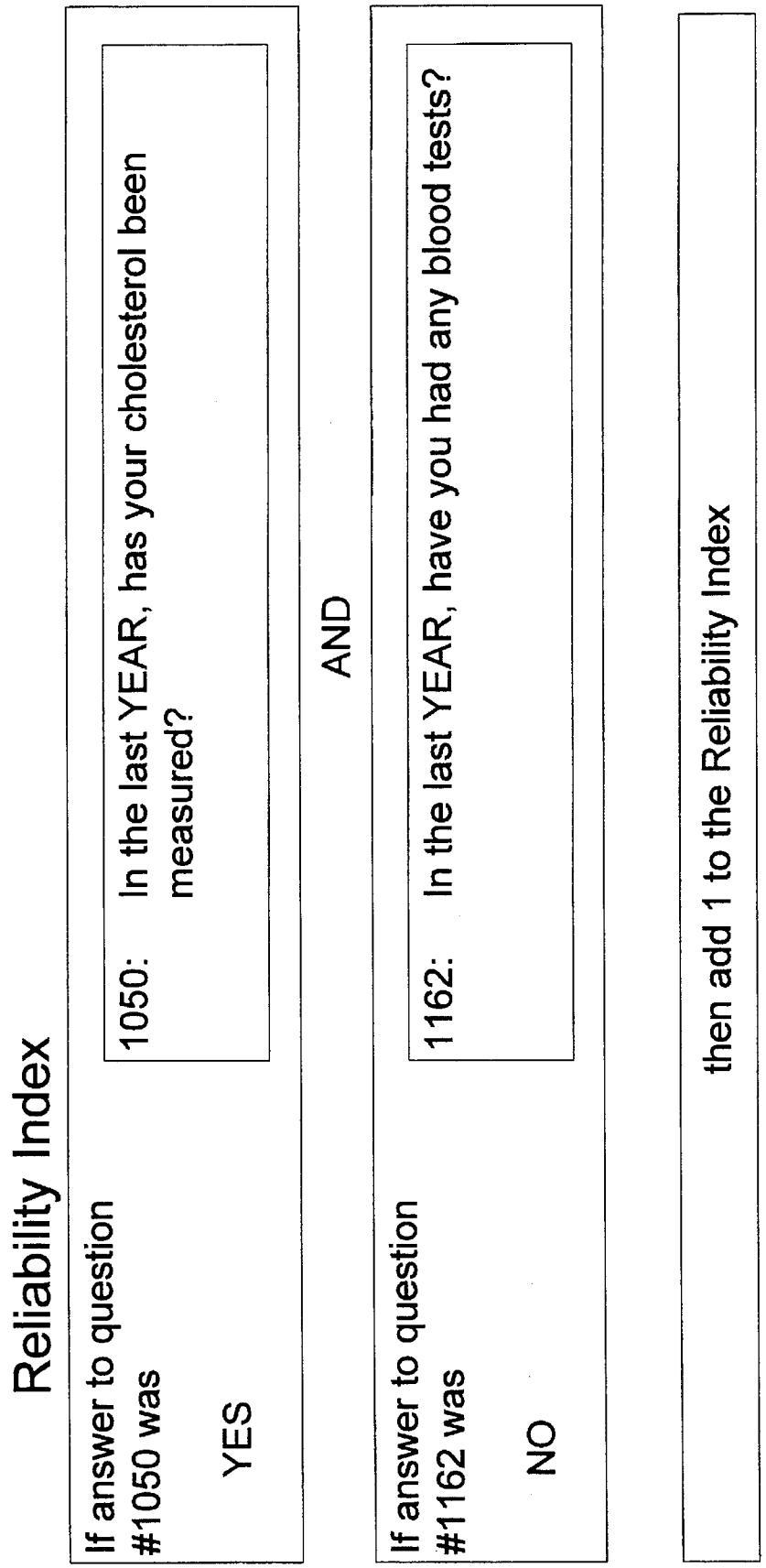
FIG. 19 shows the Reliability Index window.

FIG. 19 shows a Reliability Index window. This window facilitates the construction of a Reliability Score that reflects logical inconsistencies in patient answers to a questionnaire, an unacceptable frequency of "NOT SURE" responses, and positive answers to questions about difficulties patients may have with a questionnaire. These factors are all considered by the system in determining the reliability of the results of the questionnaire process. Likewise, a Fatigue Score reflects patient response times exceeding defined thresholds, as well as self-reported concentration difficulties. The Fatigue Score is also considered by the system in determining the reliability of the results of the questionnaire process.

FIG. 20 shows a typical Fatigue Score Editor window. Clinical Algorithms are used to determine how patient or clinician-derived information will be audited, summarized, and reported. The Clinical Algorithms also codify practice guidelines and determine whether particular interventions will be included among suggestions for the clinician and/or patient. Users can review the contents of an algorithm library and can also capture pre-existing algorithms for incorporation into new applications. Ultimately, the algorithm library will be populated with data derived from the clinical trails about performance characteristics of individual algorithms.

New algorithms are preferably built using a point-and-click Rule Builder. Users can combine up to 15 distinct logical conditions related by "AND" or "OR" connectors to establish relationships among inputs, resulting in the desired outputs. The state of any objective variable (for example; age, sex, blood pressure), Risk Score (for example, breast cancer risk score), or answer to any question can be included in an algorithm. The system of the present invention helps users by presenting drop-down lists of all variables, scores, and questions in an application and alerting users to the values that are allowed to be tested. A set of algorithms can also be audited to produce a report of logical errors.

Feedback Report Editor

Figure 21:
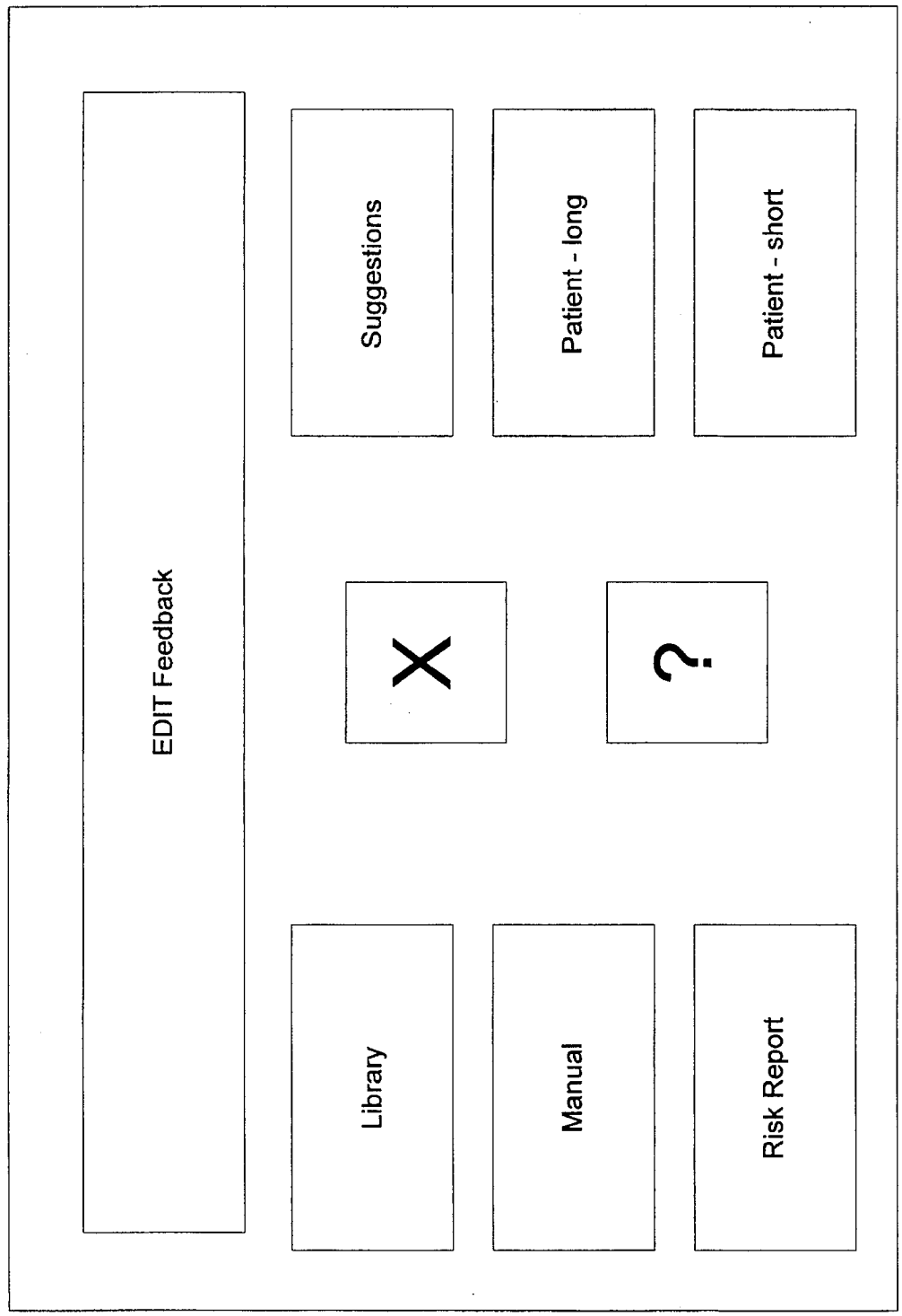
FIG. 21 shows an example of an Edit Feedback window.
Figure 23:
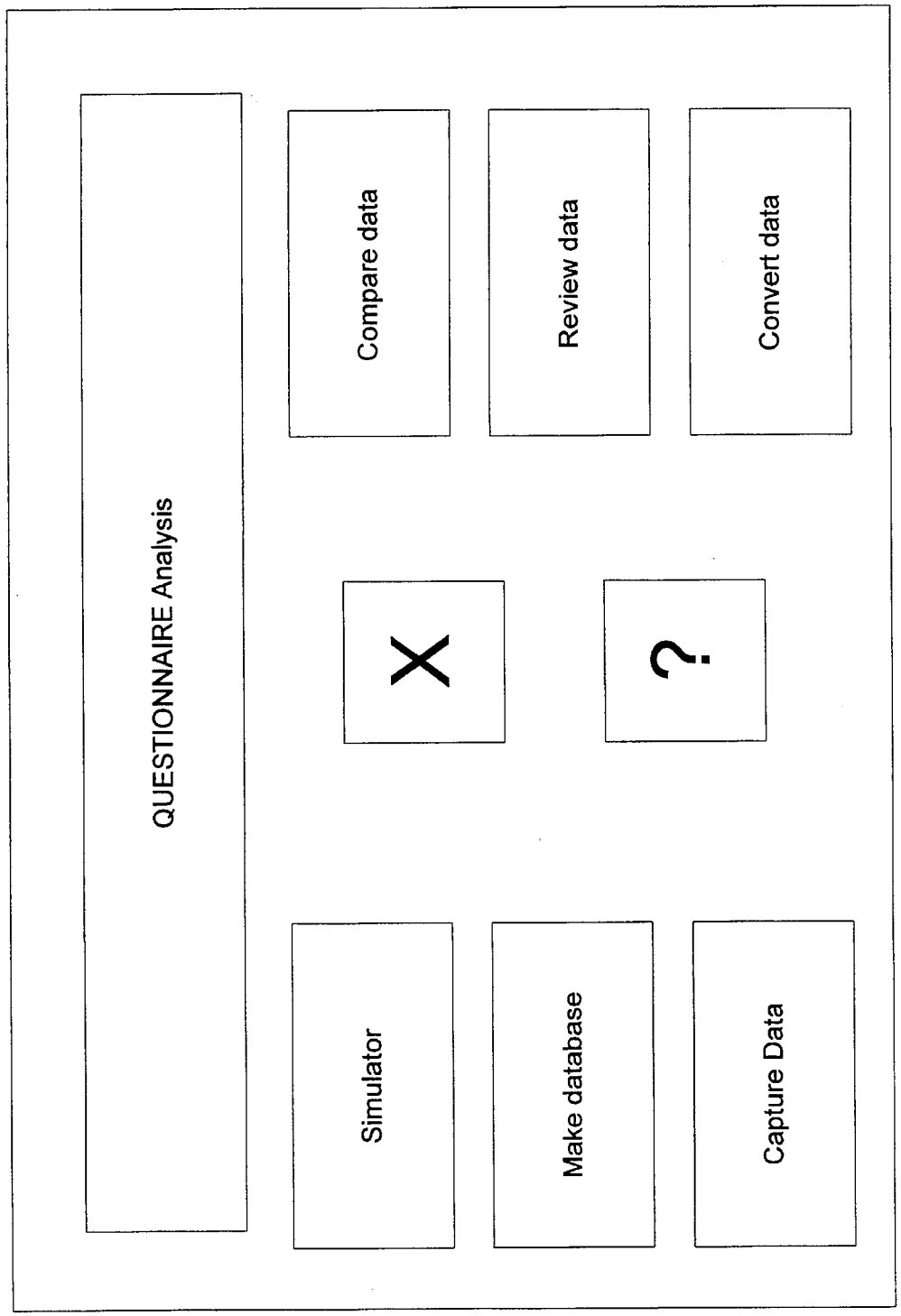
FIG. 23 shows an example of a Questionnaire Analysis window.
Figure 24:
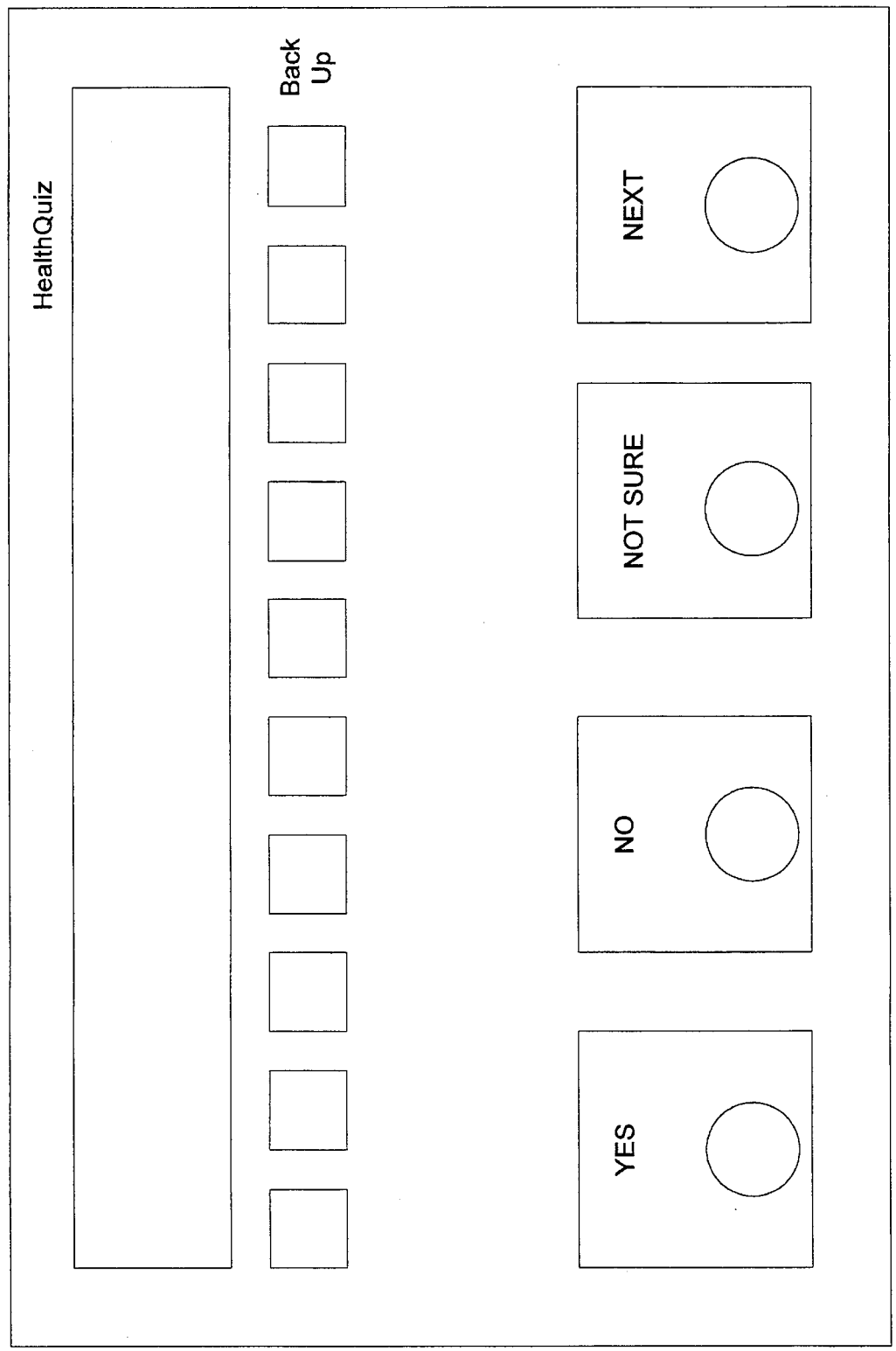
FIG. 24 shows an example of a hand-held computing unit graphical screen.
Figure 25:
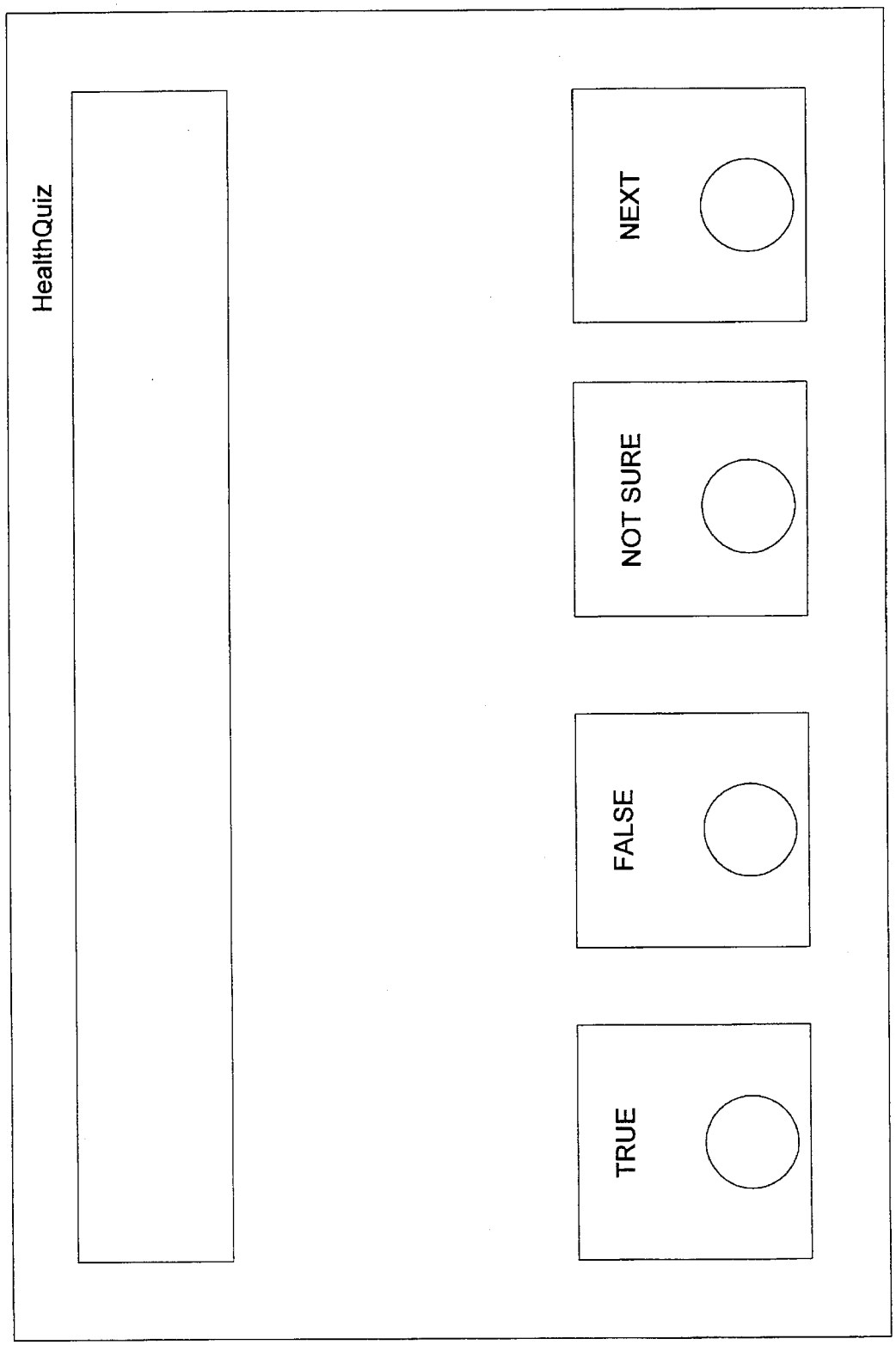
FIG. 25 shows an example display for the hand-held computing device.
Figure 26:
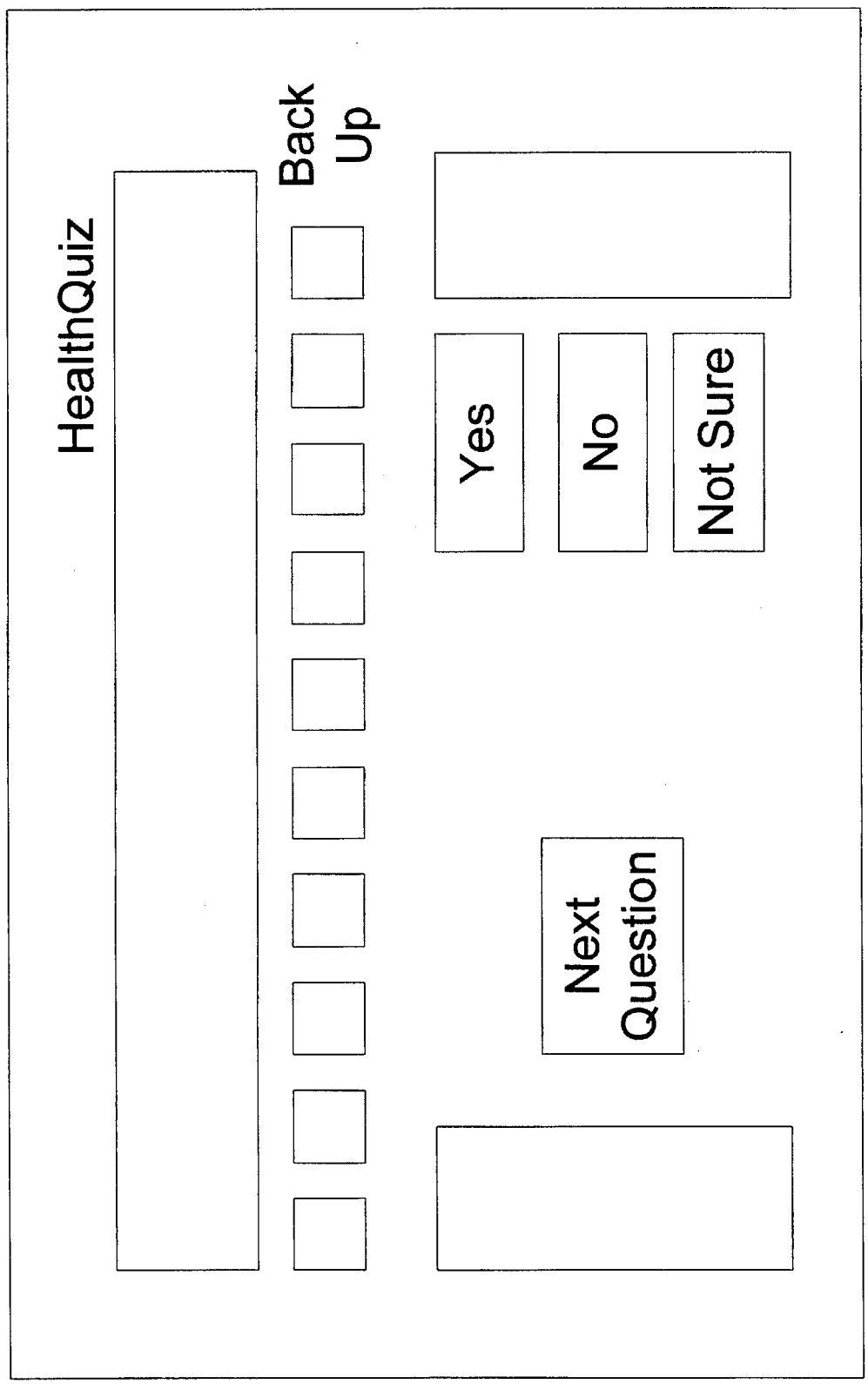
FIG. 26 shows another example display for the hand-held computing device.
Figure 27:
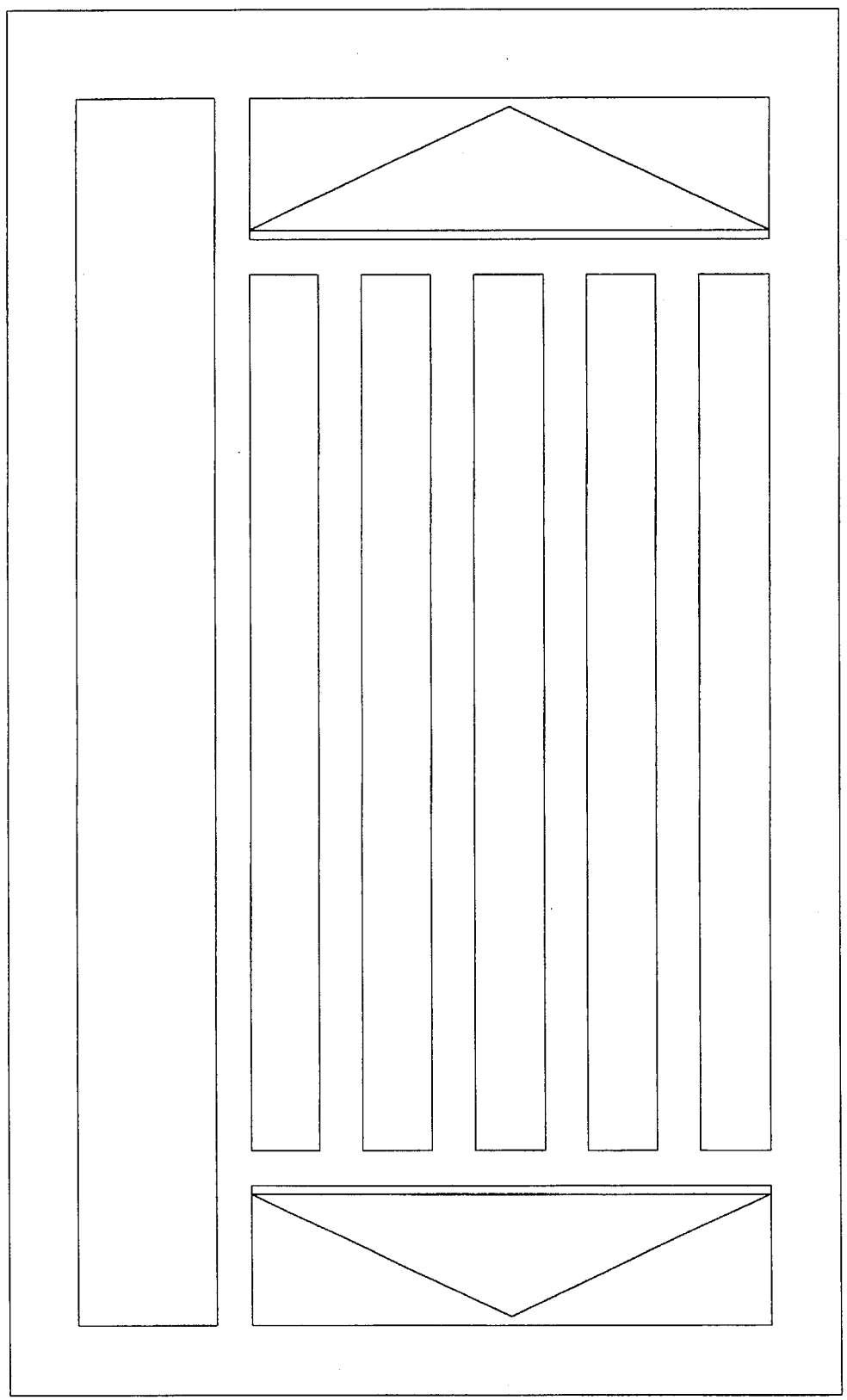
FIG. 27 shows another example display for the hand-held computing device.
Figure 28:
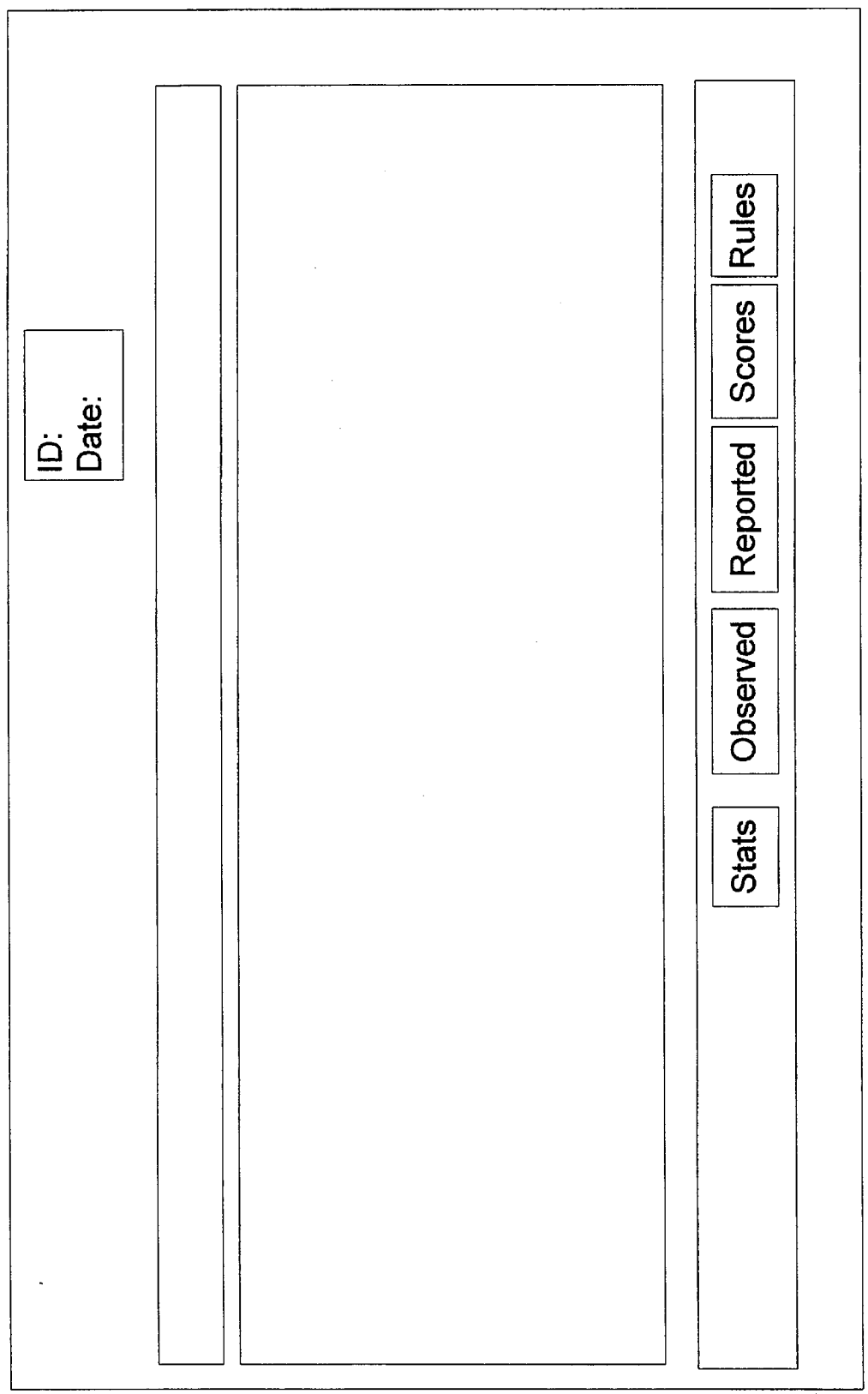
FIG. 28 shows an example of a hidden window for the hand-held computing device.

The Feedback Report Editor simplifies the task of writing messages to be included in reports for physicians and/or patients and of defining the layout of those reports. FIG. 21 shows the window that is displayed to a user when the Edit Feedback pushbutton 94 is selected from the system Main Menu. Again, a library includes messages written to support other applications. All feedback messages are linked to algorithms and automatically appear in a Feedback Report if the algorithm evaluates to "true".

Templates exist for four reports that have are commonly used in the health care context. A Risk Report template summarizes pertinent positive and negative findings from a patient and/or clinician administered questionnaire. Patient identifiers, demographic information, and indicators of expected questionnaire reliability appear immediately following the preamble. A Clinician Suggestion template helps users to design order sheets for providers and also to design lists of suggested medical interventions prioritized according to a patient's risks and self-reported interest in learning about a health intervention. The Short Patient Feedback template helps users to organize printouts with brief, informative messages about a number of interventions and the Long Patient Feedback template is for more detailed educational messages for patients.

Simulator

At any time during the development of a Questionnaire application, the Simulator may be used to emulate the performance of a completed Questionnaire application preferably to be run on either a hand-held computer or on a Microsoft Windows-compatible device. The Simulator may be accessed by selecting the Analysis pushbutton 95 from the system Main Menu. FIG. 13 shows the window that is displayed to a user when this pushbutton is selected. Users interact with graphical windows exactly as patients and clinicians would see them. FIG. 14 shows an example of a graphical window that would be seen on the hand-held computing unit and which can be observed using the Simulator. Users may also bring up a panel of pushbuttons for auditing tools that help trap "bugs" in an application program. In most cases the Simulator can post messages about how a problem can be remedied and which system tool should be used to do so. Users can switch to the needed tool, pre-loaded with the offending questions, algorithm, or feedback report.

Implementing Application Programs

The system of the present invention generates software for the hand-held computer on a PMCIA RAM memory card. It also generates software for use on Windows or Pen-Windows devices. The real power of the system is realized when application programs are pilot tested in clinical settings. Using a portable computer, the system can customize or correct questionnaires, algorithms, and feedback reports and can generate new program code for immediate use in the field.

Other Features

When used in the health care context, all system modules comply with a controlled vocabulary that is consistent with National Library of Medicine medical subject headings. The system includes utilities for rapidly updating program and application files for other collaborators, making backup copies of program files, and generating dBaseIV compatible files. The system includes a Help pushbutton which enables the user to select any area of a system window to obtain context-sensitive help messages.

Clinical Applications

The system can be used to develop or customize a number of information tools that use the hand-held computer. The hand-held computer is preferably a four-button, lap-top, battery-powered video device on which health questions are read and answered by a patient. Like a video game, it has an exceptionally simple user interface and is easily moved from one patient to another. By reading a large-character display, patients receive instructions on using the computer to indicate, change, or correct answers to questions. FIGS. 15–17 show example displays for the hand-held computing device. In addition, there are hidden pushbuttons and hidden windows that permit practitioners to add information to a patient record and to navigate through a series of menus which control the computer's various functions. FIG. 18 shows an example of such a hidden window.

Existing system-derived information tools include a pre-operative test selection program, a preventative health screening program, and a functional status assessment instrument. Information tools in the health care context can also include an interactive hormone (estrogen) replacement guideline for peri-menopausal women, a blood donor screening program, and an adolescent health module. Other information tools for health care and other applications may be developed and used as well.

Figure 29:
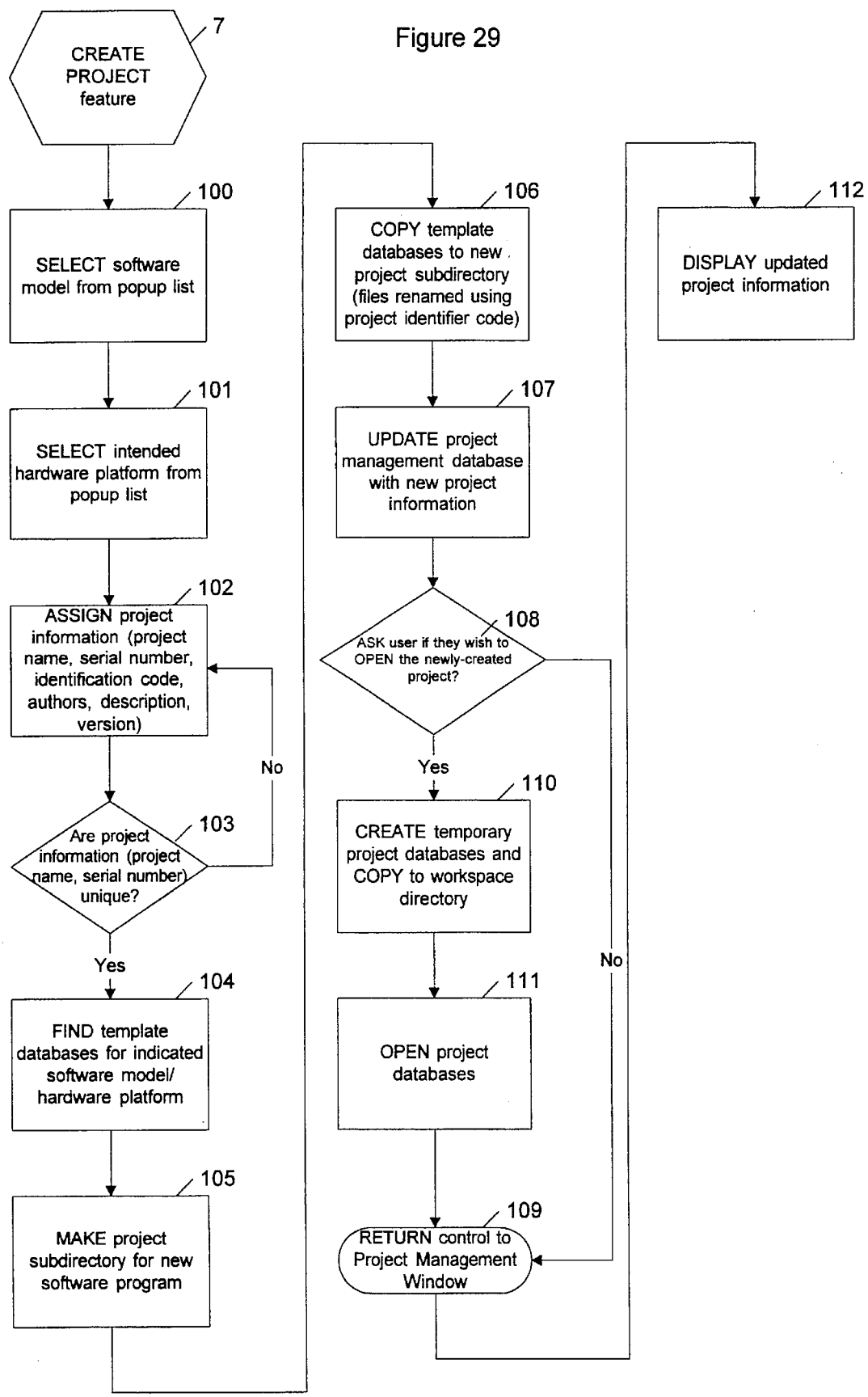
FIG. 29 shows a flow diagram of the Project Creating feature of the present invention.

Referring to FIG. 29, an example of the process for creating a project using the system of the present invention is described. Creating a project will set up a subdirectory for the project such that data management and tracking is simplified. The software model is first selected 100 from the pop-up list presented to the user. The intended hardware platform is then also selected 101 from the pop-up list. Project information, such as a project name, serial number, identification code, names of authors, a short description of the project, and a version number, will then have names and/or values assigned 102 by the user.

At this point, the project information is checked against information assigned to existing projects 103. If the project information is the same as previously entered project information, the user must reassign project information for the new project. If the new project information is unique, the system will next find 104 the template databases for the indicated software model and hardware platform. The system will then create 105 a project subdirectory for the new software program and copy 106 the template databases to the new project subdirectory. The files may be renamed at this point according to a project identifier code.

The project management database is then updated 107 with the new project information. Thus, any useful information generated by this project can be tracked and utilized by other projects. Now that the new project is set up, the user is then queried 108 as to whether he or she wants to open the newly created project. If the user merely wanted to set up the project and will return to work on it at a later time, control is returned 109 to the Project Management window. If the project is opened, temporary project databases are created and copied 110 to a workspace directory. The project databases are then opened 111. When work on the project for that session is complete, control is returned 109 to the Project Management window. The system display may be updated 112 to reflect the new project.

Figure 30:
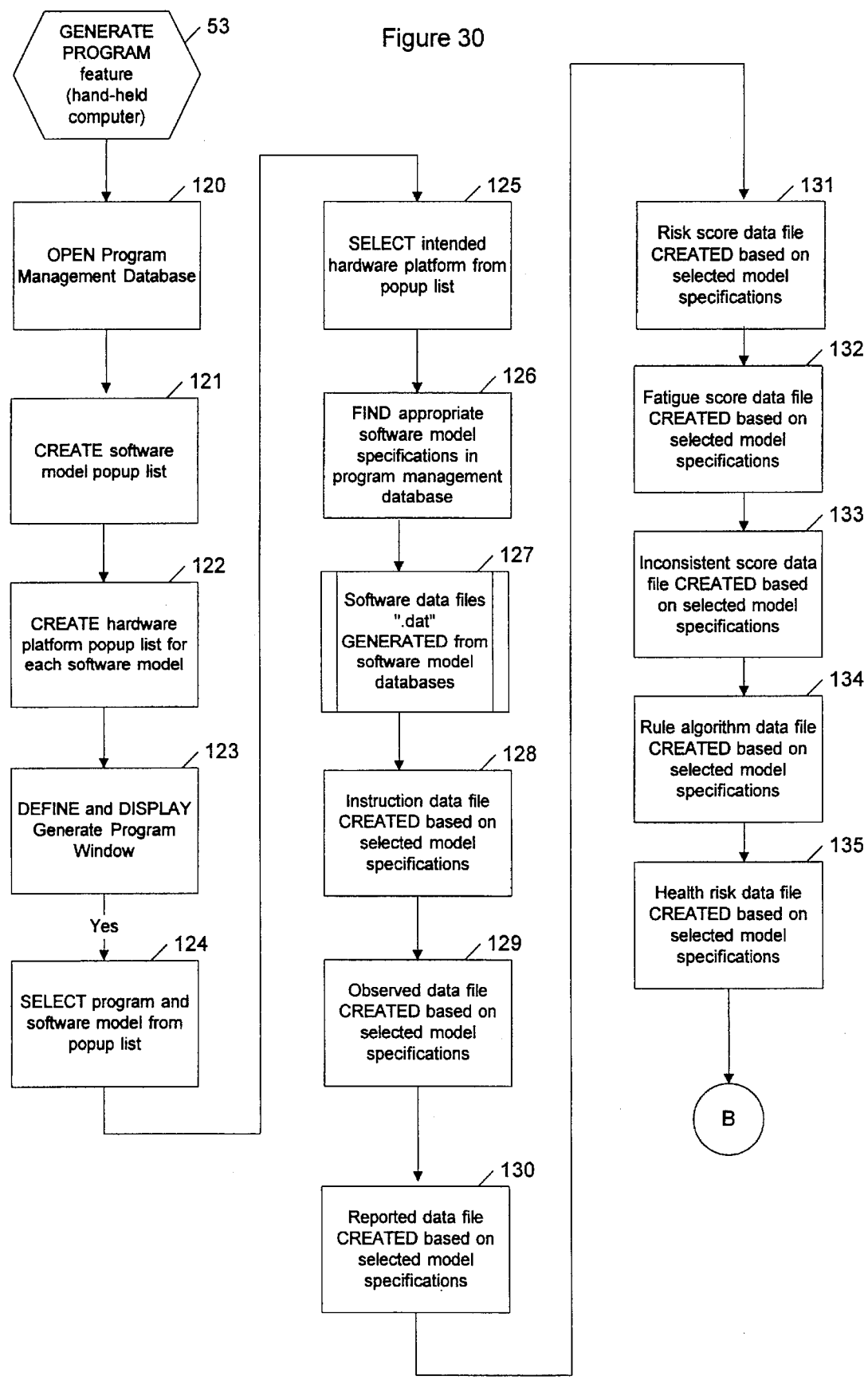
FIGS. 30 and 31 show a flow diagram of the software generation feature of the present invention.
Figure 31:
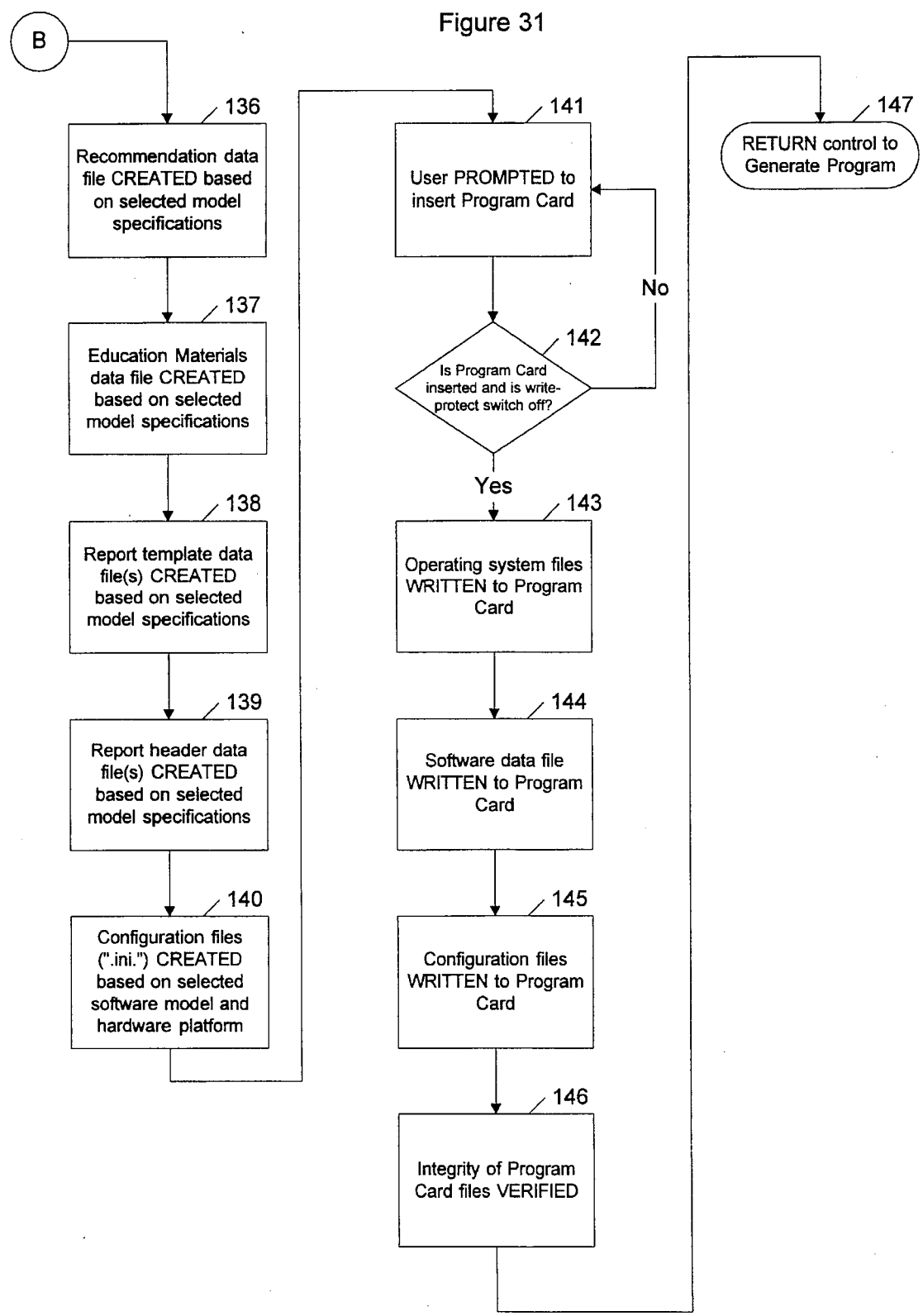
Figure 32:
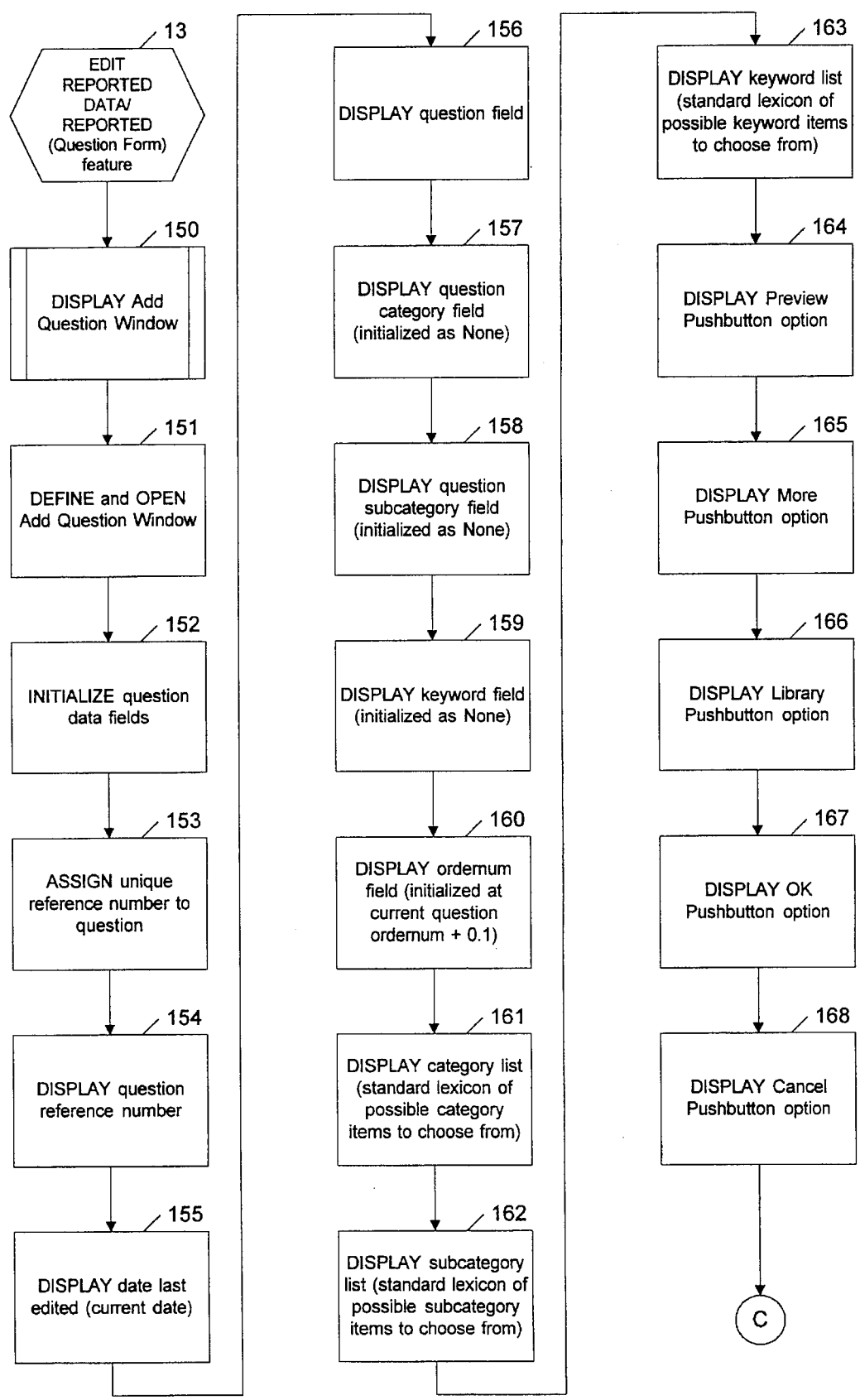
FIGS. 32–39 show a flow diagram of the Edit Reported Data/Reported (Question Form) process.
Figure 33:
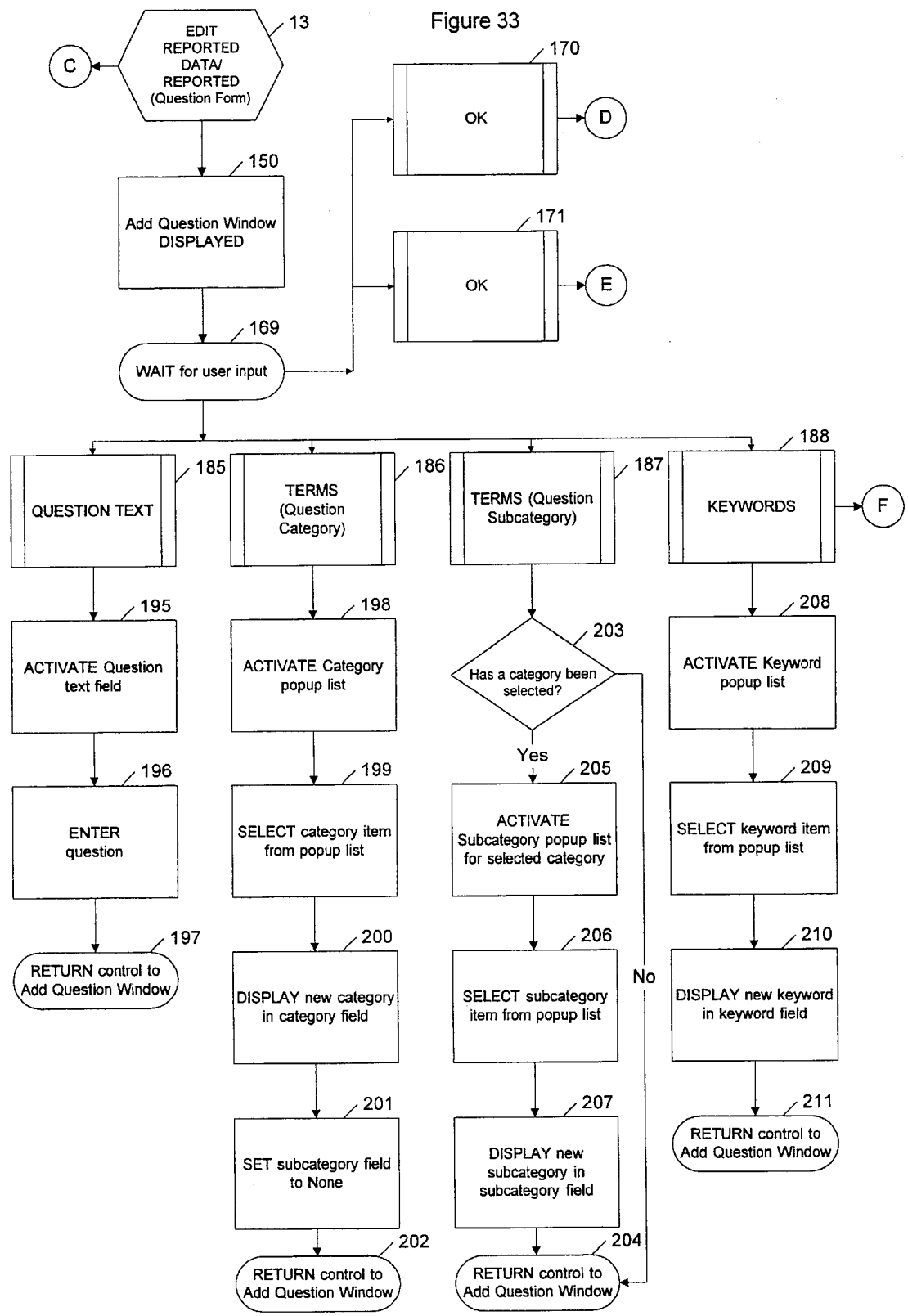
Figure 34:
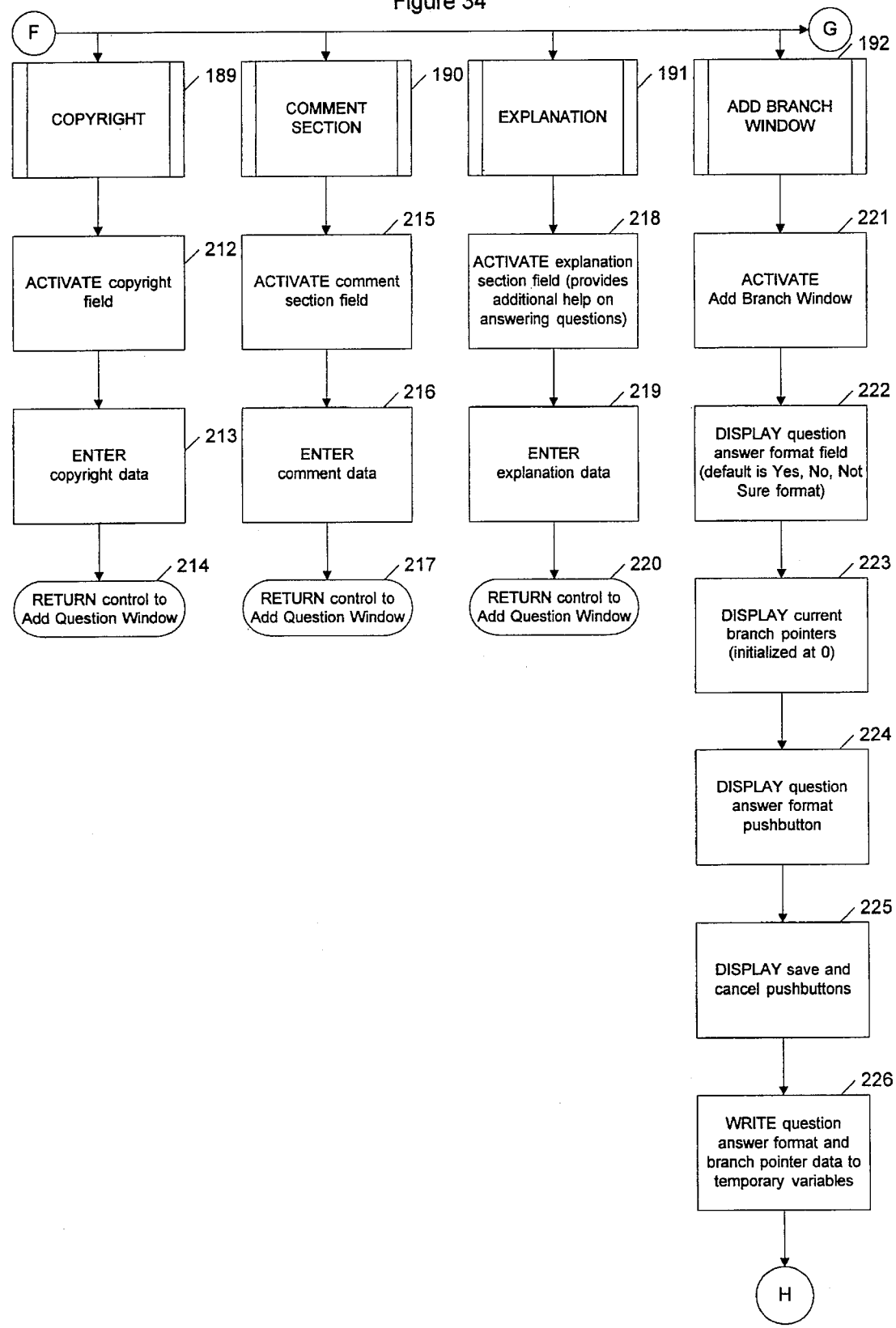
Figure 35:
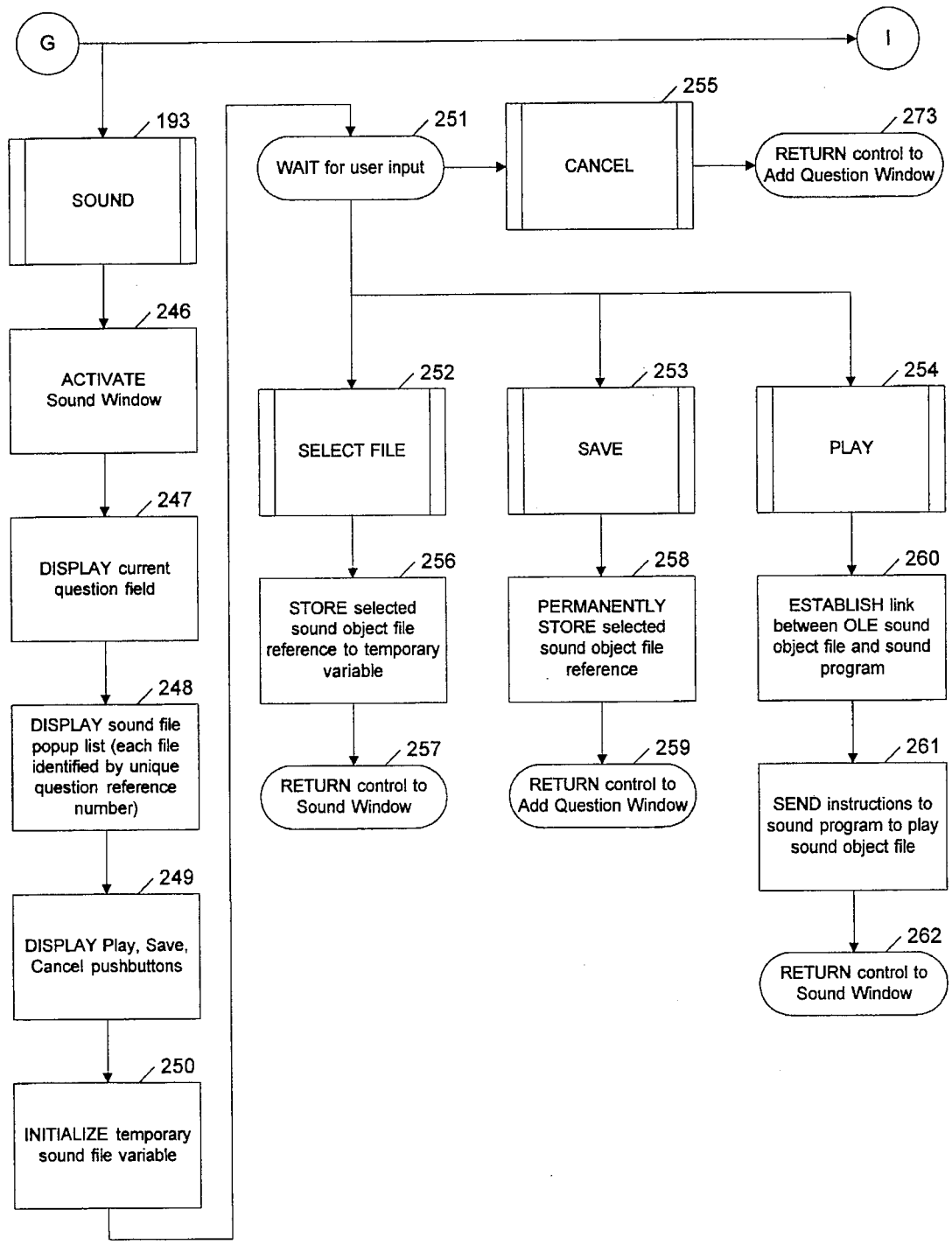
Figure 36:
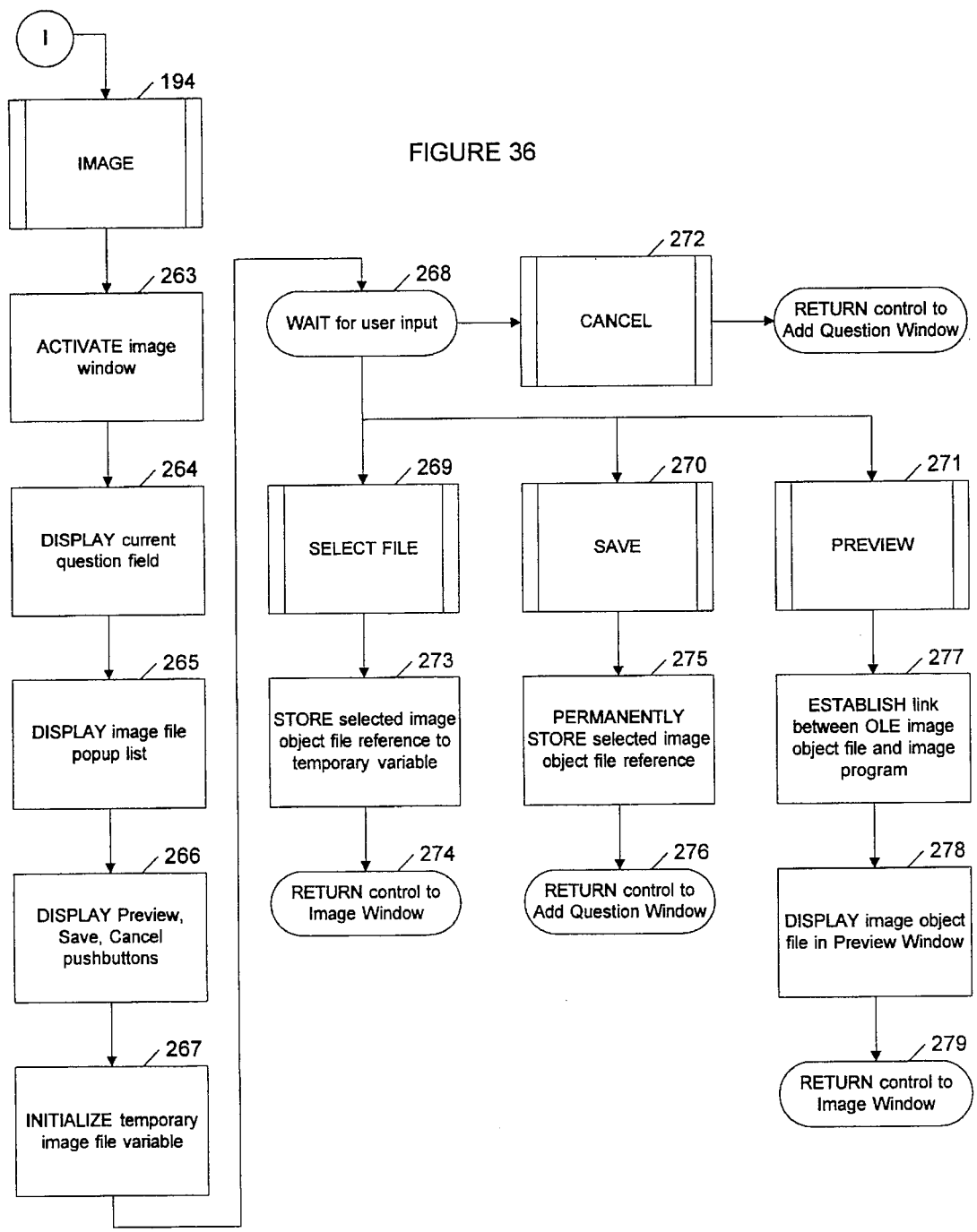
Figure 37:
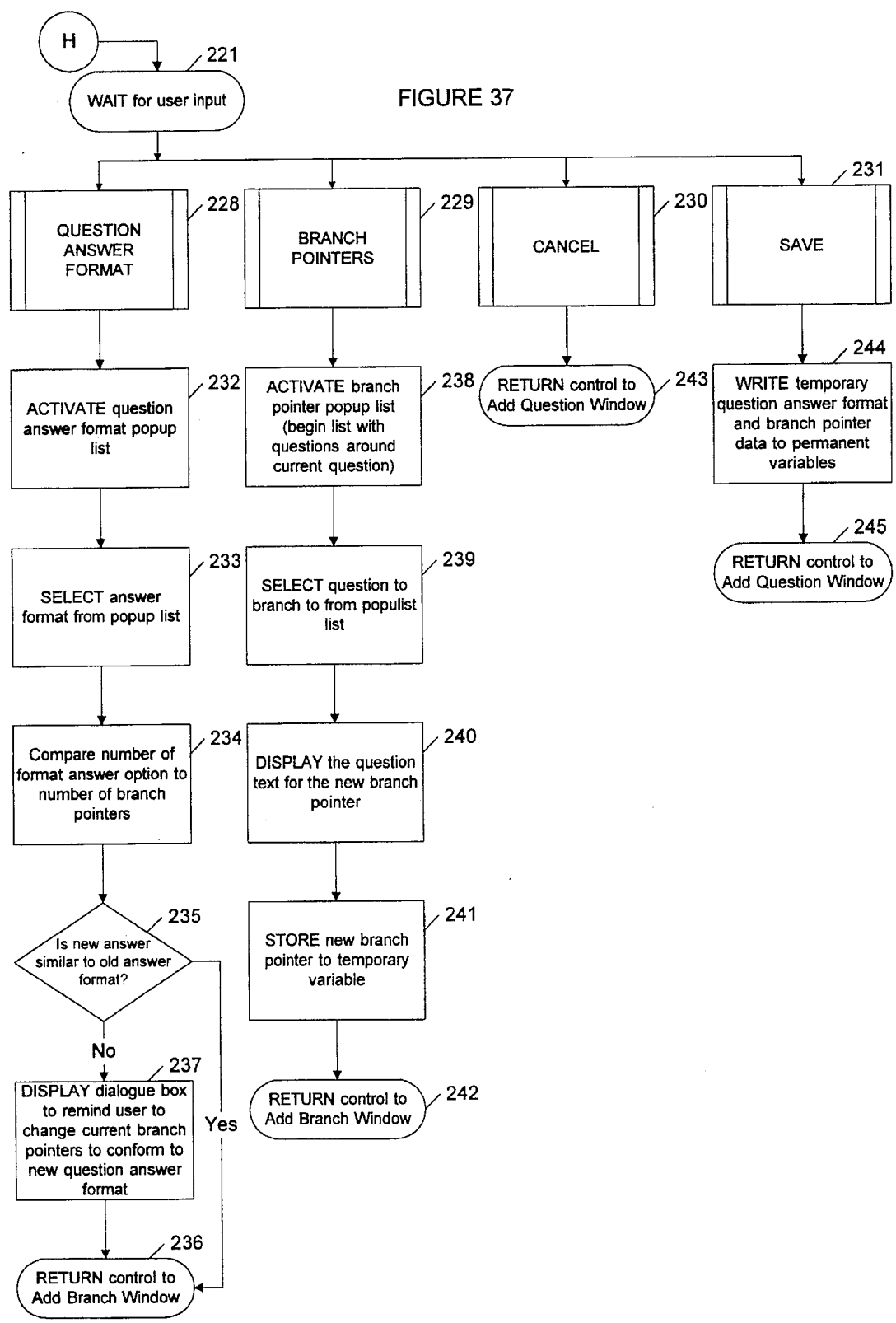
Figure 38:
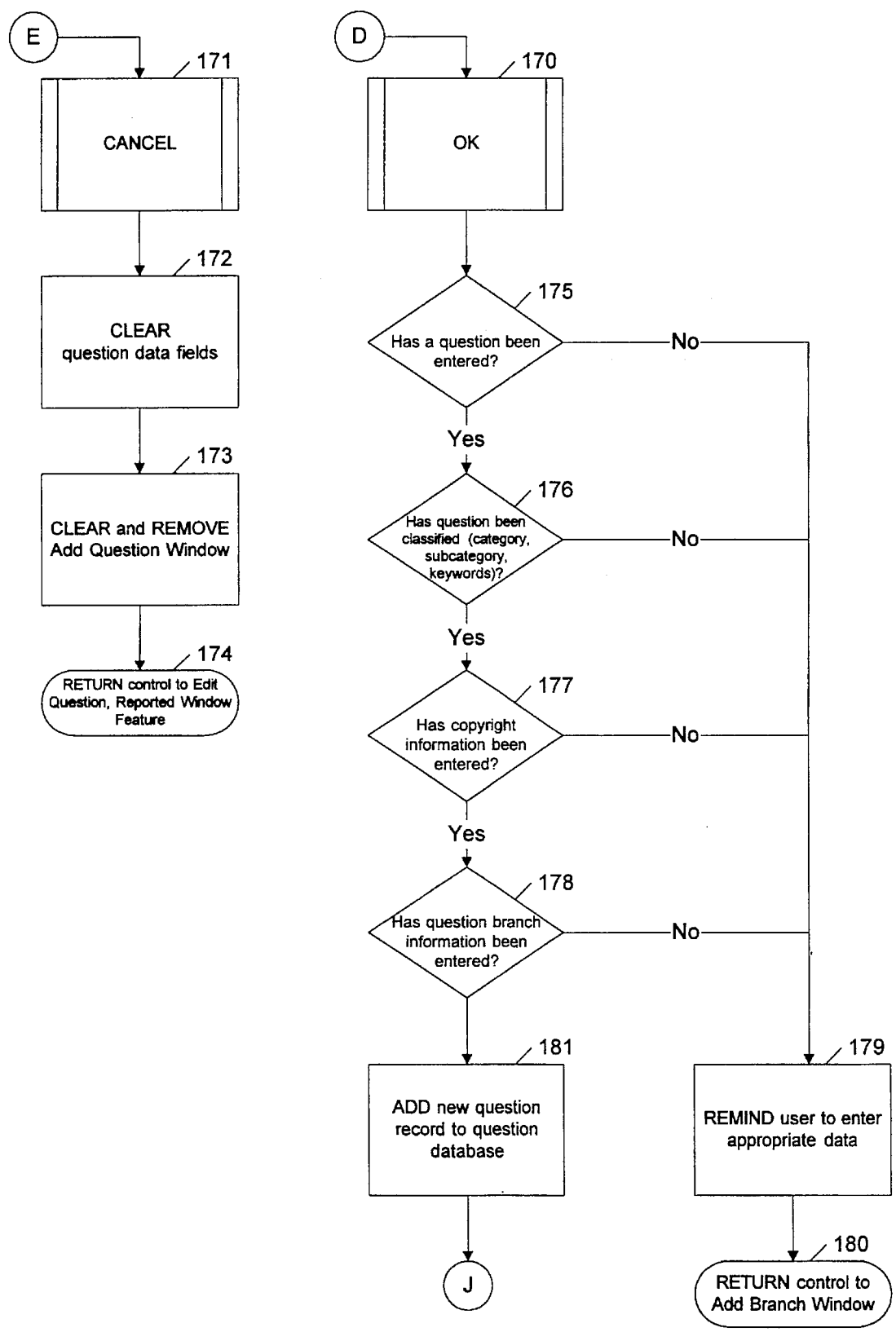
Figure 39:
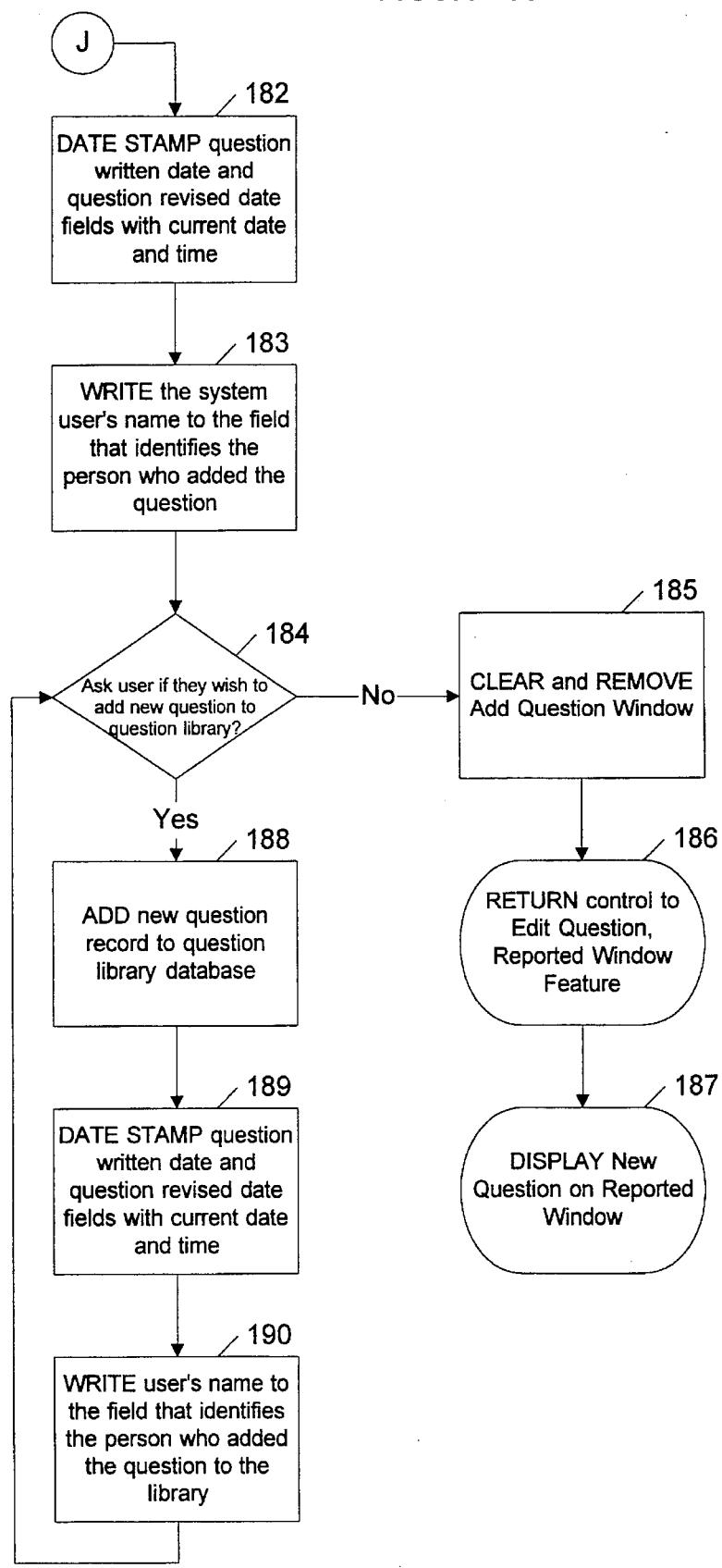
Figure 40:
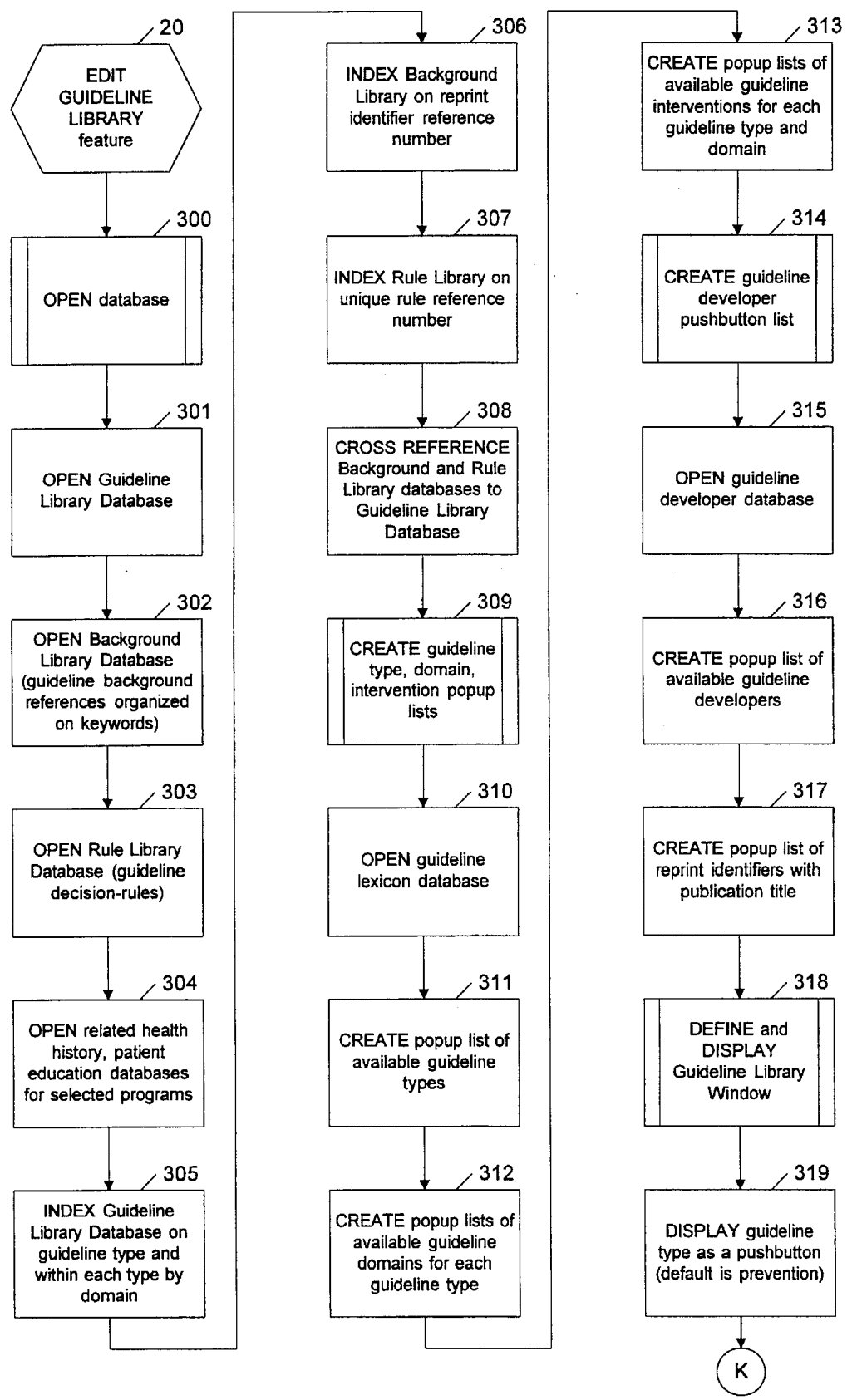
FIGS. 40–52 show a flow diagram of the Edit Guideline Library process.
Figure 41:
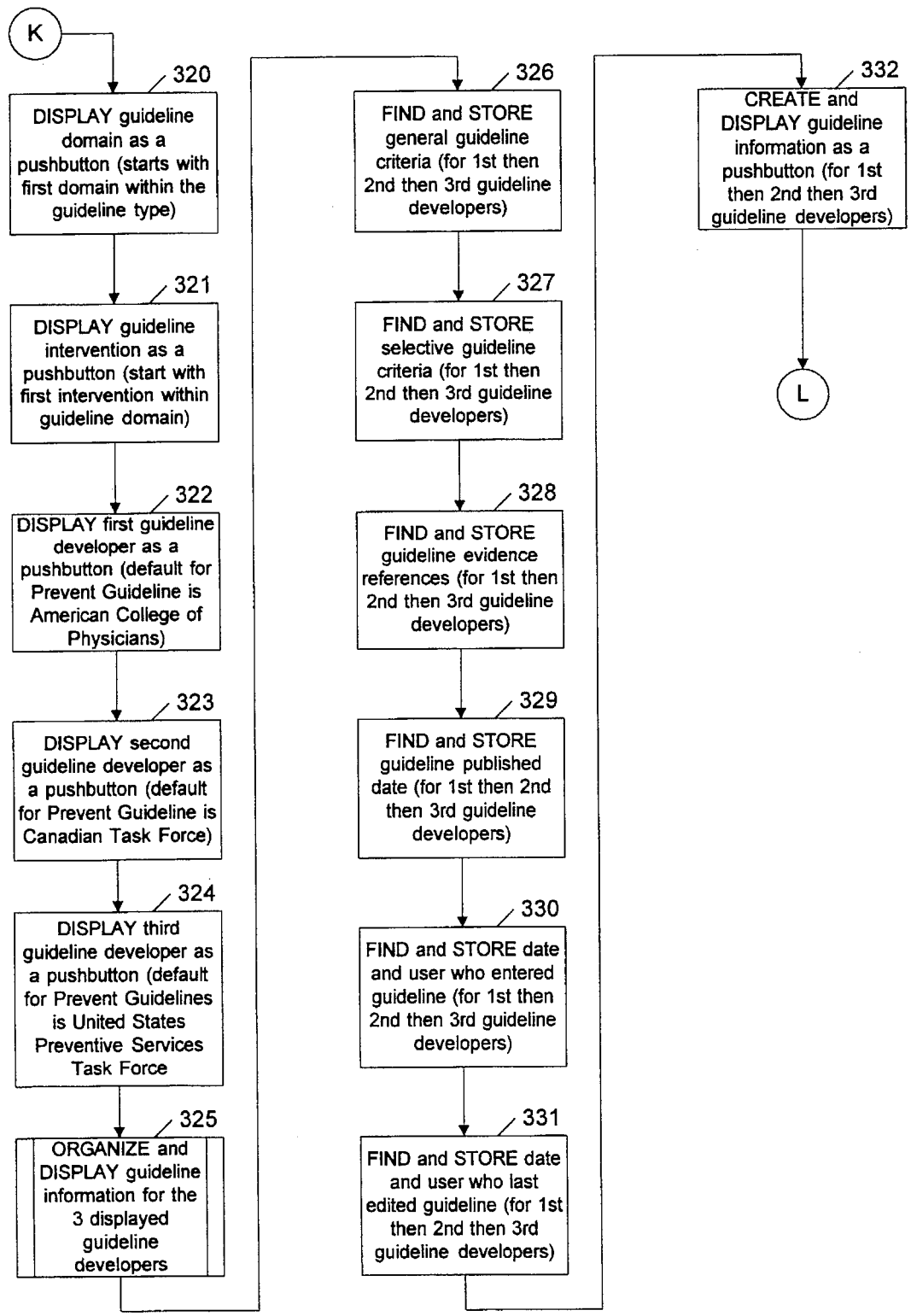
Figure 42:
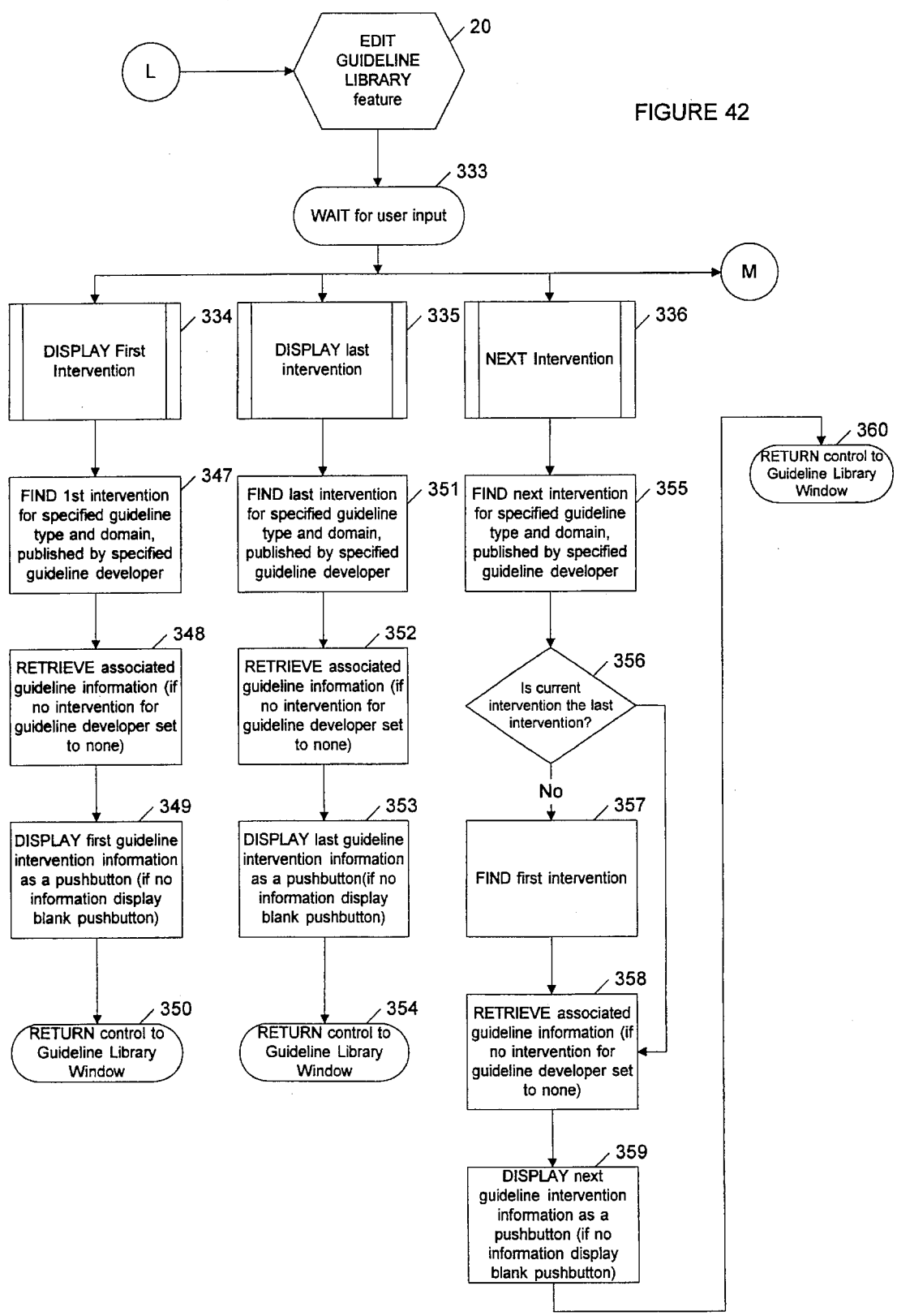
Figure 43:
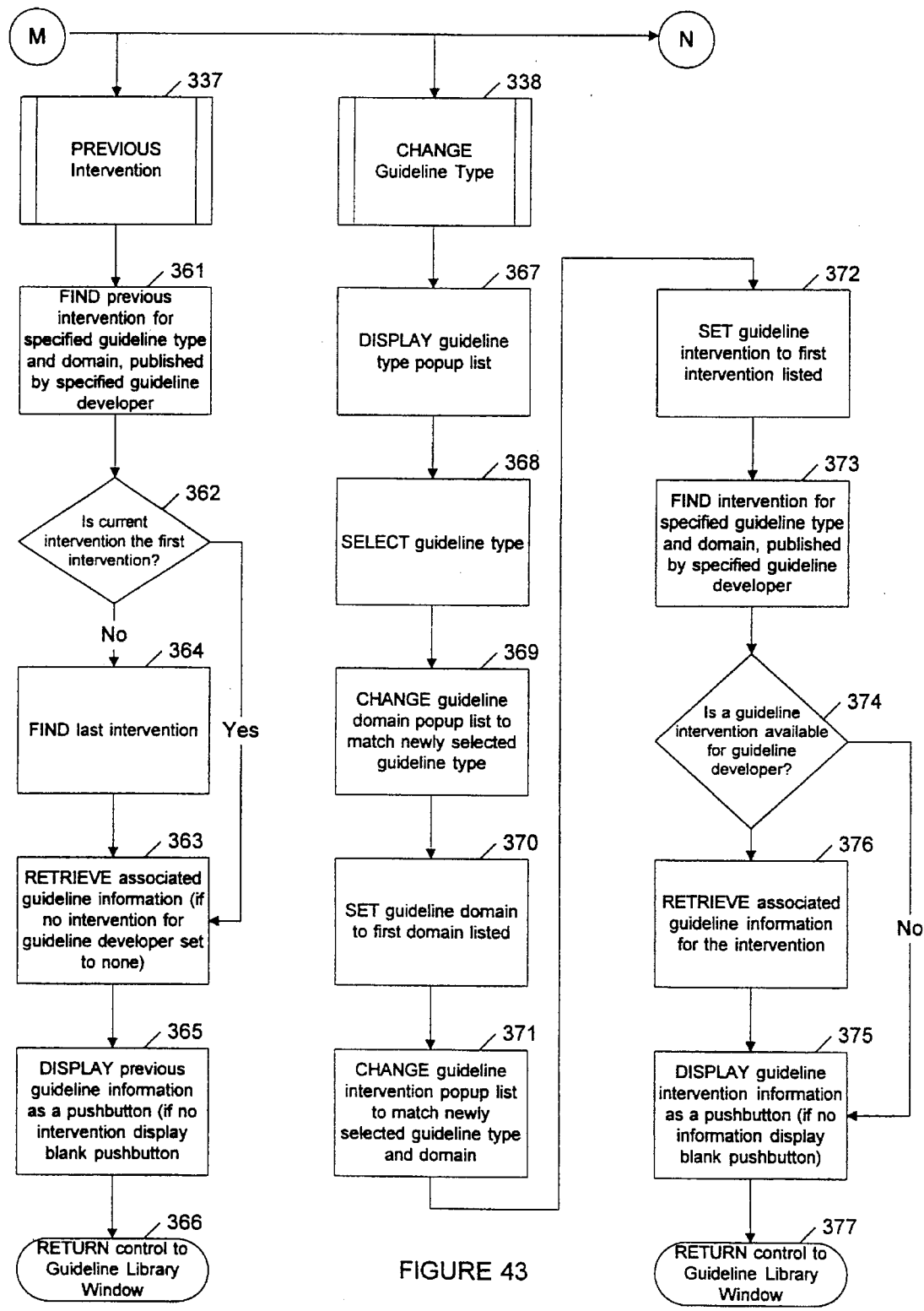
Figure 44:
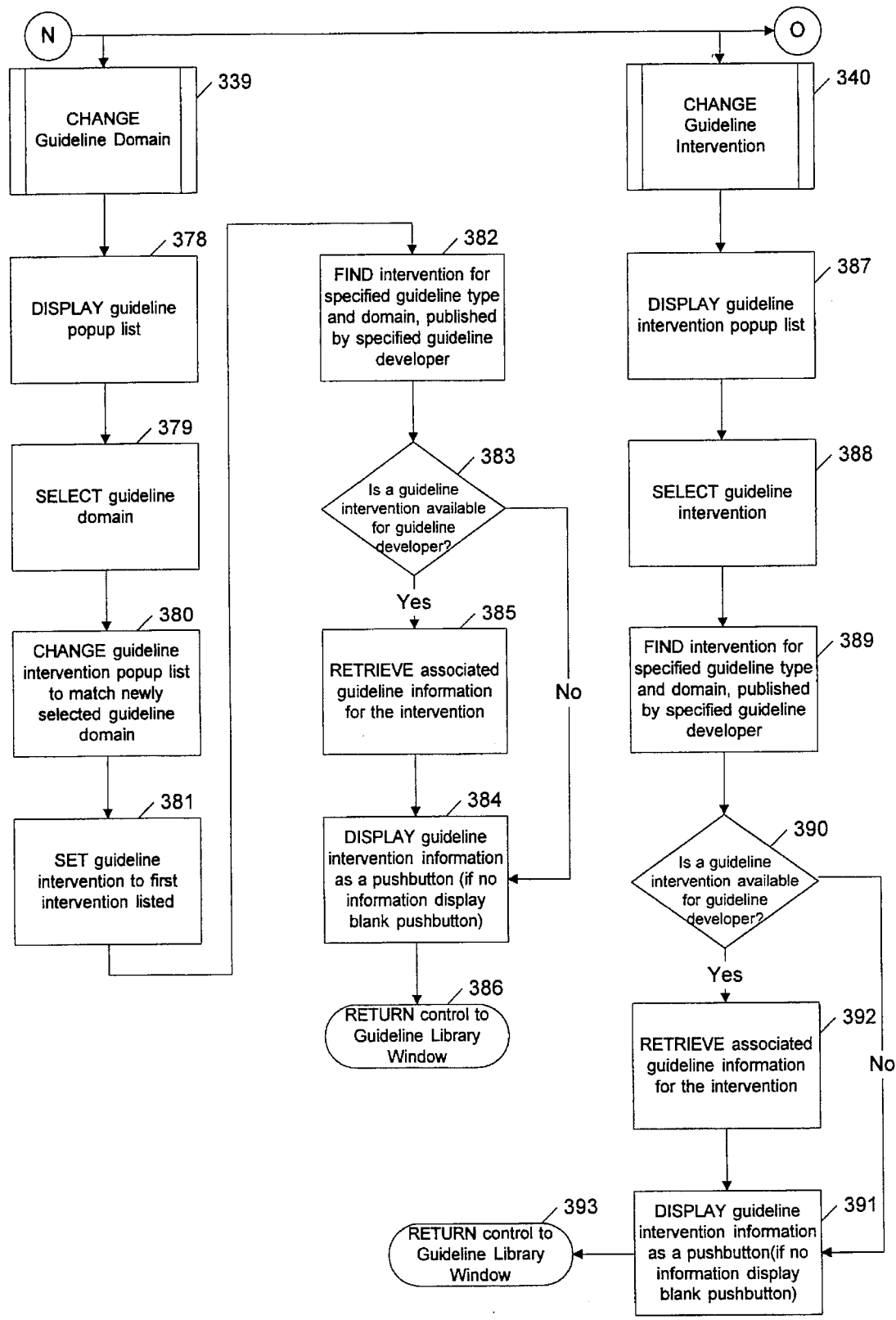
Figure 45:
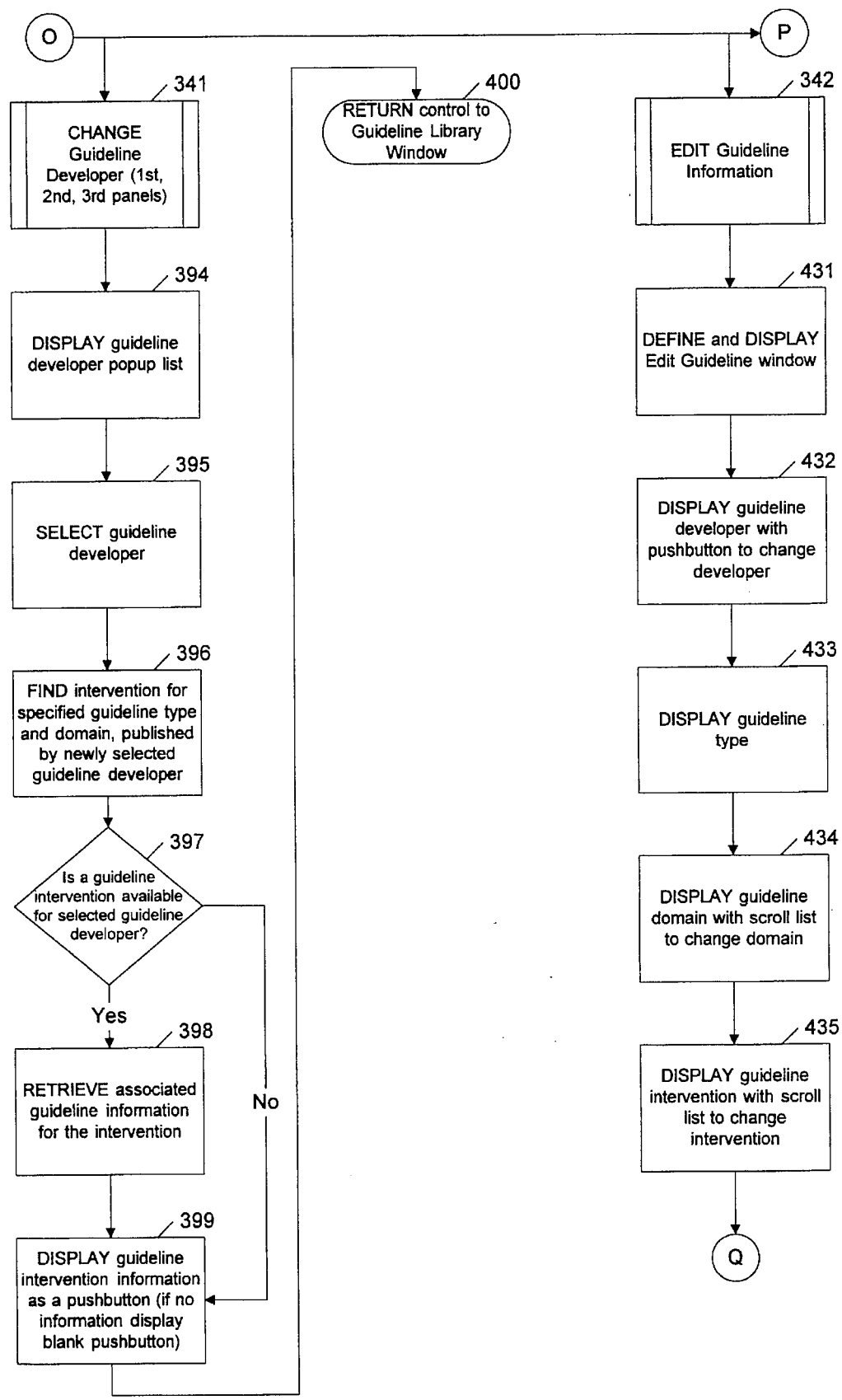
Figure 46:
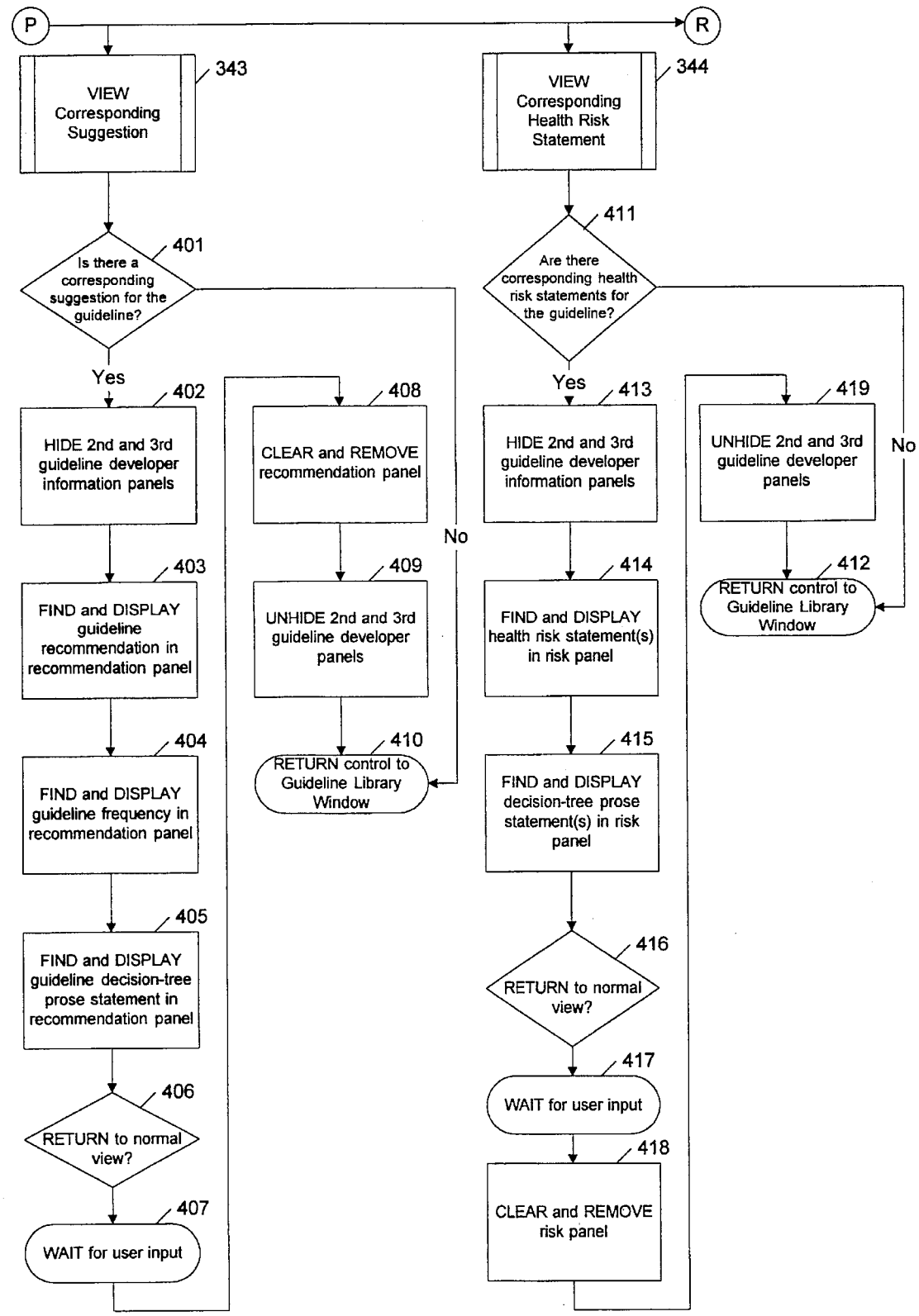
Figure 47:
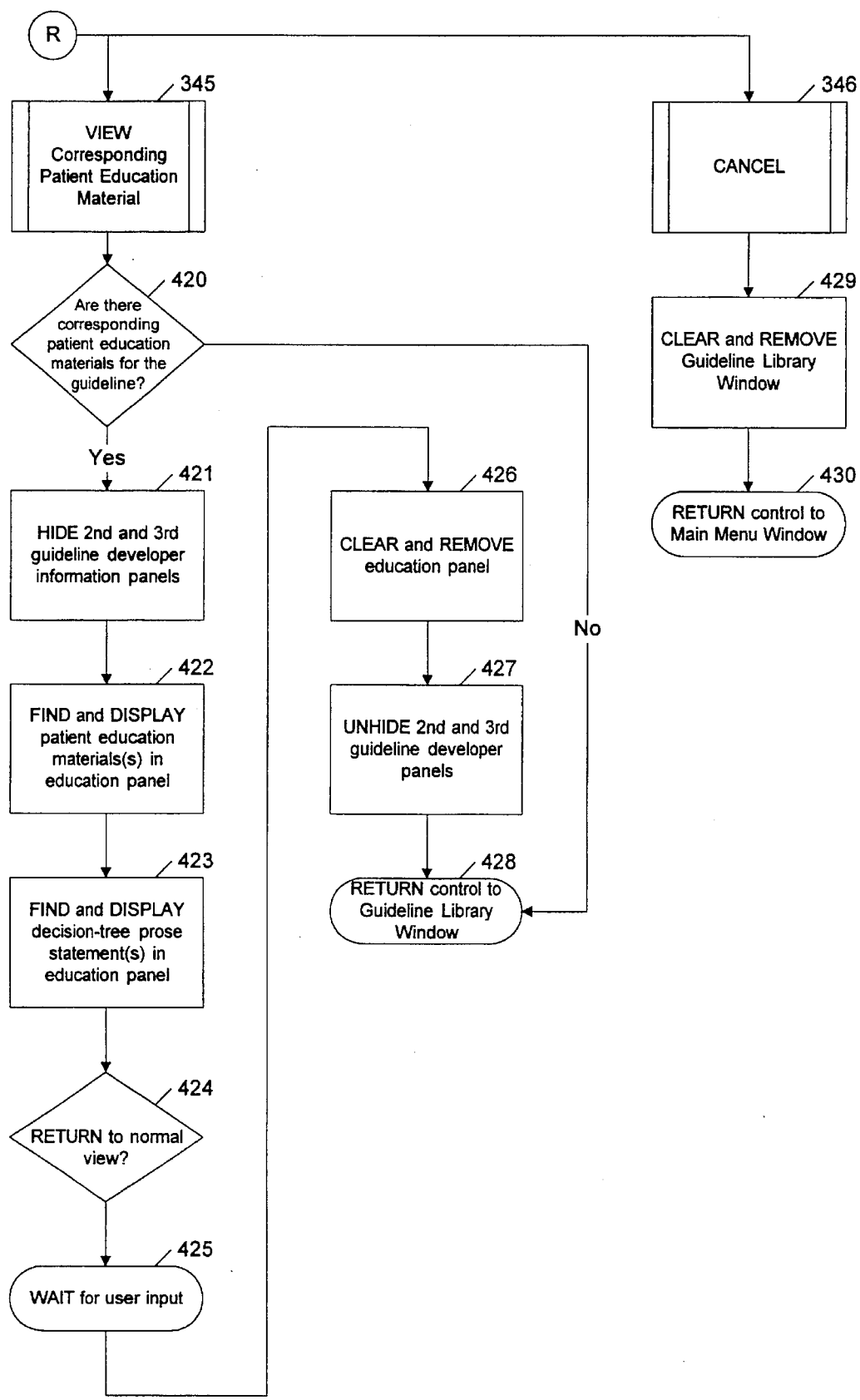
Figure 48:
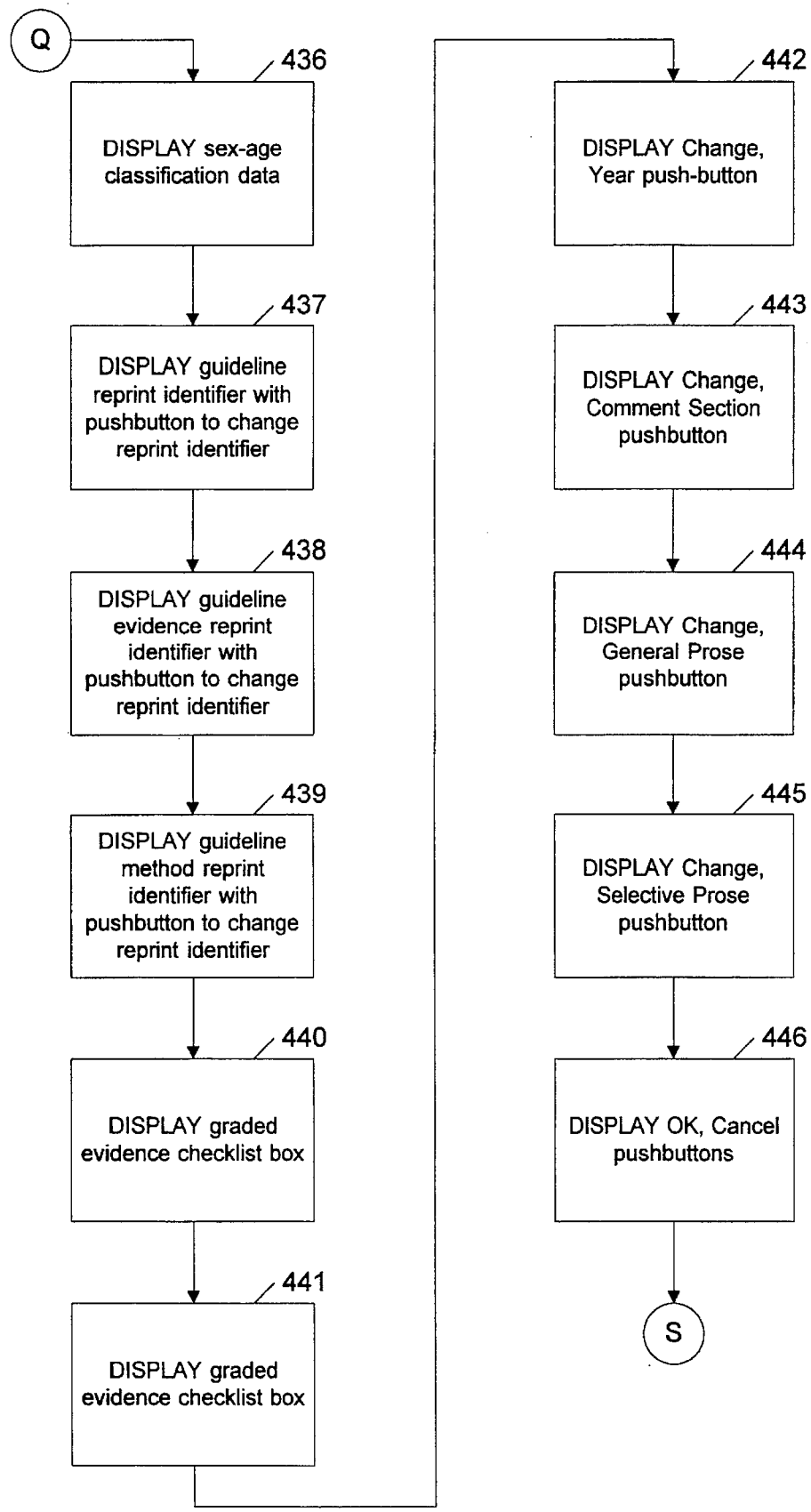
Figure 49:
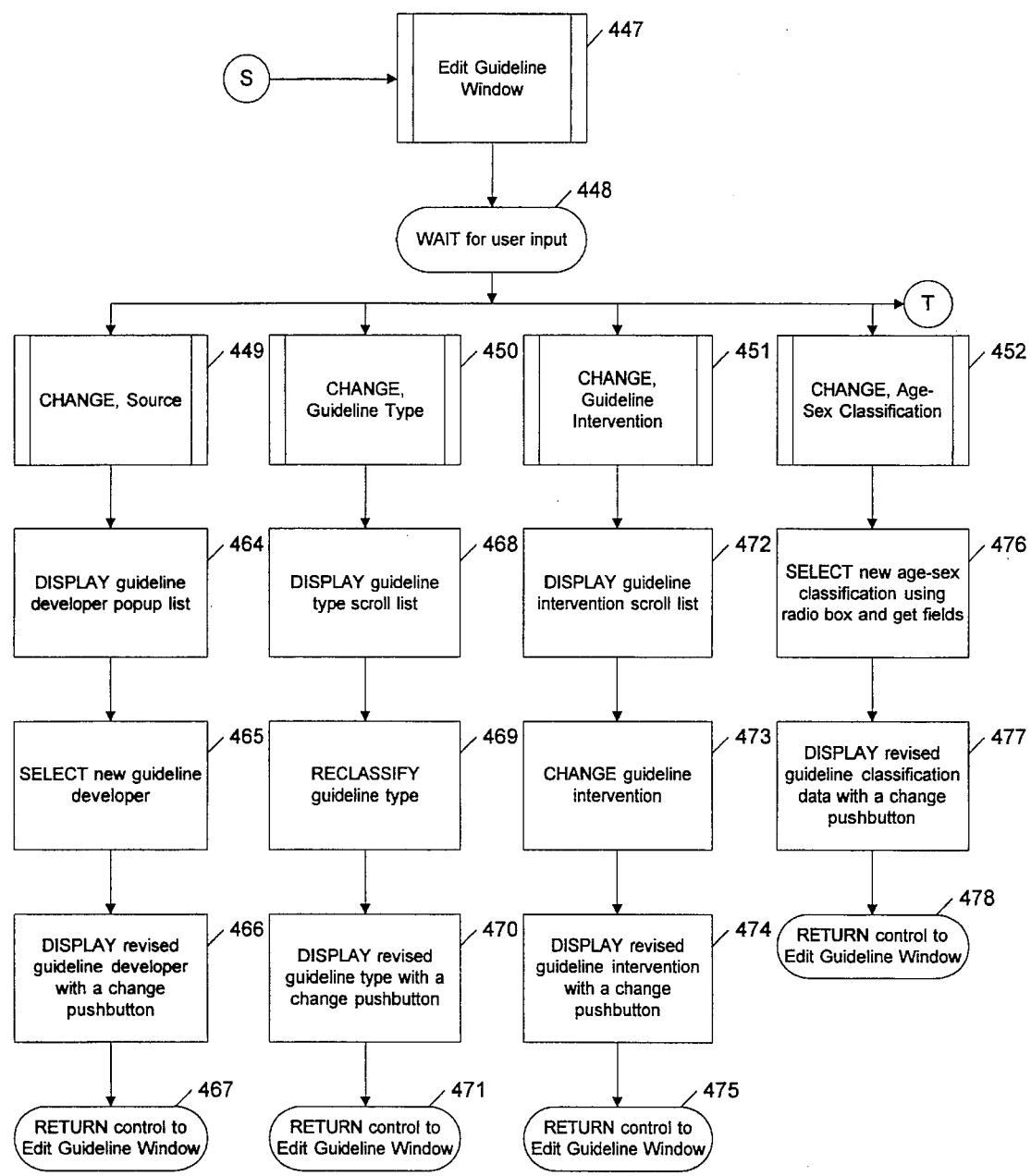
Figure 50:
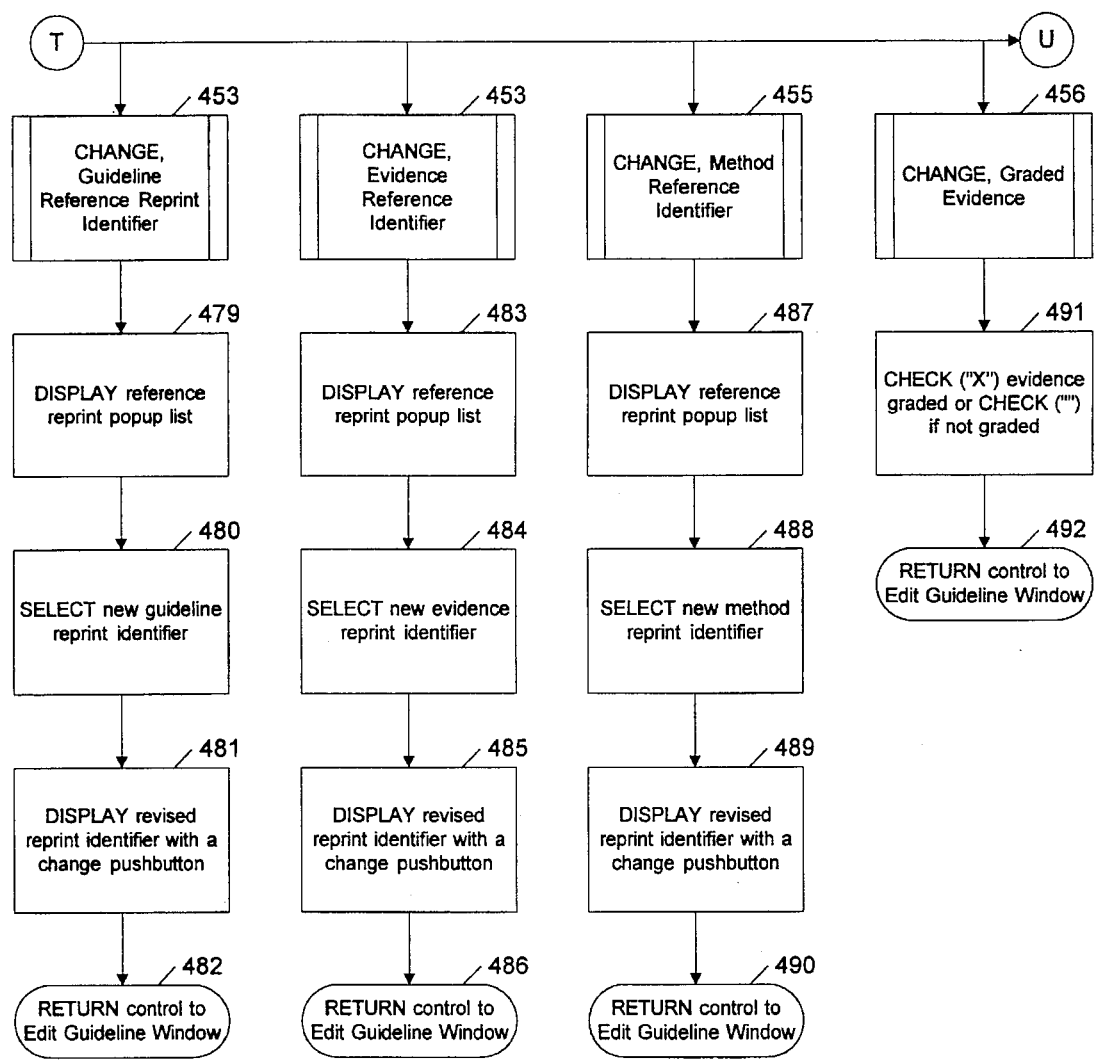
Figure 51:
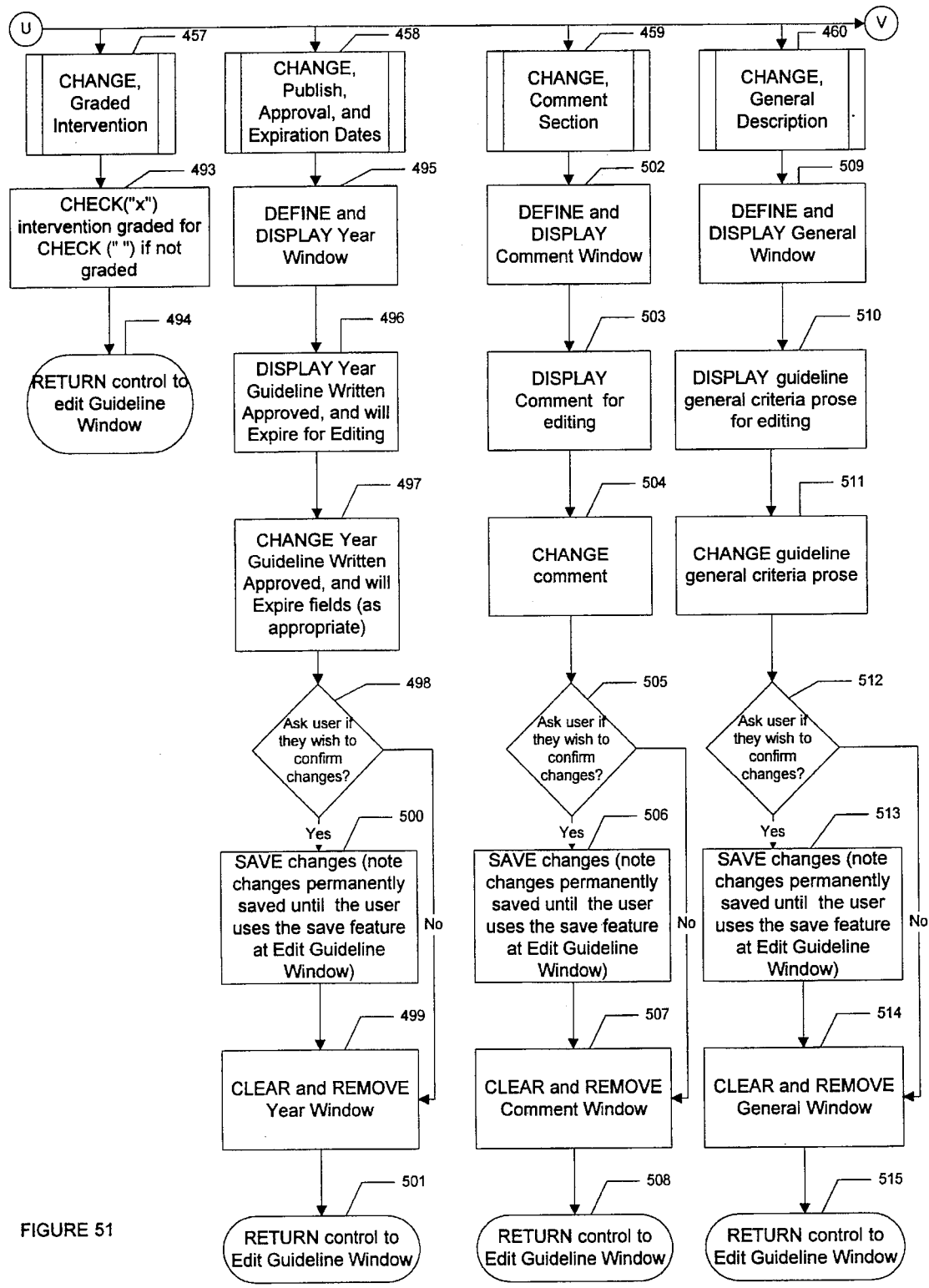
Figure 52:
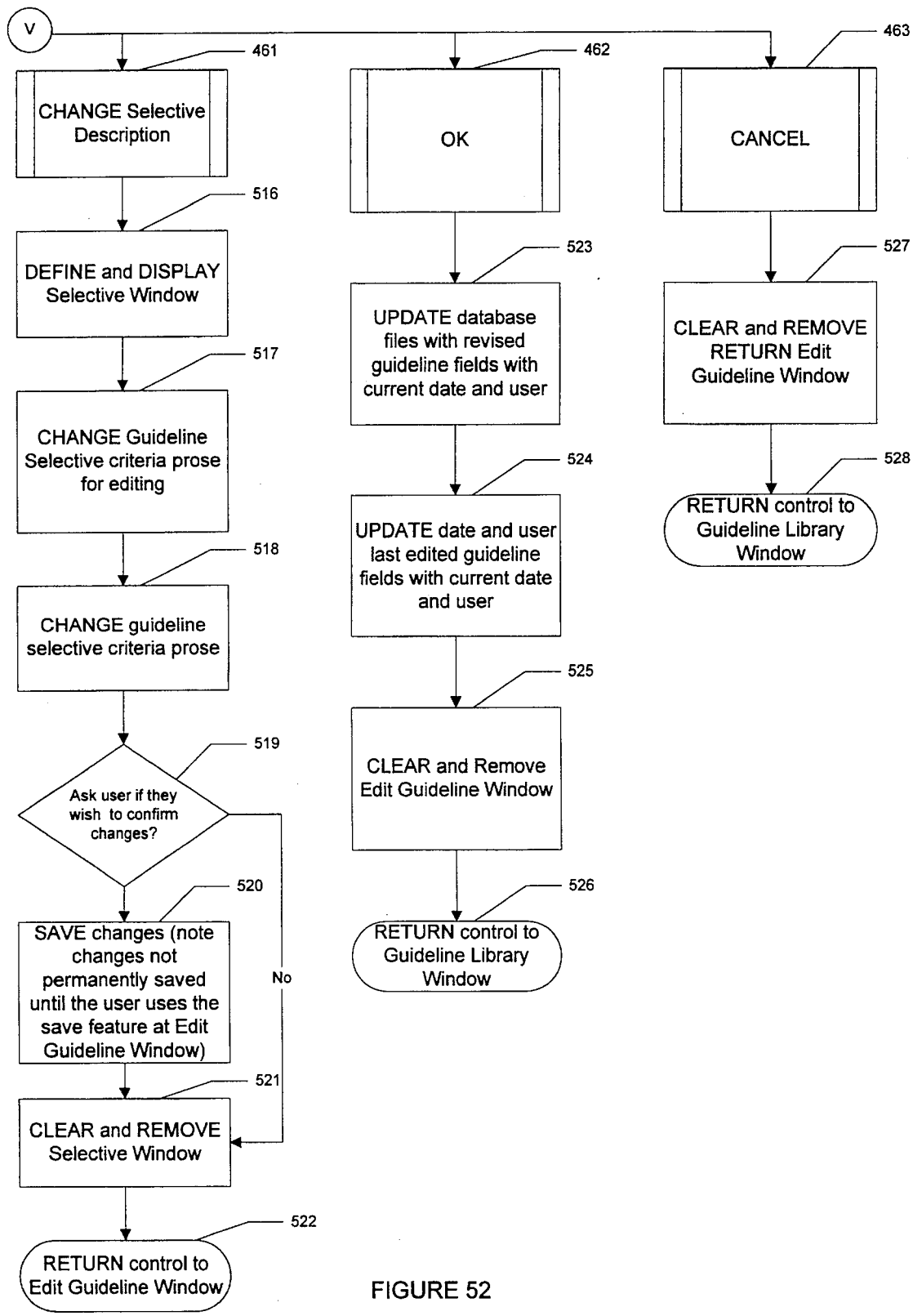
Figure 53:
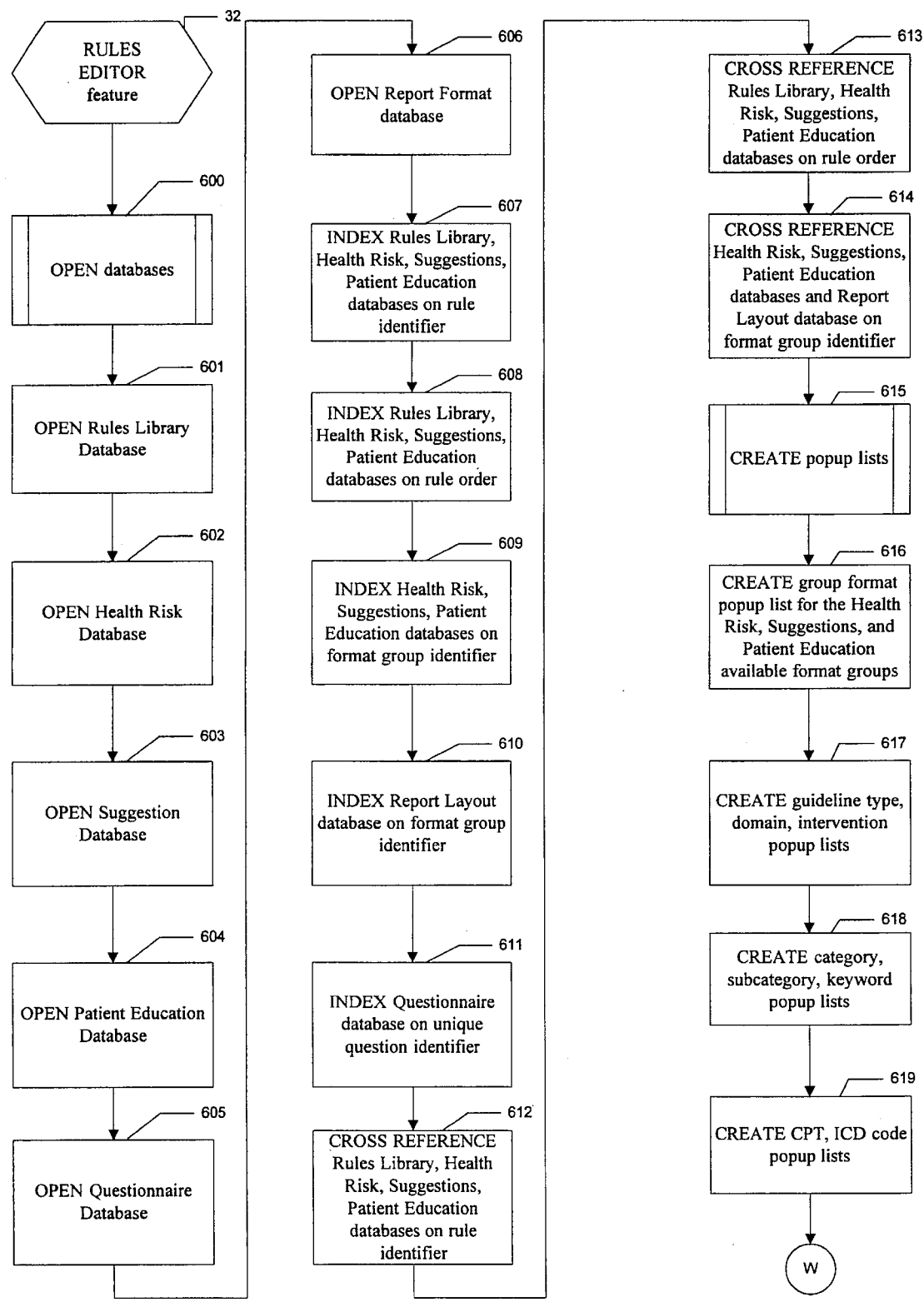
FIGS. 53–75 show a flow diagram of the Rules Editor feature.
Figure 54:
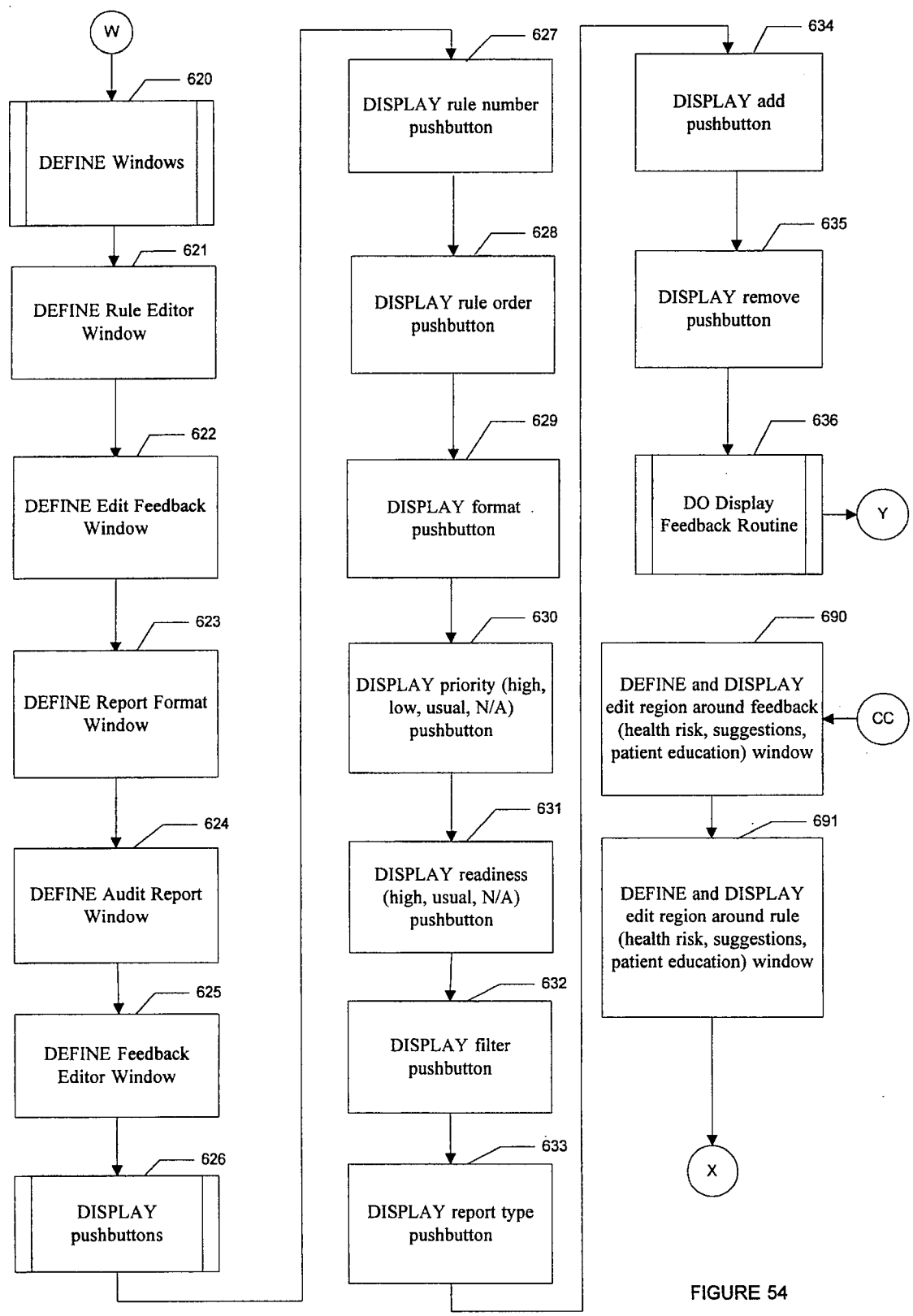
Figure 55:
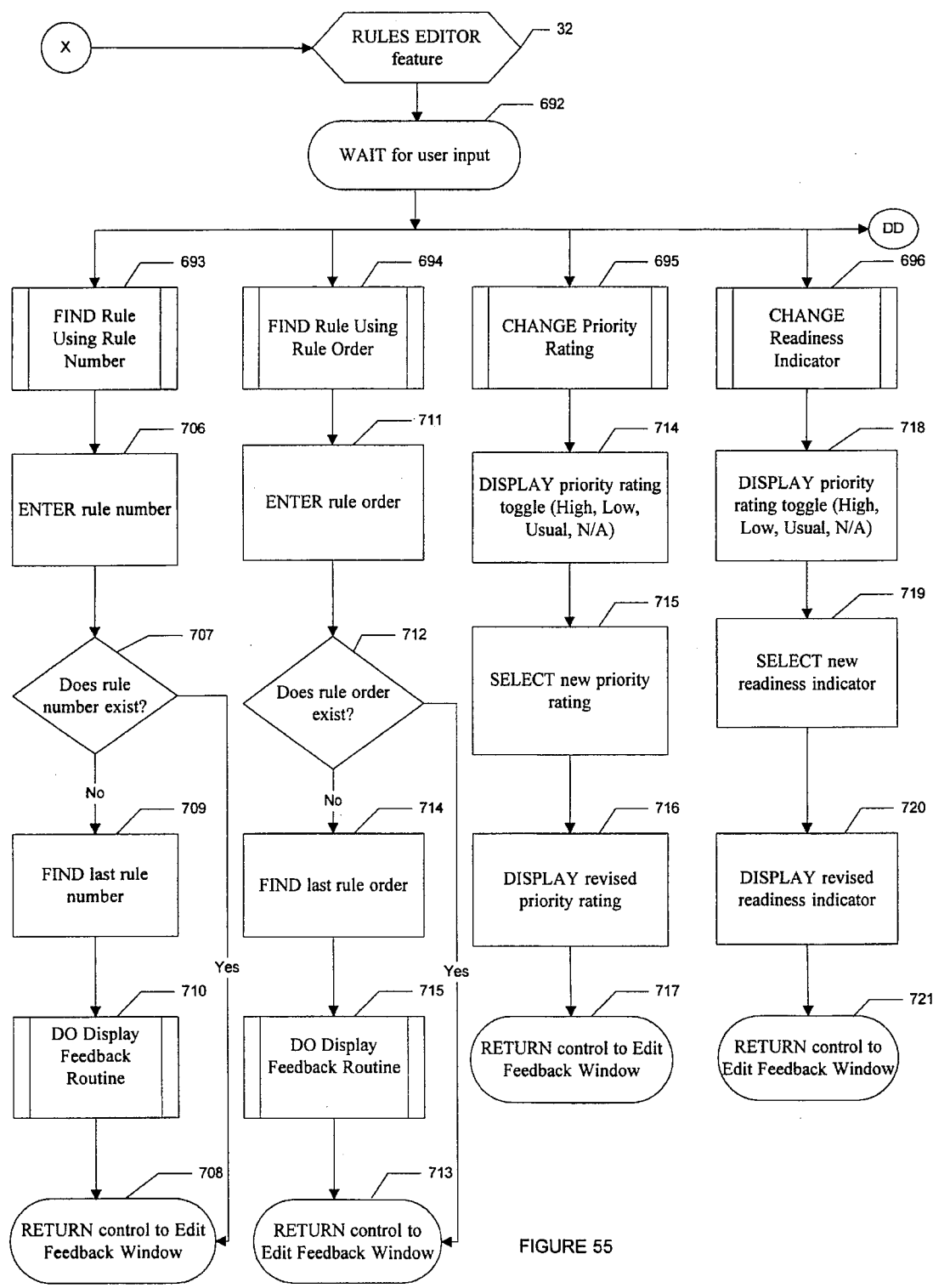
Figure 56:
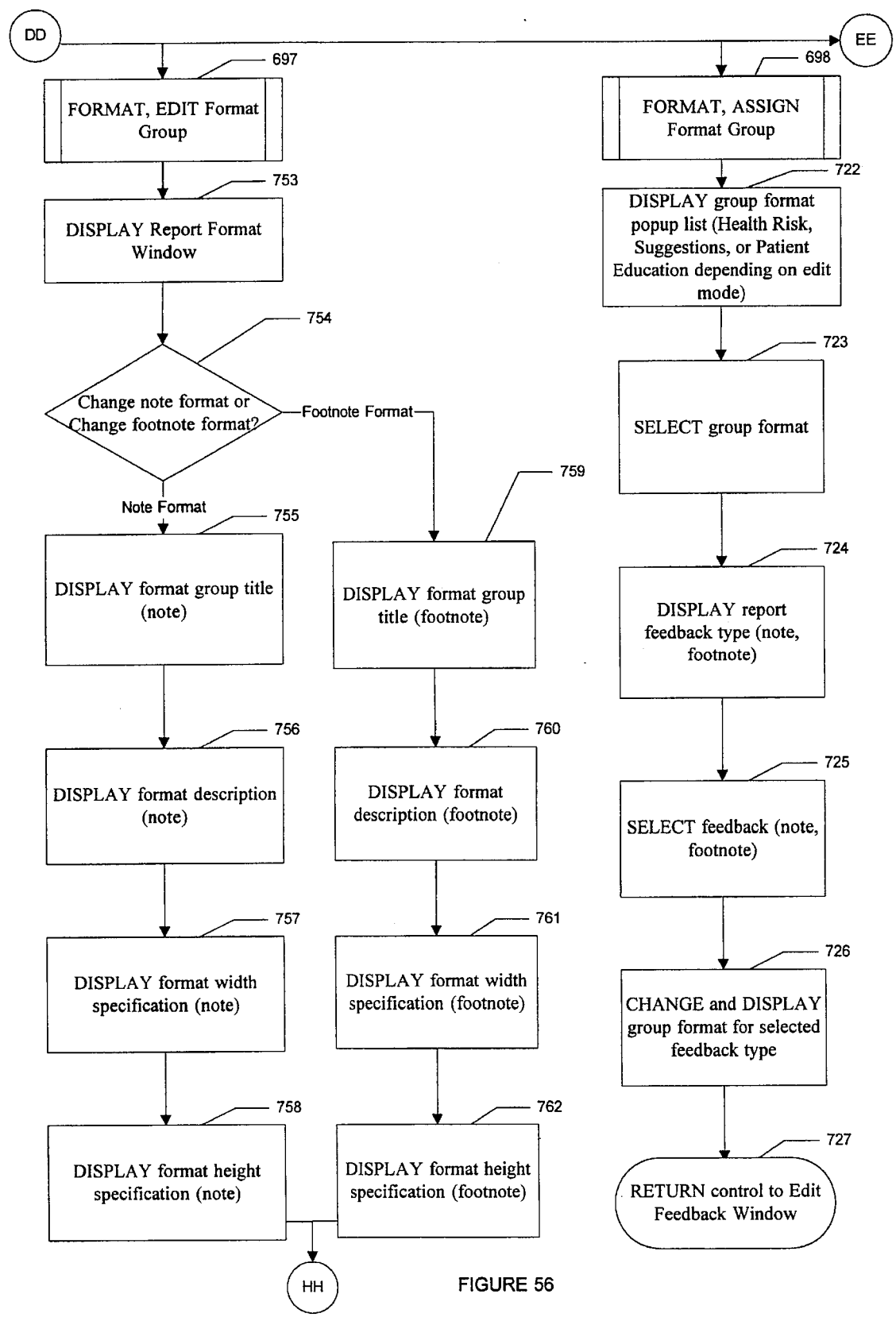
Figure 57:
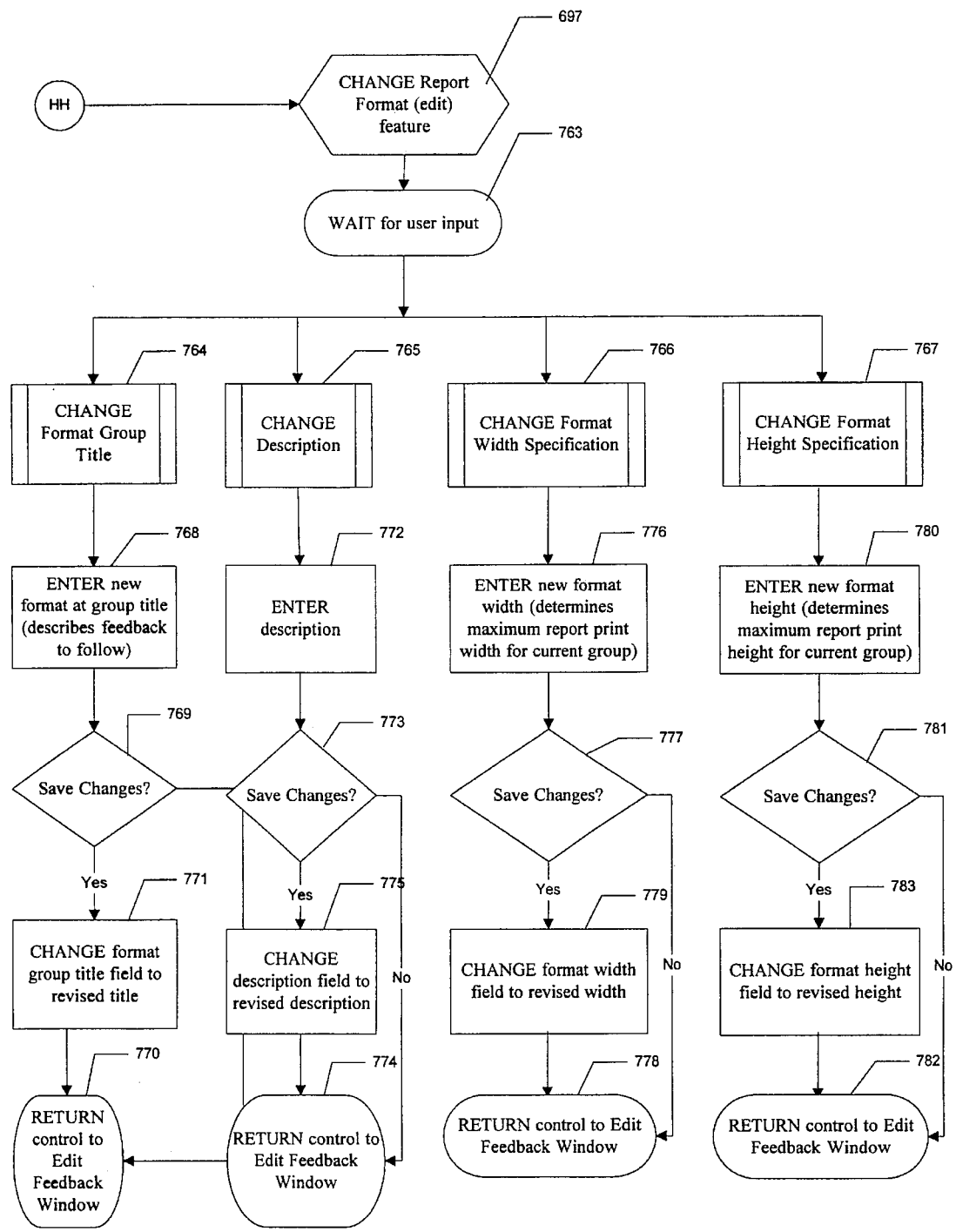
Figure 58:
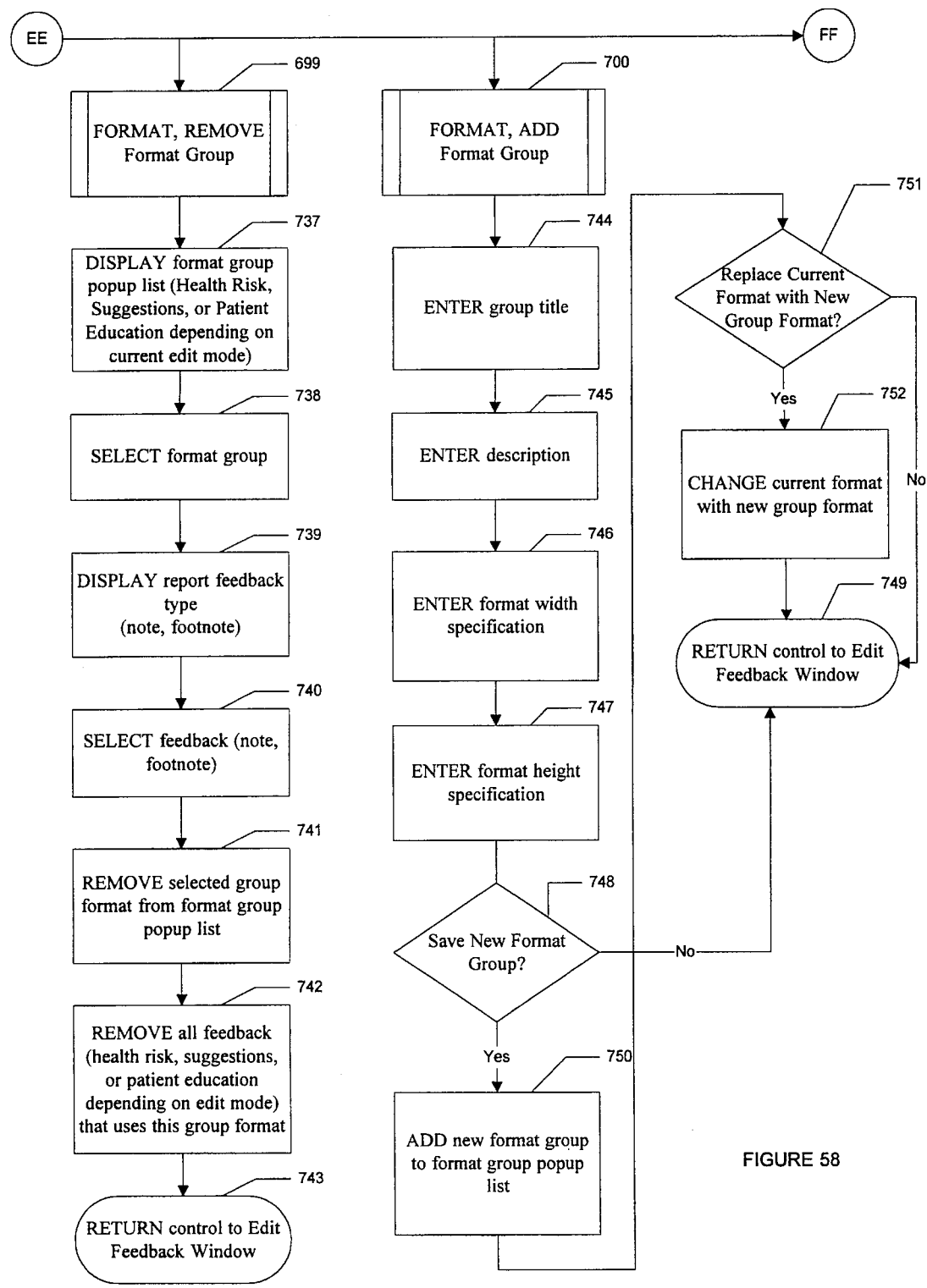
Figure 59:
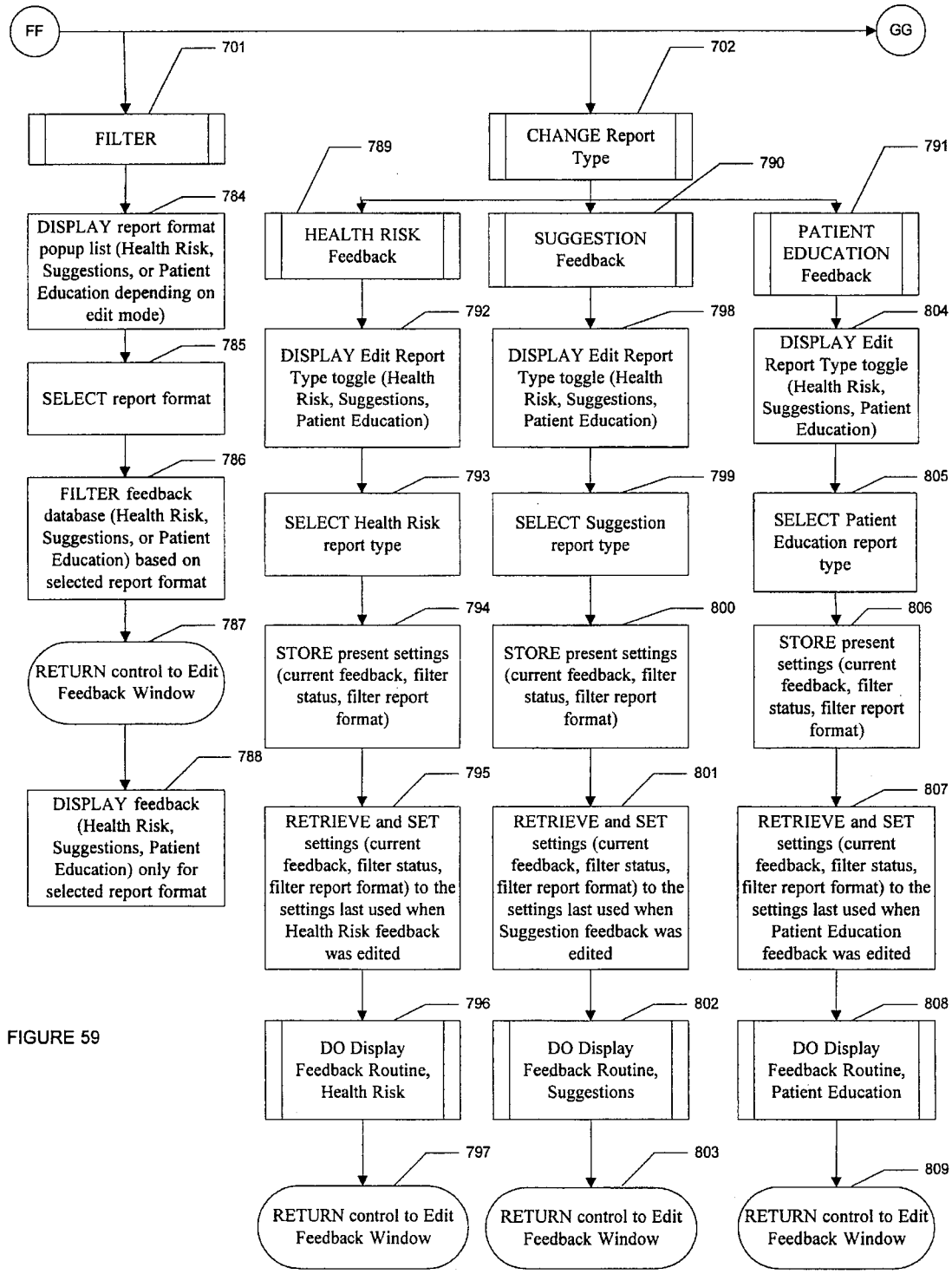
Figure 60:
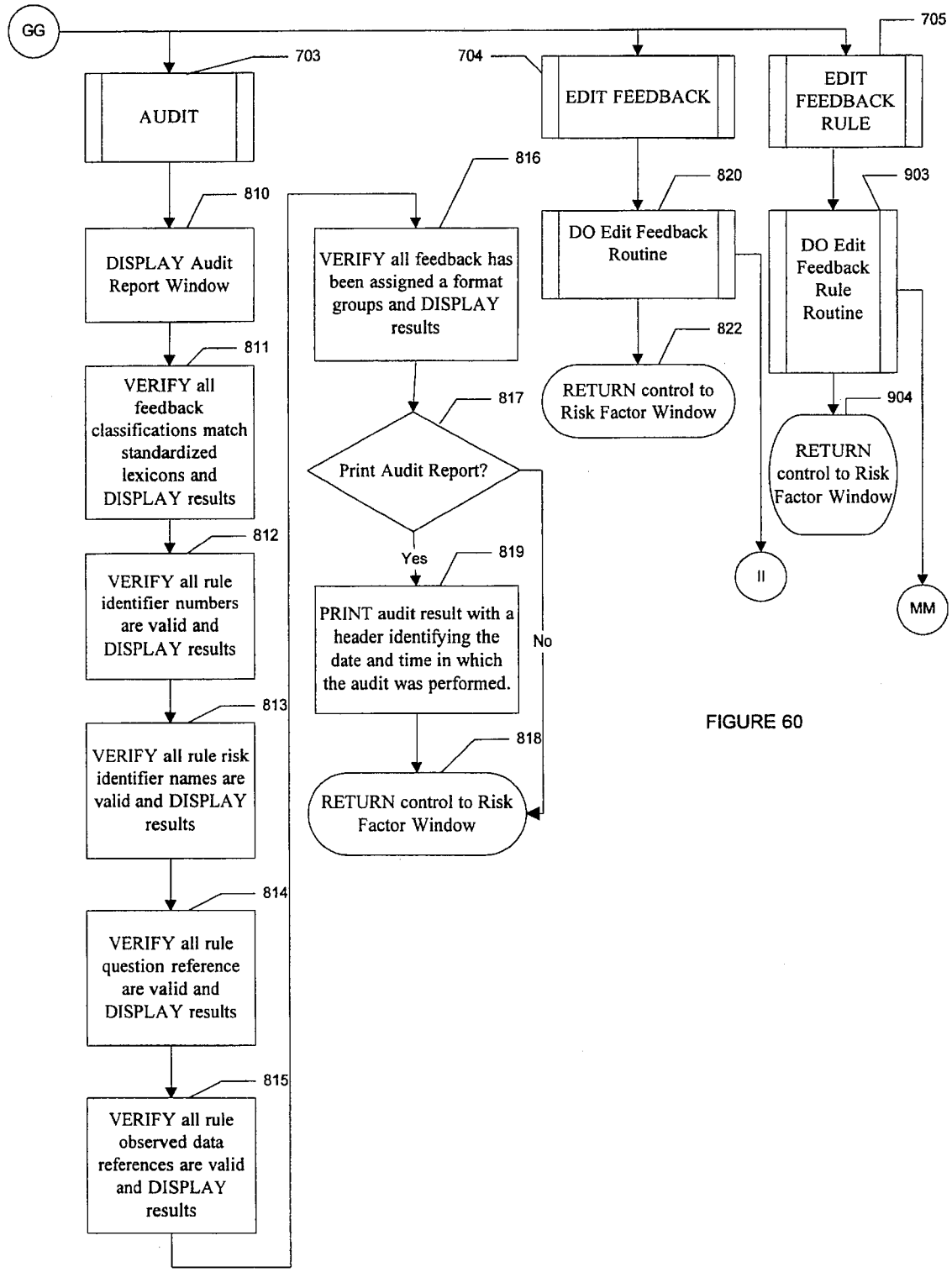
Figure 61:
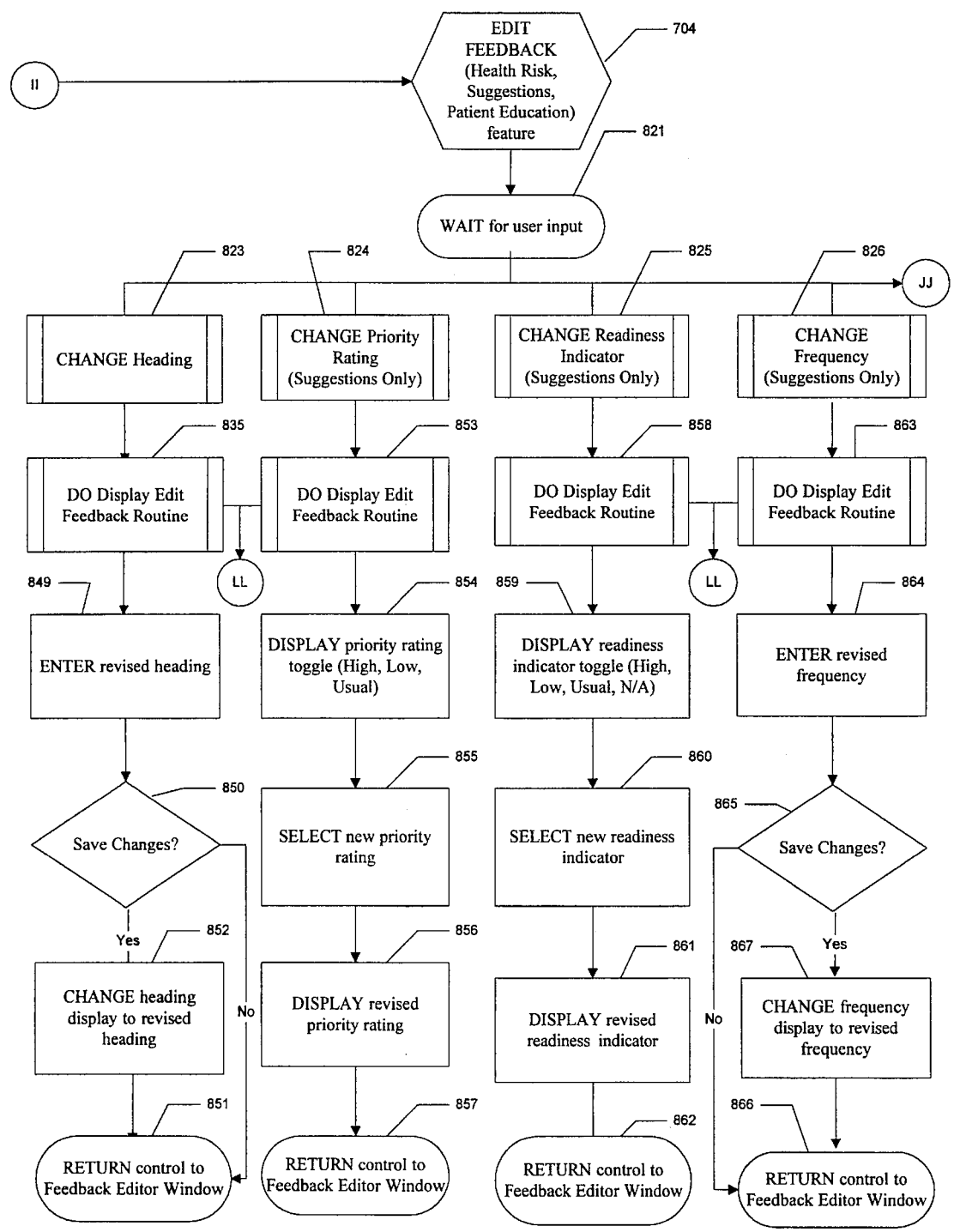
Figure 62:
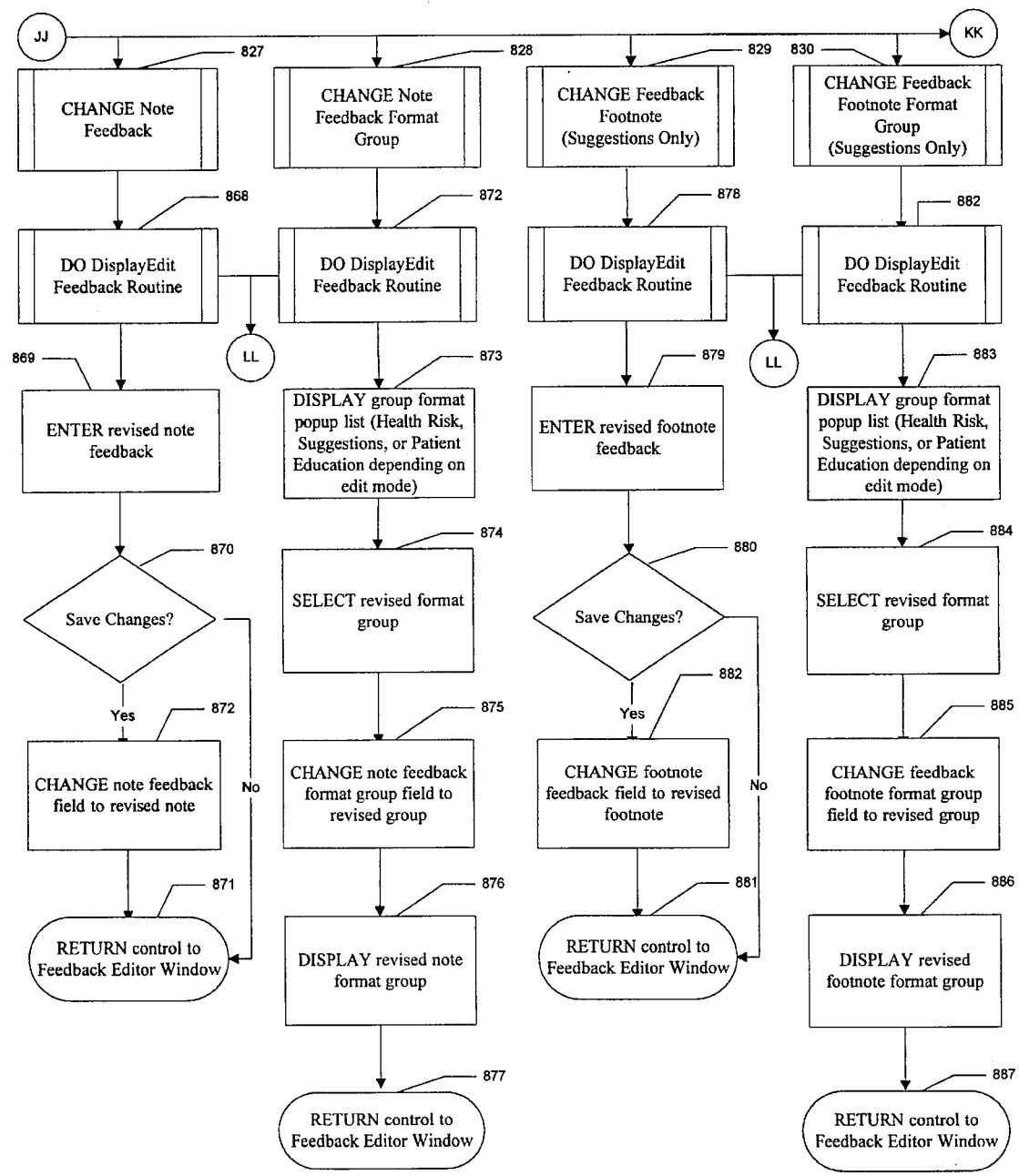
Figure 63:
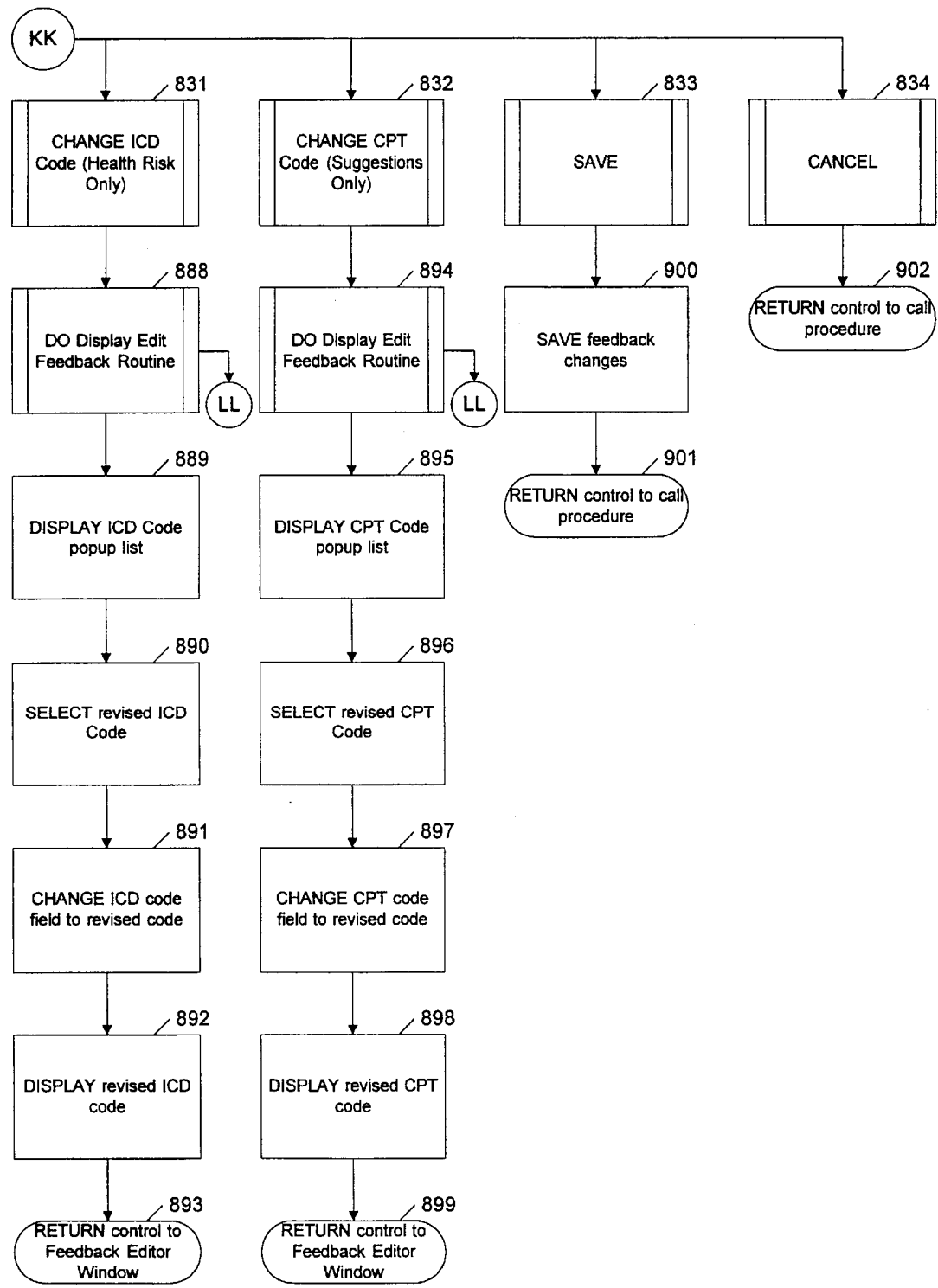
Figure 64:
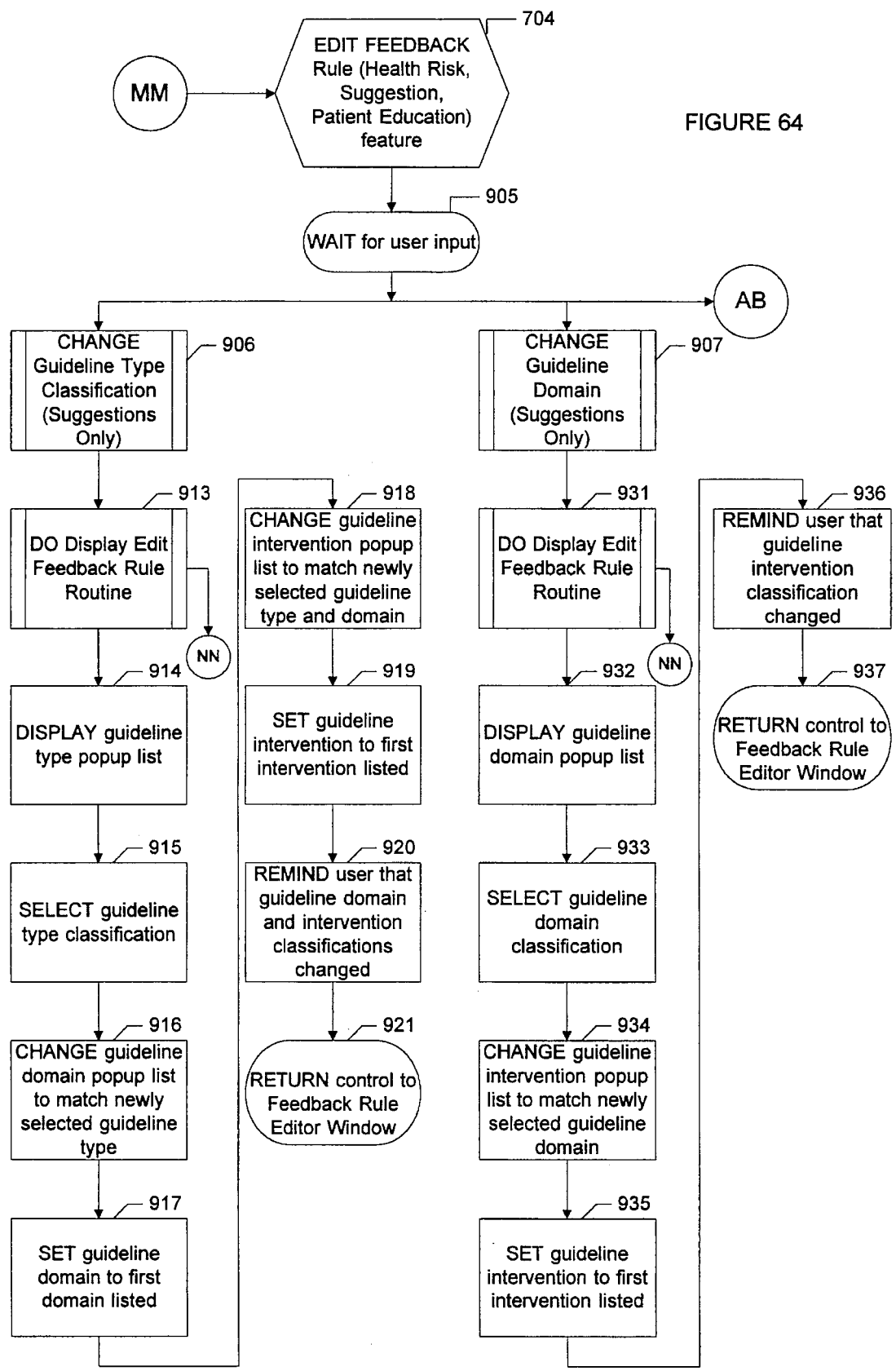
Figure 65:
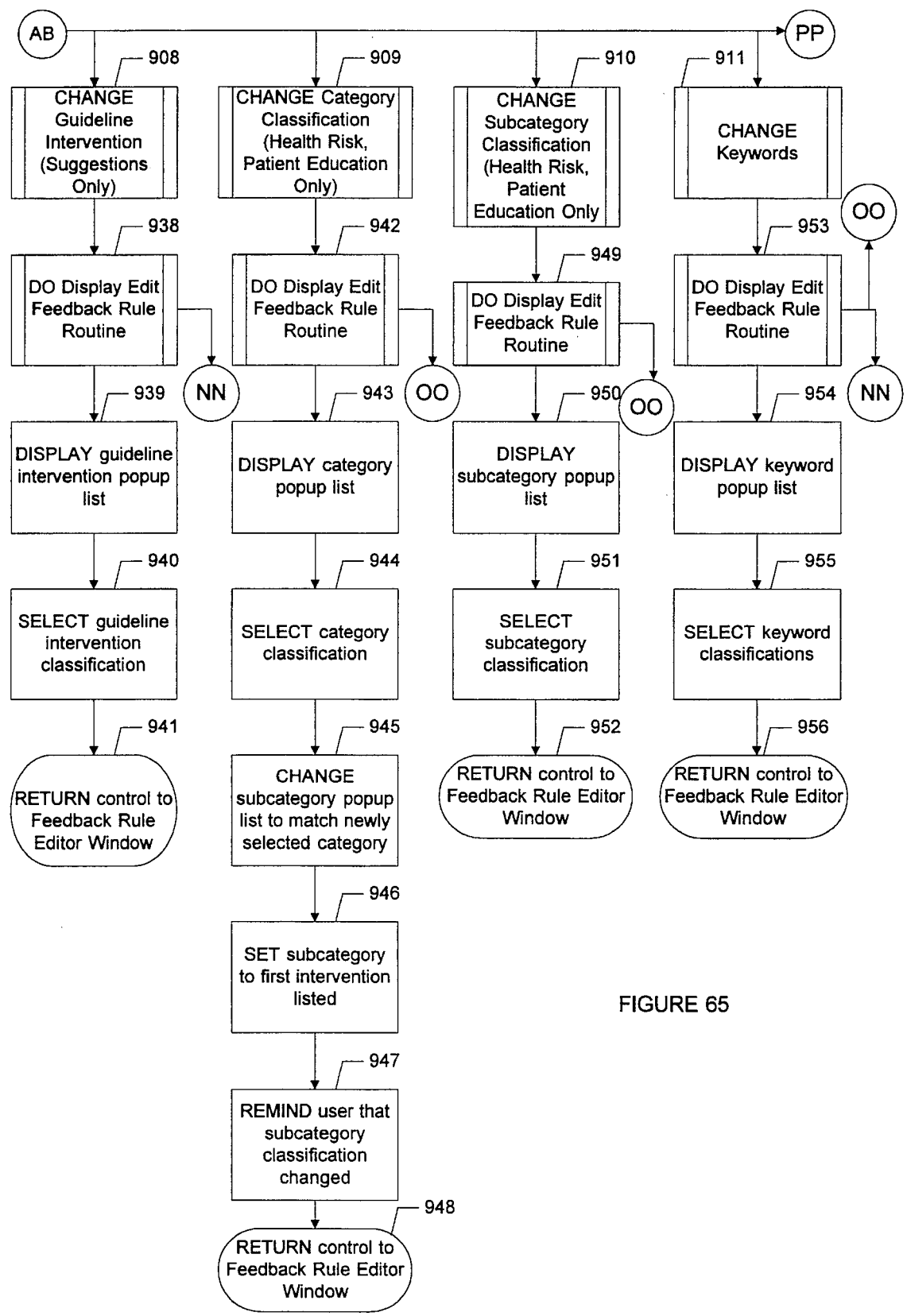
Figure 66:
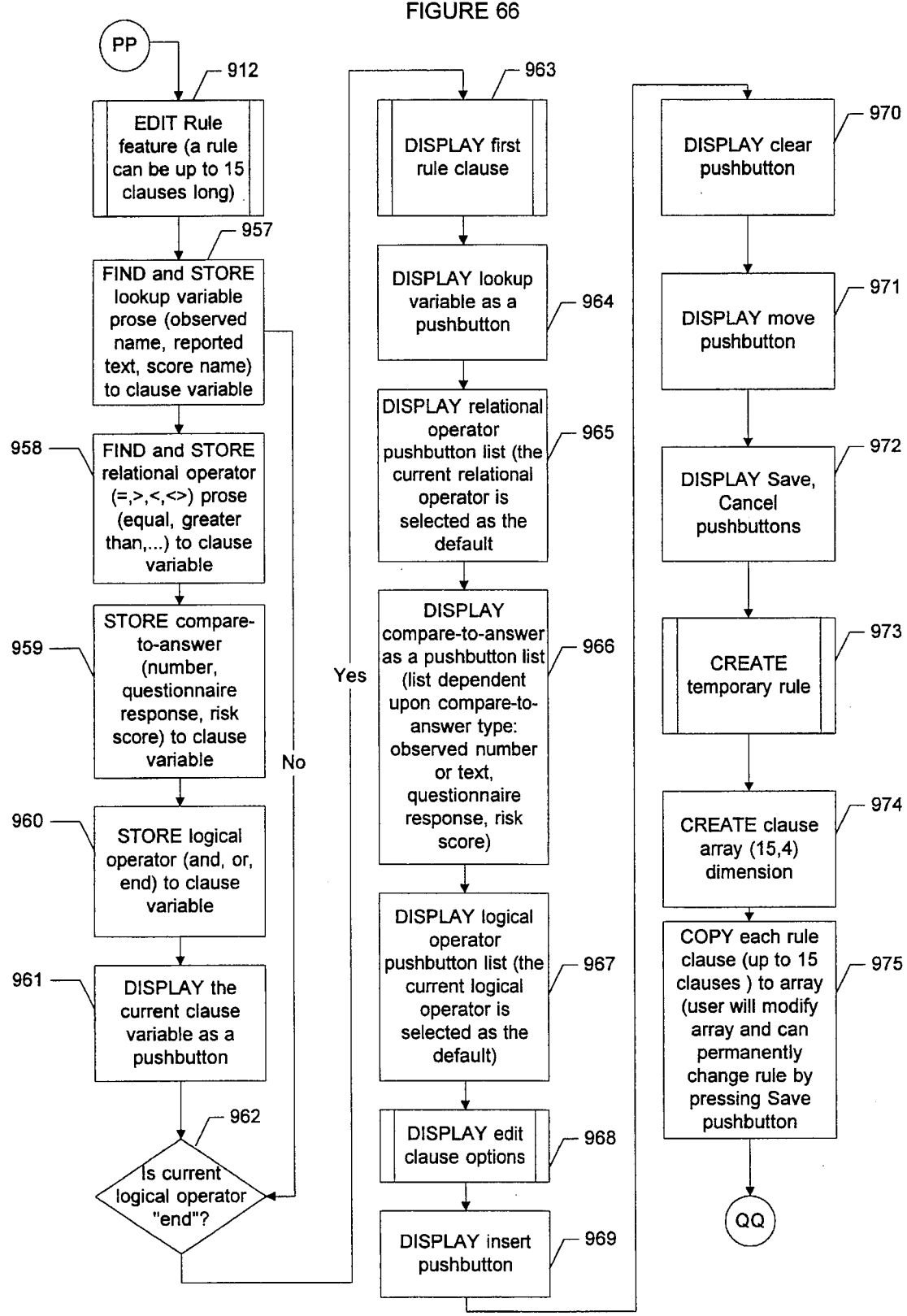
Figure 67:
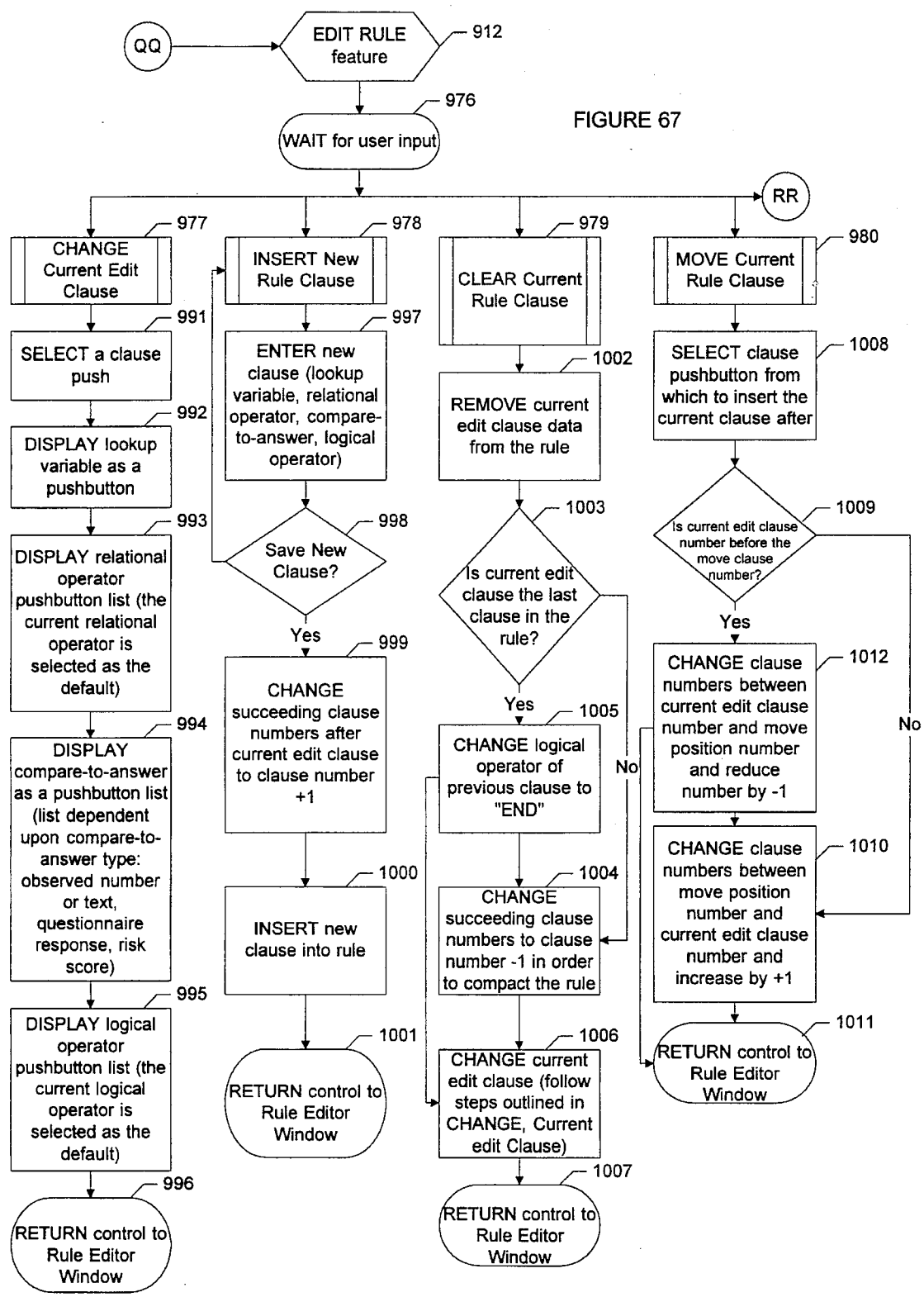
Figure 68:
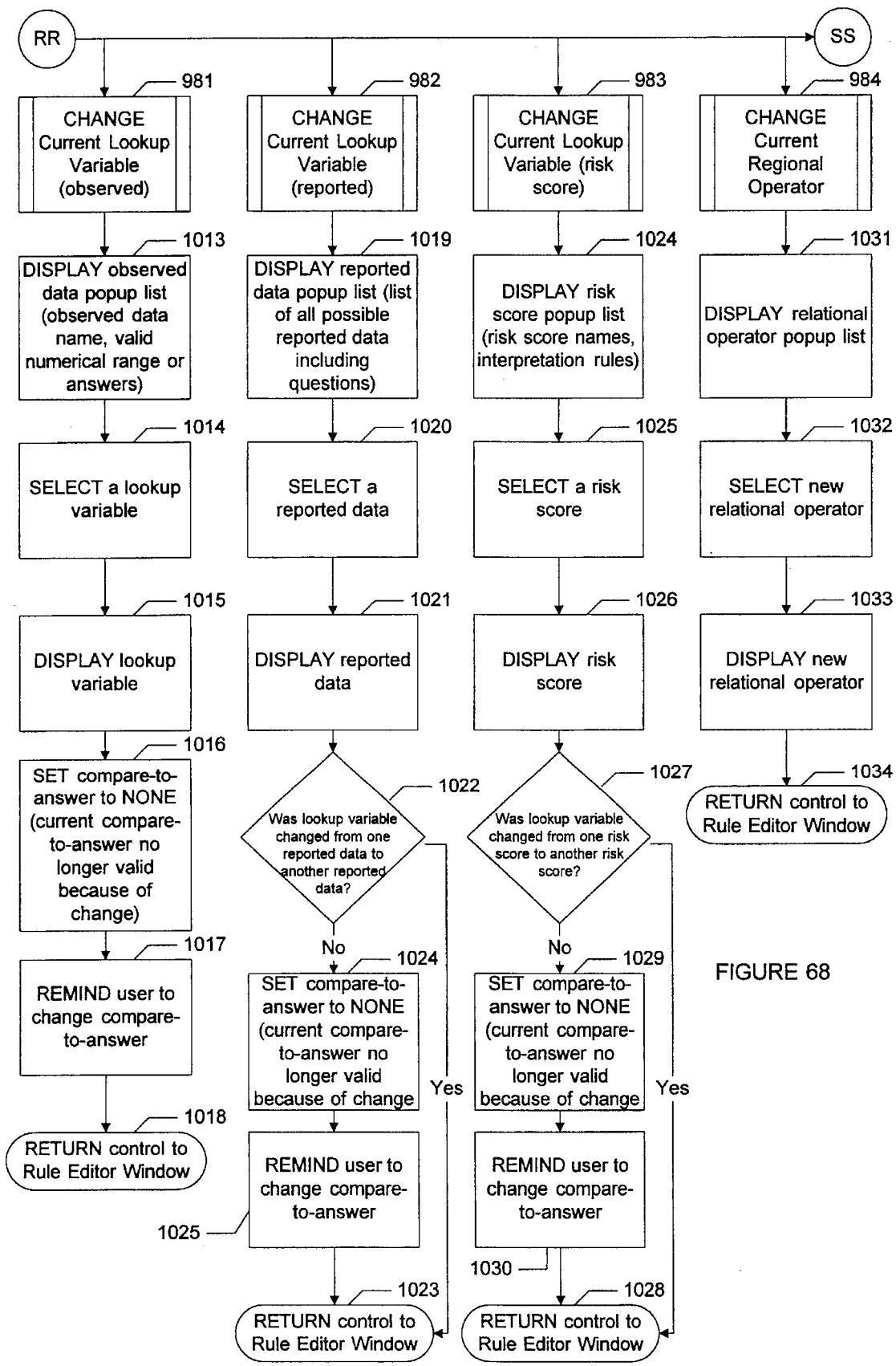
Figure 69:
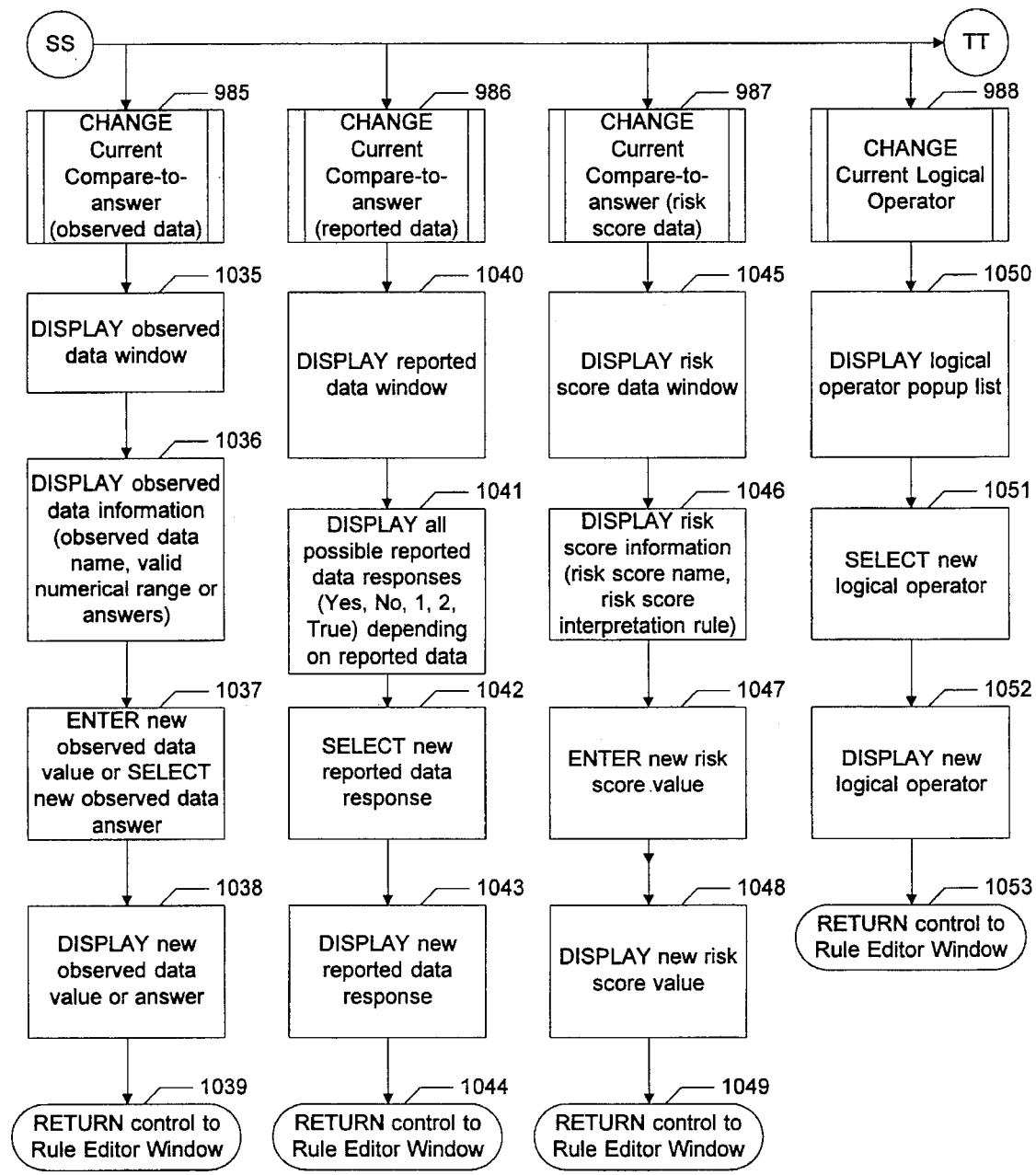
Figure 70:
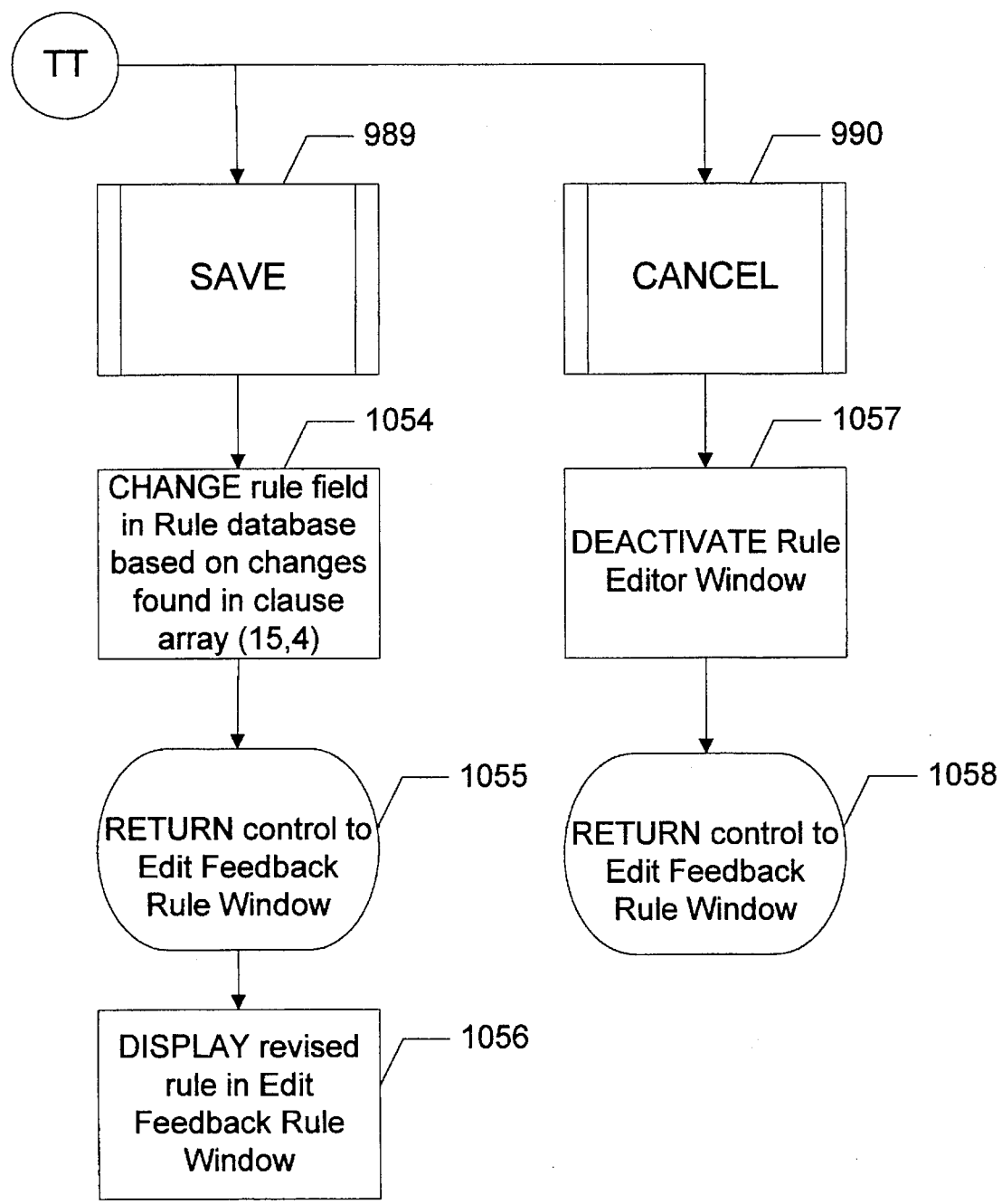
Figure 71:
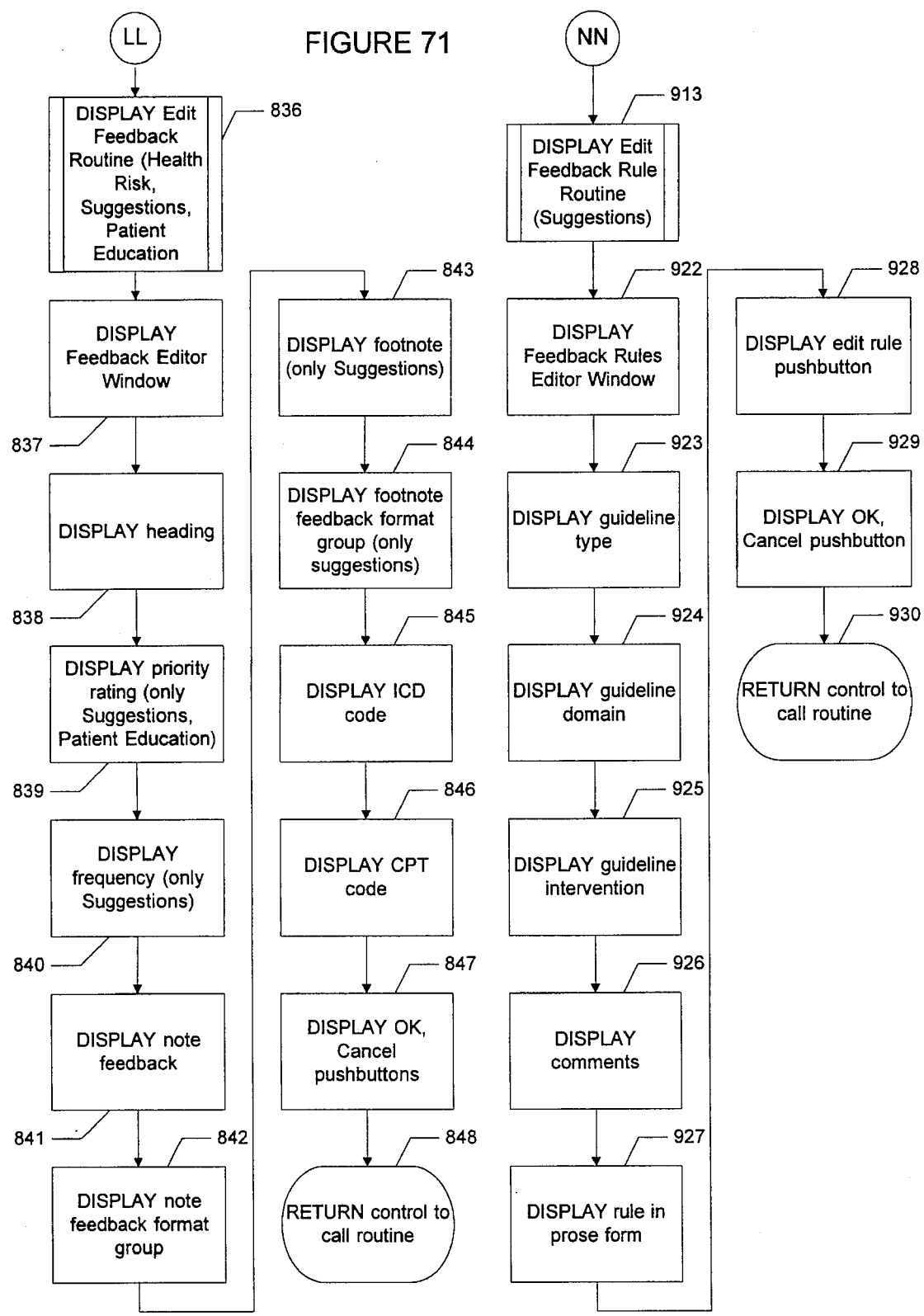
Figure 72:
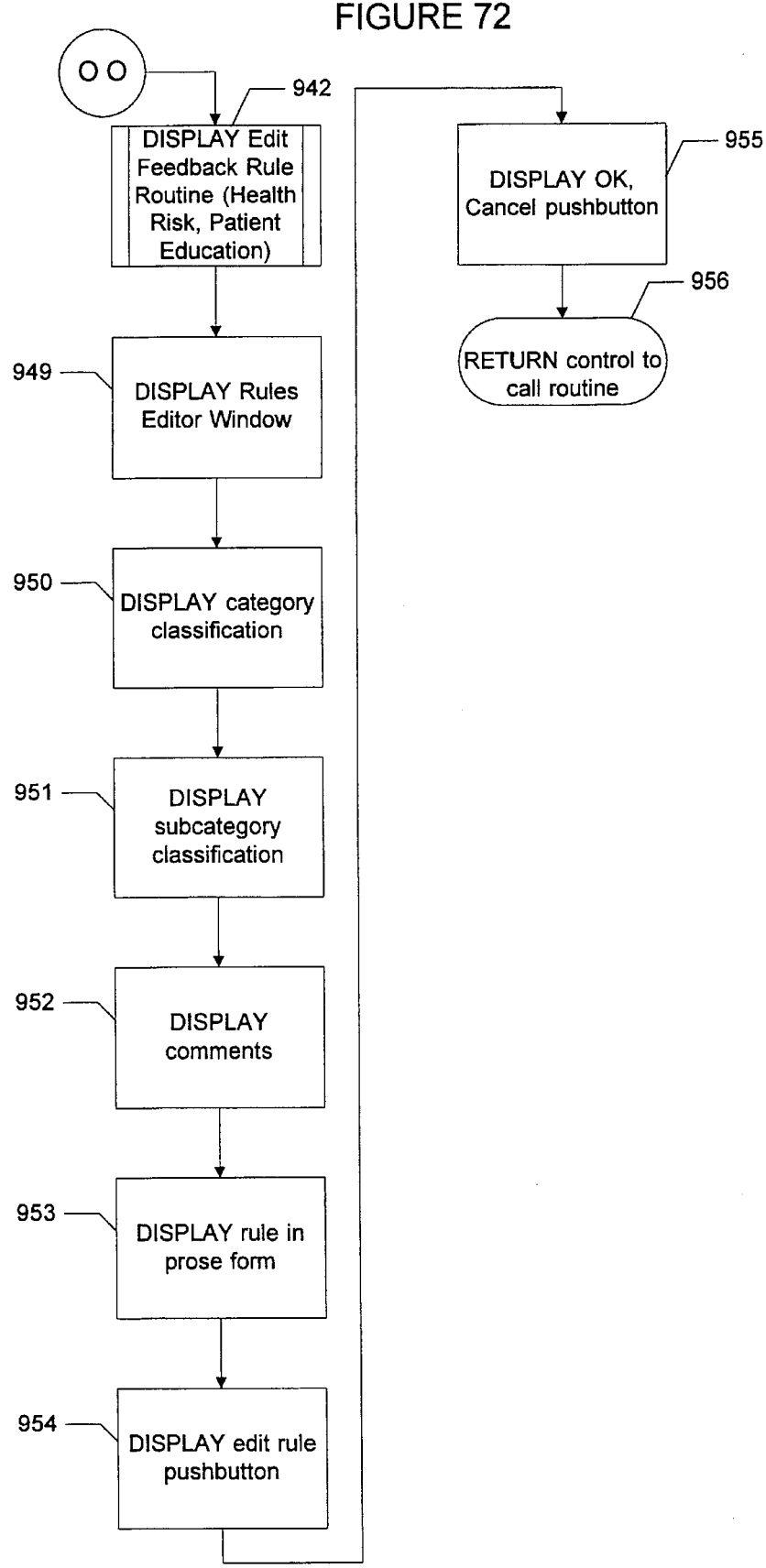
Figure 73:
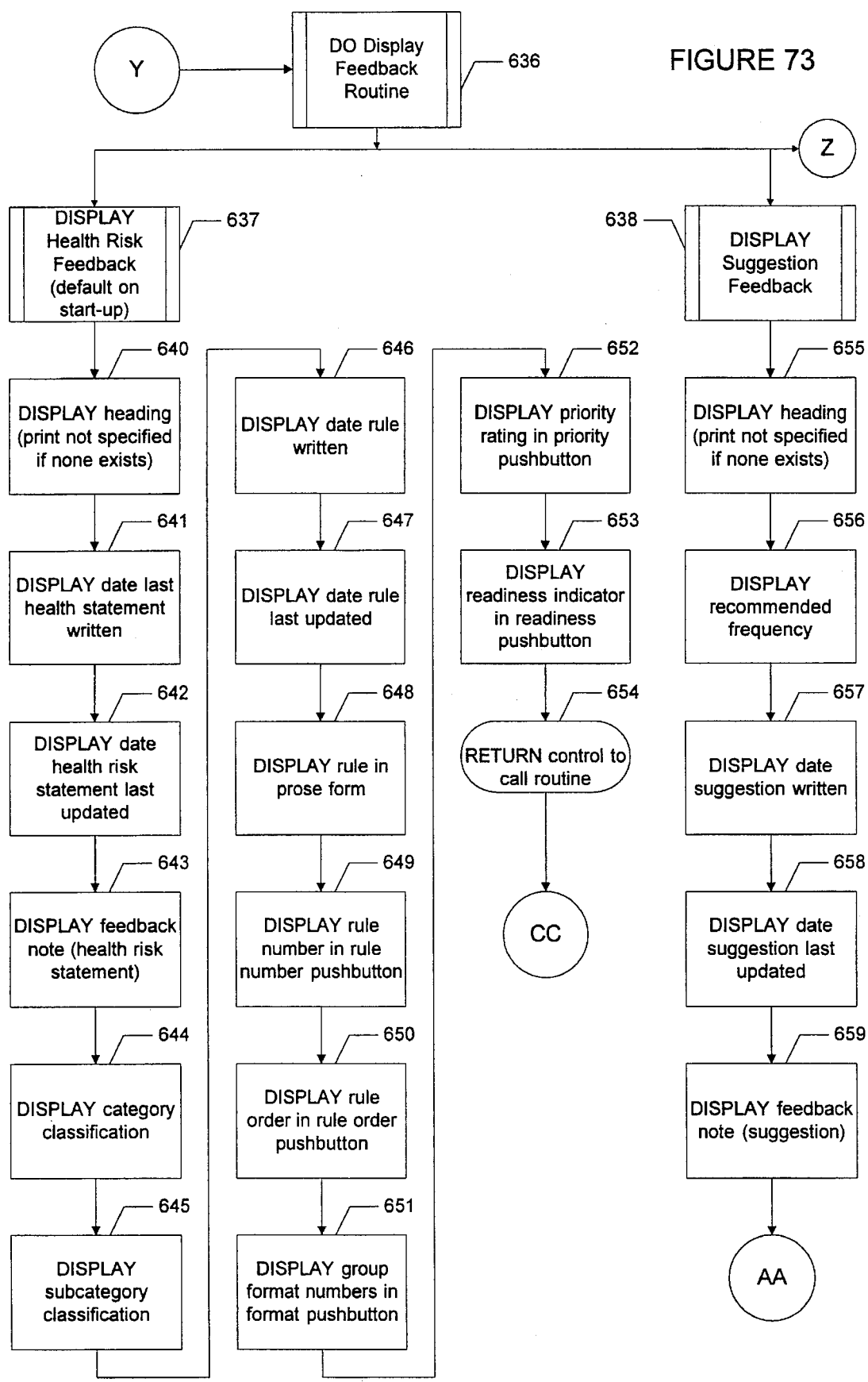
Figure 74:
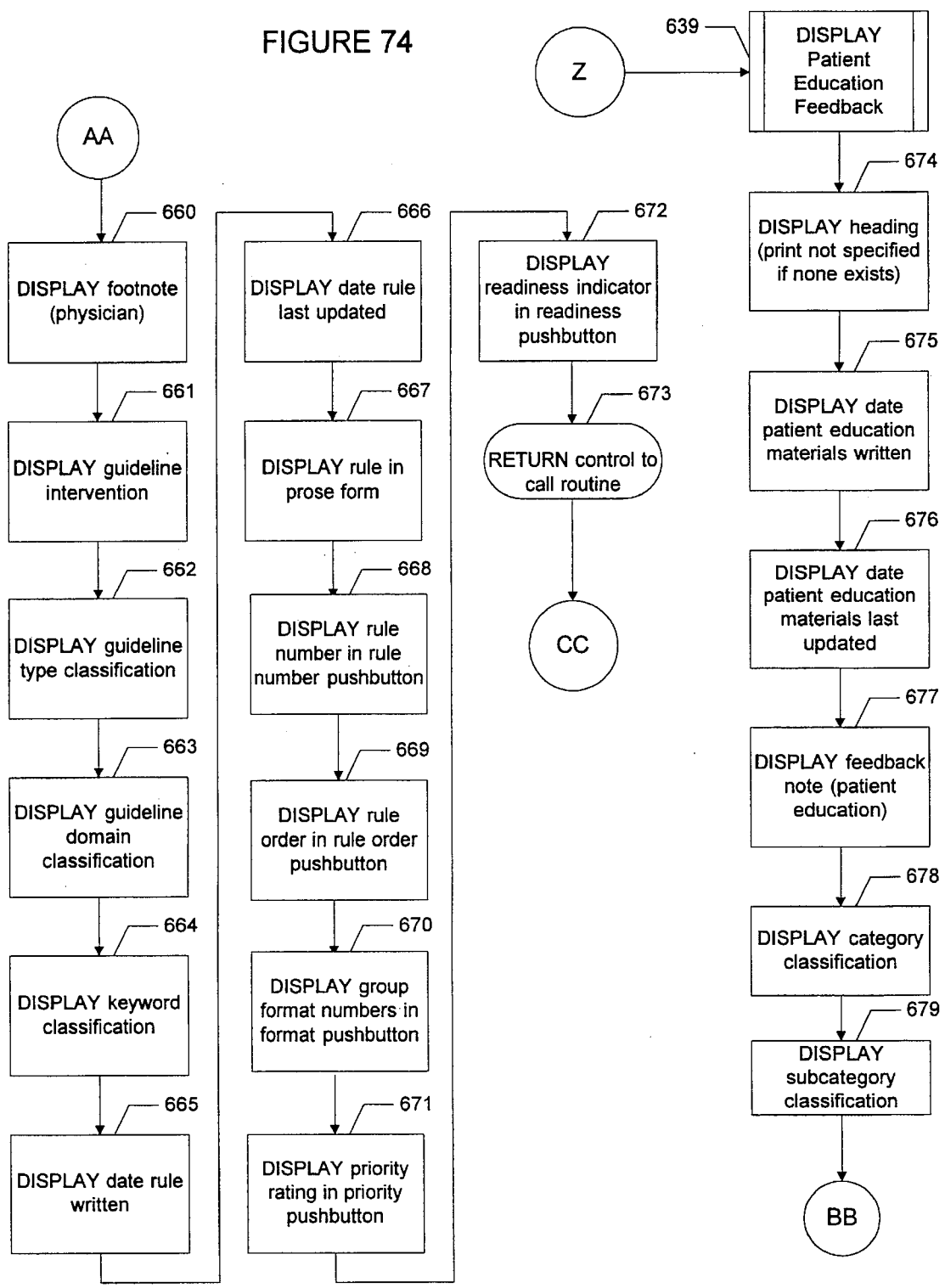
Figure 75:
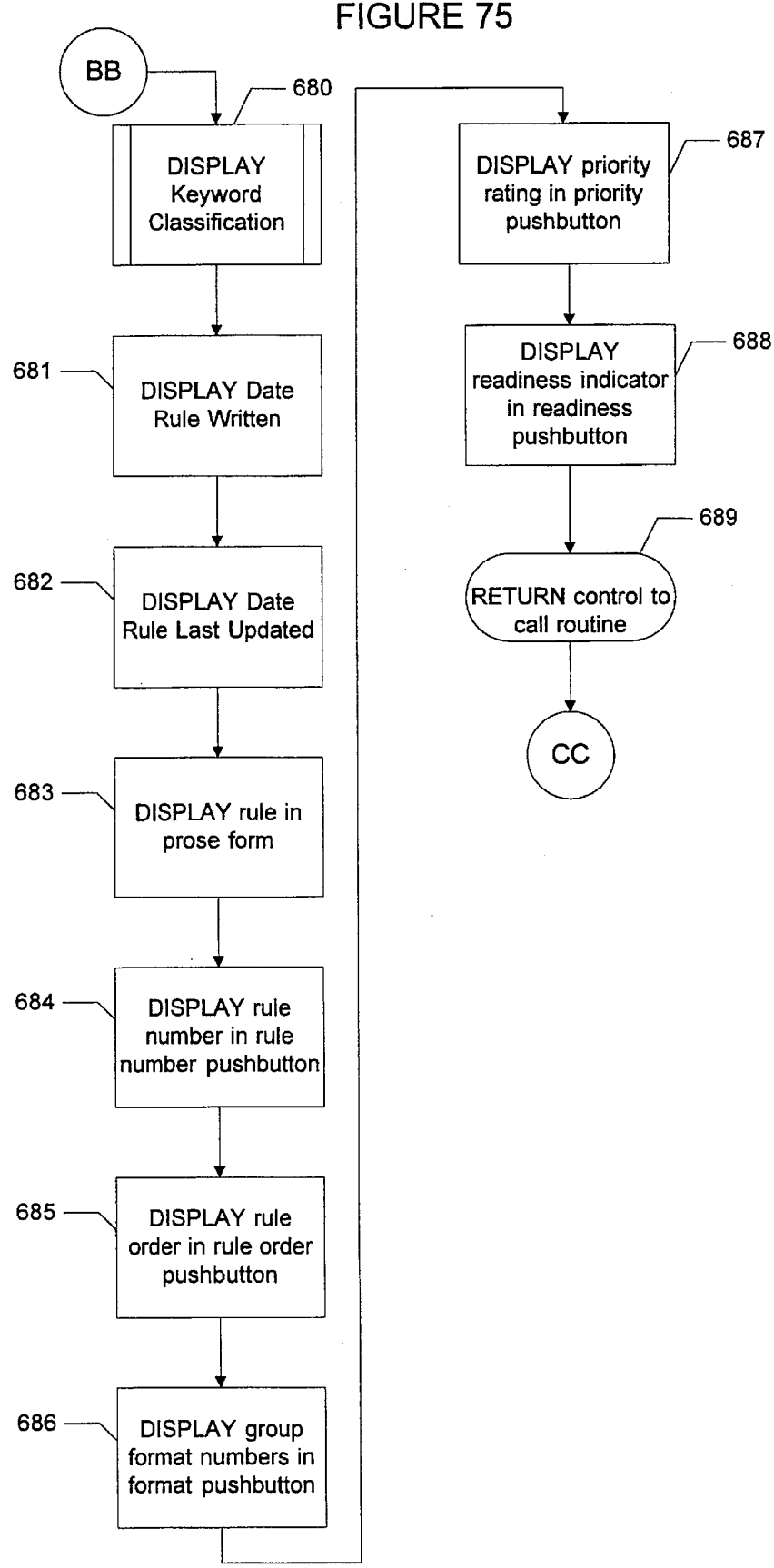
Figure 76:
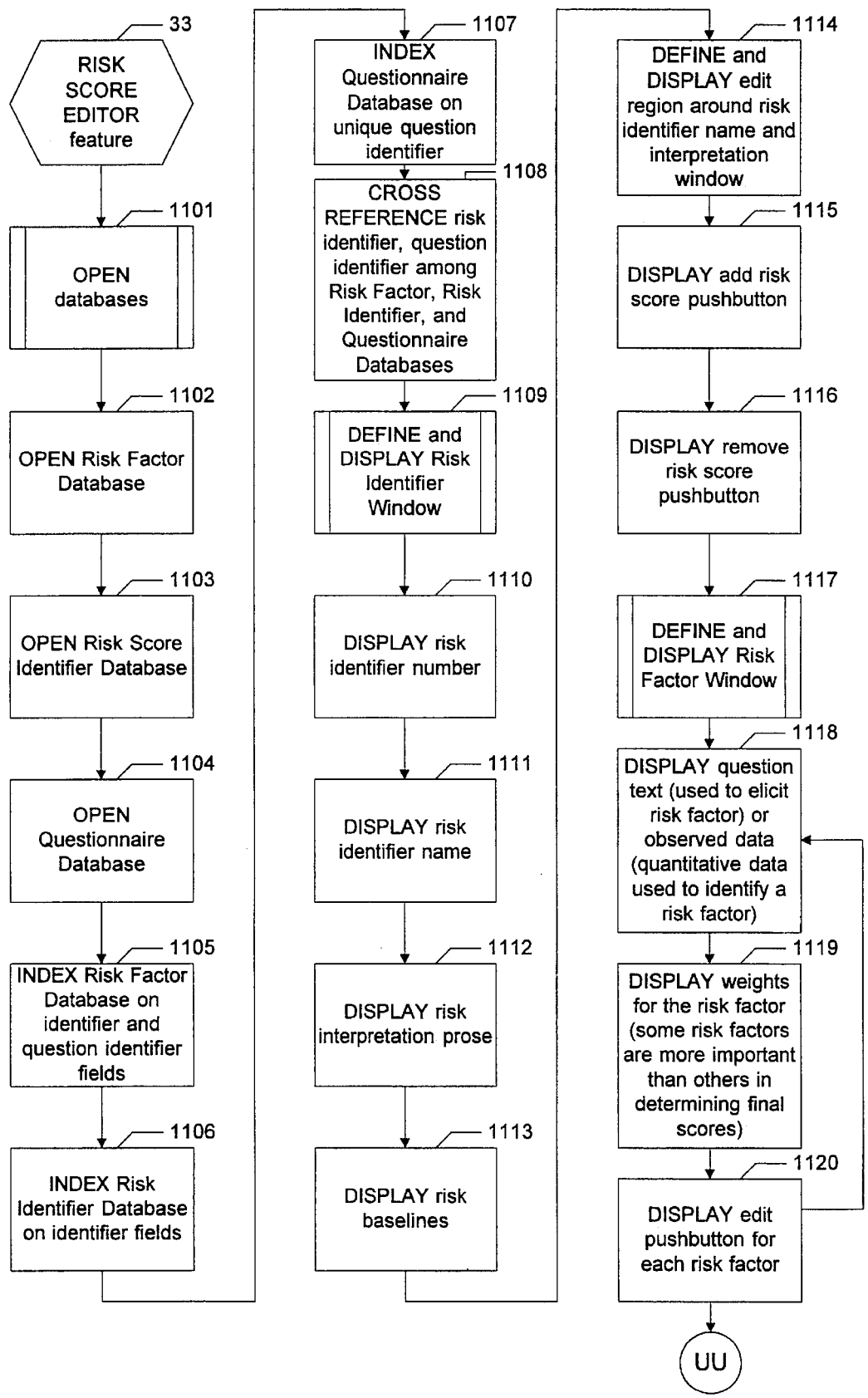
FIGS. 76–81 show a flow diagram of the Risk Score Editor feature.
Figure 77:
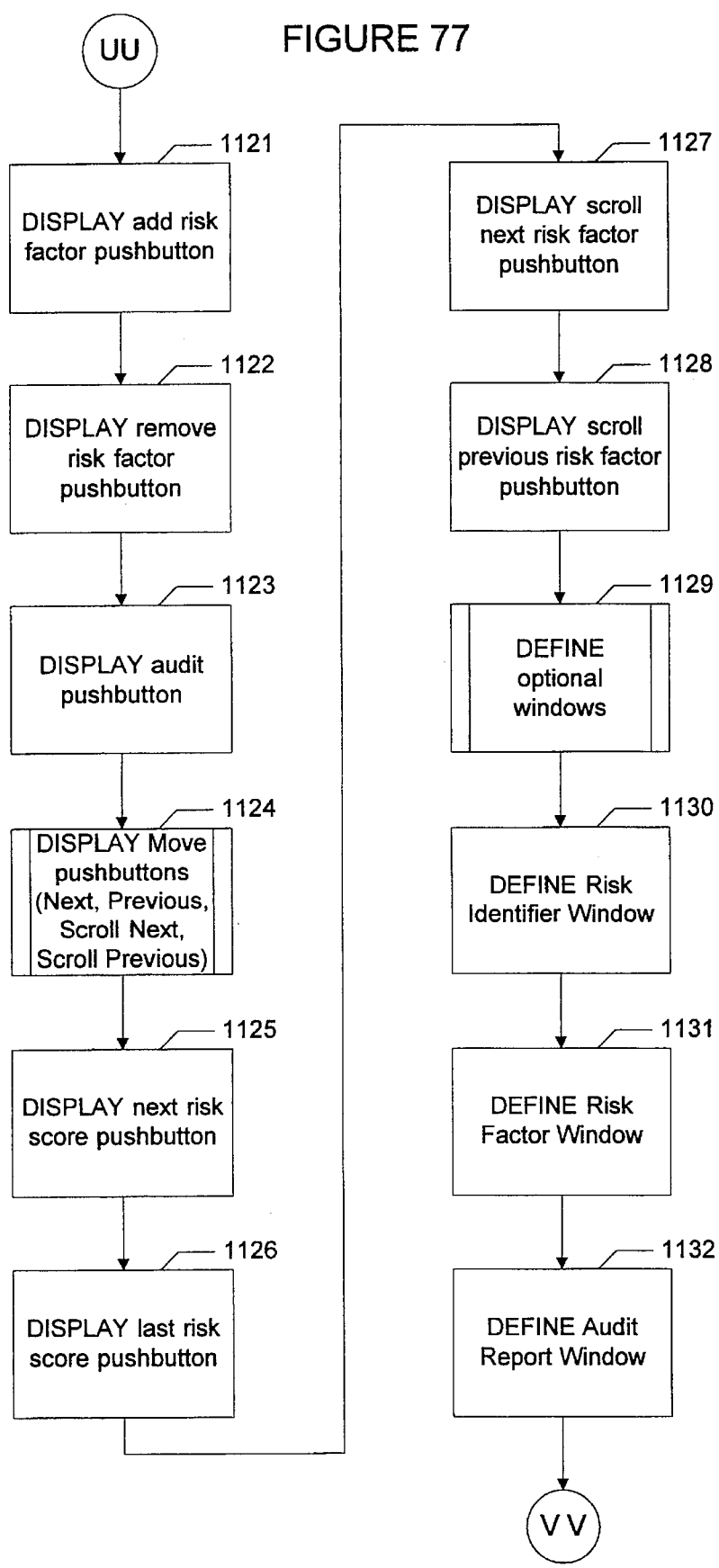
Figure 78:
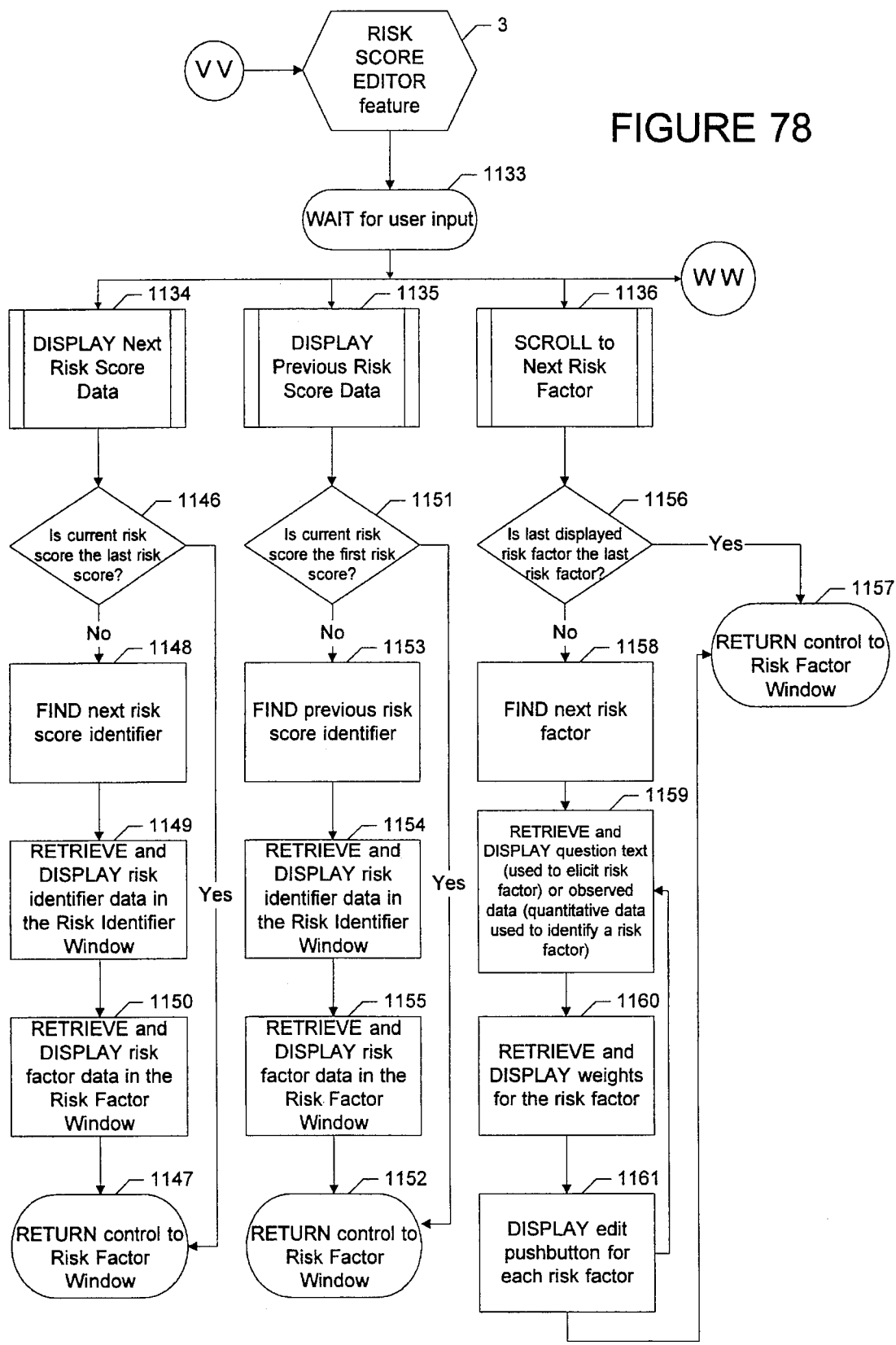
Figure 79:
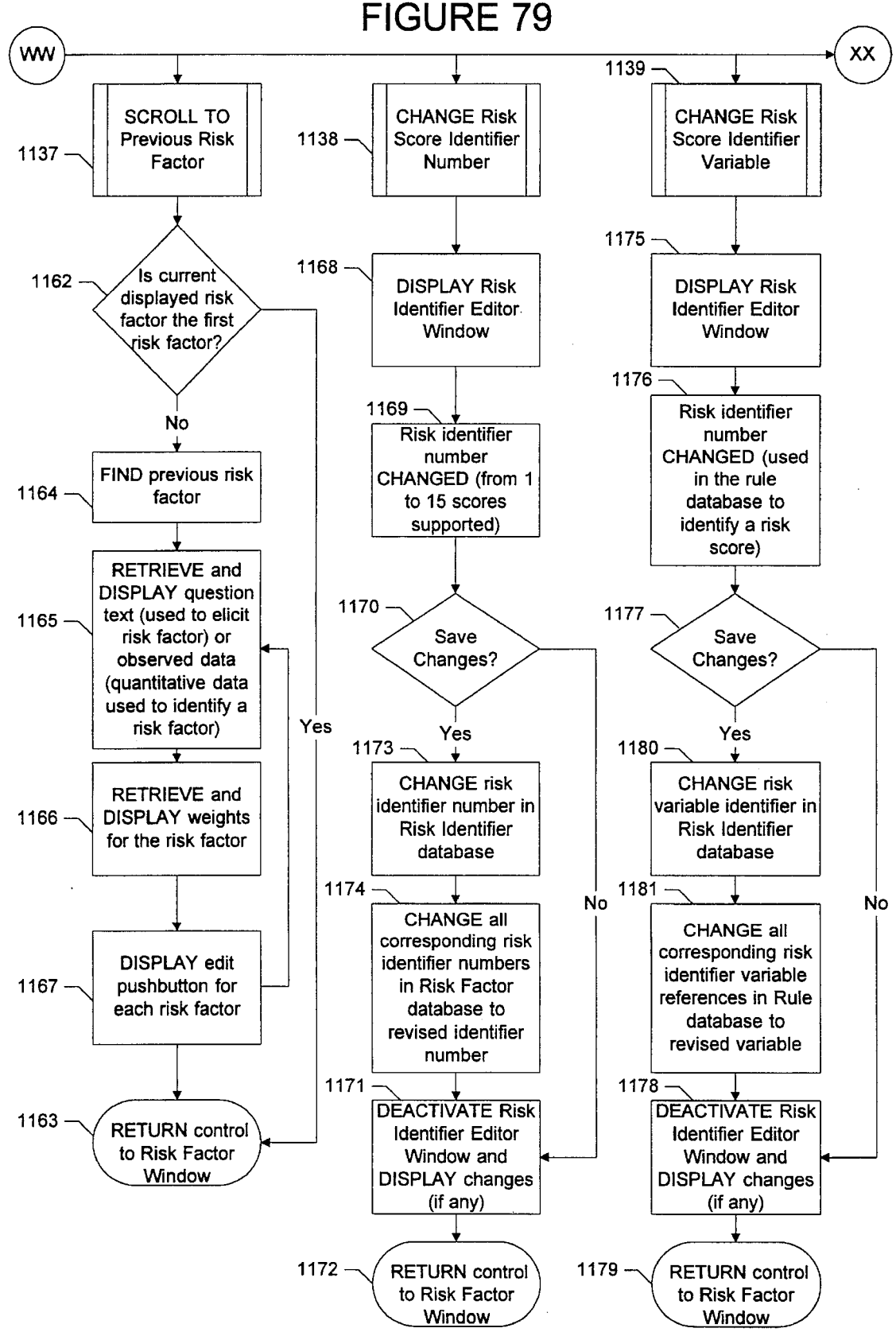
Figure 80:
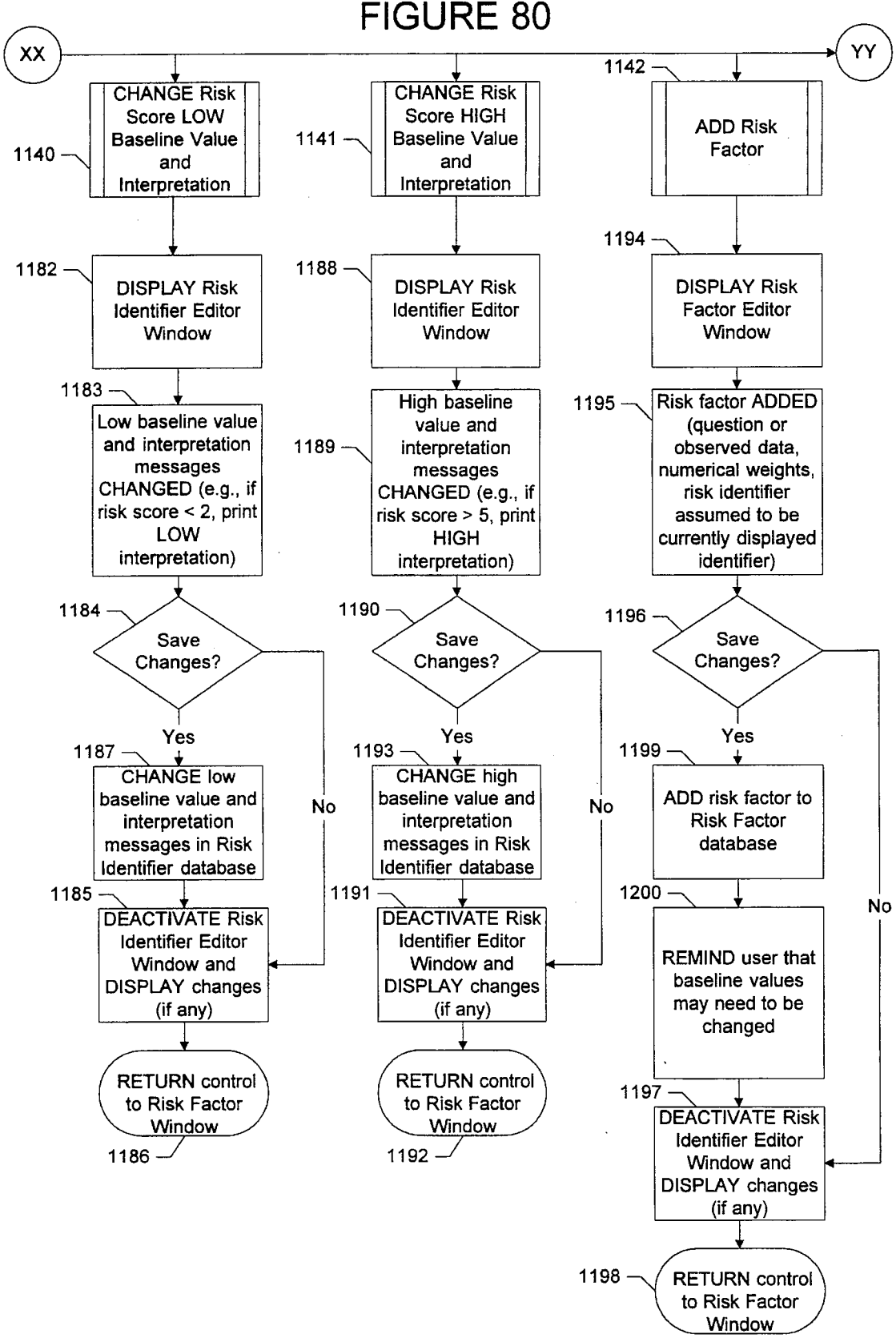
Figure 81:
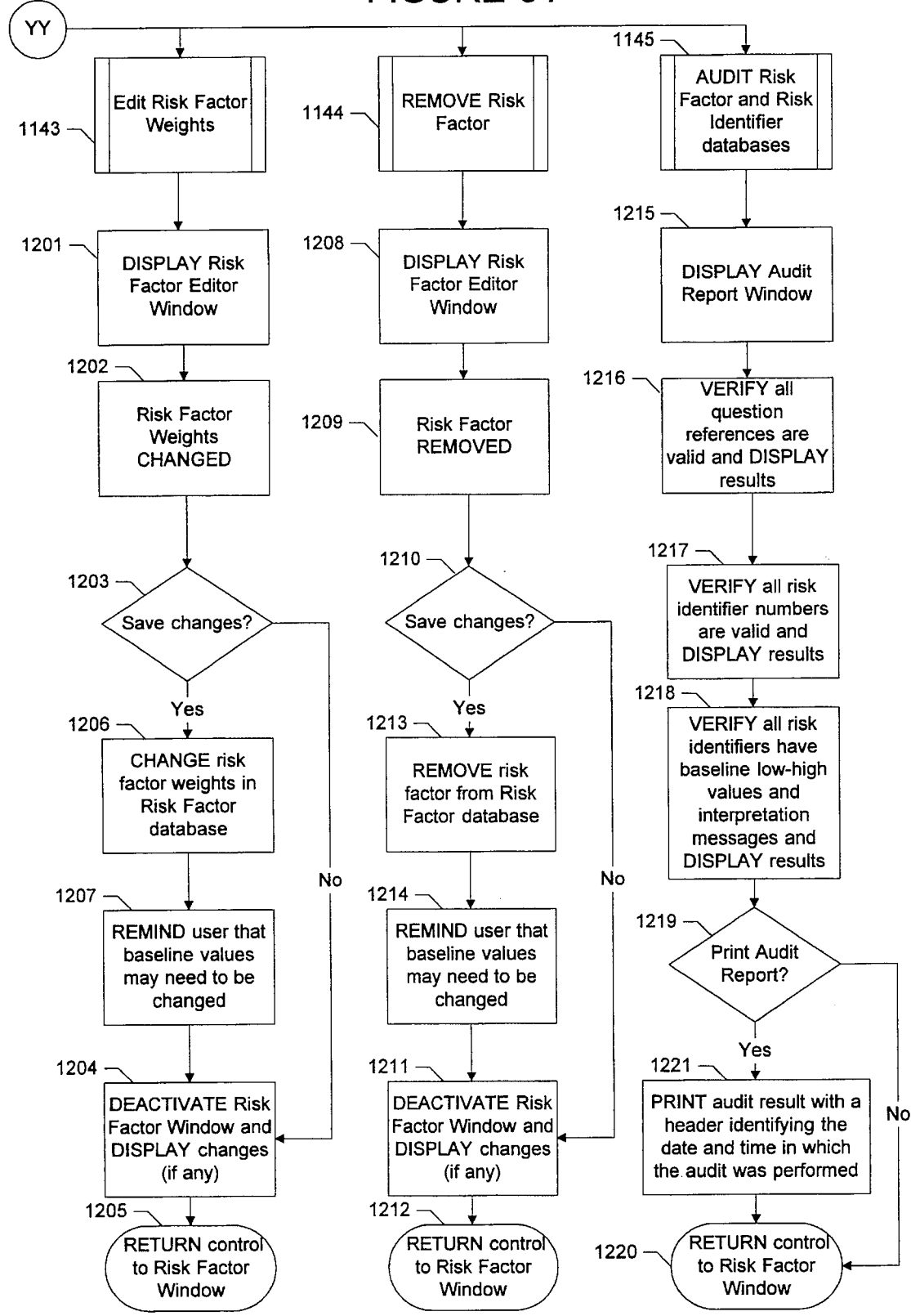

Referring to FIGS. 30 and 31, the software generation feature of the present invention is described. This is the Generate Program feature 53 that can be selected as part of the Utilities feature 5. First, the Program Management database is opened 120 by the user. The user then creates a software model 121 from the pop-up list and also selects the hardware platform pop-up list for each software model 122. The Generate Program window is then defined and displayed 123.

An appropriate software program (a set of databases relative to the project) is then selected 124. First, a software model is selected from the pop-up list 124. The intended hardware platform is then selected from the pop-up list 125. The system then finds 126 the appropriate software model specifications in the program management database.

Software data ".dat" files are then generated 127 based on the software model databases. The instruction data file is created 128 based on the selected model specifications. Following creation of the instruction data file, the Observed data file is created 129, the Reported data file is created 130, the risk score data file is created 131, the fatigue score data file is created 132, the inconsistent score data file is created 133, the rule algorithm data file is created 134, the health risk data file is created 135, the recommendation data file is created 136, the education materials data file is created 137, the report template data file(s) is/are created 138, the report header data file(s) is/are created 139, and the configuration (".ini") files are created 140, all based on the selected model specifications.

The user is then prompted 141 to insert a program card. The system checks 142 to ensure that the card is inserted and that the write protect switch is off. If the card has not been inserted or has been write-protected, the user is once again prompted 141 to insert the card. If the card is inserted and is not write-protected, the operating system files are written 143 to the program card. The software data file is then written 144 to the program card and the program configuration files are written 145 to the program card. Finally, the integrity of the program card files is verified 146 and control is returned 147 to the Generate Program window.

Referring to FIGS. 32–39, the Edit Reported Data/Reported feature 13 (Question Form) process is described. This feature is shown in FIG. 2 as part of the system overview. First, the Add Question window is displayed 150 to the user. The Add Question window is then defined and opened 151 and question data fields are initialized 152. A unique reference number is assigned 153 to the question to be edited and this reference number is displayed 154 along with the question. The date the question was last edited is also displayed 155.

A number of fields are then displayed in the Add Question window. A question field is displayed 156, as well as a question category field 157, a question subcategory field 158, a keyword field 159, an ordernum field 160, a category list (standard lexicon of possible category items from which to choose) 161, a subcategory list 162, a keyword list 163, a Preview Pushbutton option 164, a More Pushbutton option 165, a Library Pushbutton option 166, an OK Pushbutton option 167, and a Cancel Pushbutton option 168. The system then waits 169 for user input. These fields are utilized by the user to enter questions, to classify questions, and to enter question branch information, among other actions.

The user has many input options at this point. Two of these options are OK 170 or CANCEL 171. If the user selects CANCEL 171, the question data fields are cleared 172, the Add Question window is cleared and removed 173, and control is returned 174 to the Edit Question window. If the user selects OK 170, the system checks to ensure that a question has been entered 175, that the question has been classified as a category, subcategory, or keyword 176, that copyright information has been entered 177, and that question branch information has been entered 178. If any of these functions has not been performed, the system displays a reminder 179 to the user to enter the appropriate data and control is returned 180 to the Add Branch (OK or Cancel) window. If all the information has been entered, the new question record is added 181 to the question database.

After the question has been added to the database, a Question Written Date field and a Question Revised Date field are date stamped 182 with the current date and time. The system then writes 183 the system user's name to the field identifying the person who added the question. The user is then queried 184 as to whether he or she wants to add another question to the Question Library. If the user responds "NO", the Add Question window is cleared and removed 185. Control is then returned 186 to the Edit Question, Reported window and New Question is displayed 187 on the Reported window. If the user responds "YES", a new question record is added 188 to the question library database. After the new question has been added 188 to the database, a Question Written Date field and a Question Revised Date field are date stamped 189 with the current date and time. The system then writes 190 the system user's name to the field identifying the person who added the question. The user is then queried 184 again as to whether he or she wants to add another question to the Question Library, and the process is repeated until the user responds "NO".

Options other than OK 170 and CANCEL 171 that are available to the user in the Add Question window include QUESTION TEXT 185, TERMS (Question Category) 186, TERMS (Question Subcategory) 187, KEYWORDS 188, COPYRIGHT 189, COMMENT SECTION 190, EXPLANATION 191, ADD BRANCH WINDOW 192, SOUND 193, and IMAGE 194.

If the QUESTION TEXT 185 pushbutton is selected by the user, the Question text field is activated 195. The user then enters a question 196 and control is returned 197 to the Add Question window.

If the TERMS (Question Category) 186 pushbutton is selected by the user, the Category pop-up list is activated 198. The user then selects 199 a category item from the pop-up list, and the new category is displayed 200 in the category field. The subcategory field is then set 201 to "None", and control is returned 202 to the Add Question window.

If the TERMS (Question Subcategory) 187 pushbutton is selected by the user, the user is queried as to whether a category has been selected 203. If a category has not yet been selected, control is returned 204 to the Add Question window so that the user may select a category. If a category has already been selected, the Subcategory pop-up list is activated 205 for the selected category, and a subcategory is selected 206 from the pop-up list. The new subcategory is displayed 207 in the subcategory field and control is returned 204 to the Add Question window.

If the KEYWORDS 188 pushbutton is selected by the user, the Keyword pop-up list is activated 208. A keyword item is selected 209 from the pop-up list, and the new keyword is displayed 210 in the keyword field. Control is then returned 211 to the Add Question window.

If the COPYRIGHT 189 pushbutton is selected by the user, the copyright field is activated 212, the user enters 213 copyright data, and control is returned 214 to the Add Question window.

If the COMMENT SECTION 190 pushbutton is selected by the user, the comment section field is activated 215, the user enters 216 comment data, and control is returned 217 to the Add Question window.

If the EXPLANATION 191 pushbutton is selected by the user, the explanation section field is activated 218, the user enters 219 explanation data, and control is returned 220 to the Add Question window.

If the user selects the ADD BRANCH WINDOW 192 pushbutton, the Add Branch window is activated 221 and the question answer format field is displayed 222. The default format is the Yes/No/Not Sure format. This is the question and answer format that will be presented to the unskilled user by the questionnaire application. Current branch pointers, which were initialized at 0, are then displayed 223, the Question Answer format pushbutton is displayed 224, and the Save and Cancel pushbuttons are displayed 225. The Question Answer Format and Branch Pointer data are then written 226 to temporary variables, and the system waits 227 for further user inputs. The choices presented to the user in the Add Branch window are QUESTION ANSWER FORMAT 228, BRANCH POINTERS 229, CANCEL 230, and SAVE 231.

If the user selects the QUESTION ANSWER FORMAT 228 pushbutton from the Add Branch window, the question answer format pop-up list is activated 232. The user then selects 233 an answer format from the pop-up list. The number of format answer options is compared 234 to the number of branch pointers. The user is then queried 235 as to whether the new answer format is similar to the old answer format. If it is, control is returned 236 to the Add Branch window. If it is not, a dialogue box is displayed 237 to the user to remind the user to change the current branch pointers to conform to a new question answer format, and control is then returned 236 to the Add Branch window.

If the user selects the BRANCH POINTERS 229 pushbutton from the Add Branch window, the branch pointer pop-up list is activated 238. This list shows questions that are located around the current question in the current question sequence. The user selects 239 the question from the pop-up list to which the system will branch. The system then displays 240 the question text for the new branch pointer, and the new branch pointer is stored 241 to a temporary variable. Control is then returned 242 to the Add Branch window.

If the user selects the CANCEL 230 pushbutton from the Add Branch window, control is returned 243 to the Add Question window.

If the user selects the SAVE 231 pushbutton from the Add Branch window, temporary question answer format and branch pointer data are written 244 to permanent variables and control is returned 245 to the Add Question window.

If the user selects the SOUND 193 pushbutton from the Add Question window, the Sound window is activated 246 and the current question field is displayed 247. The sound file pop-up list is then displayed 248 such that each file is identified by a unique question reference number. SELECT FILE 252, SAVE 253, PLAY 254, and CANCEL 255 pushbuttons are then displayed, and the temporary sound file variable is initialized 250. The system then waits for user input.

If the user selects the SELECT FILE 252 pushbutton from the Sound window, the selected sound object file reference is stored 256 to a temporary variable and control is returned 257 to the SOUND window.

If the user selects the SAVE 253 pushbutton from the Sound window, the selected sound object file reference is permanently stored 258 and control is returned 259 to the Add Question window.

If the user selects the PLAY 254 pushbutton from the Sound window, a link between an OLE sound object file and a sound program is established 260, instructions to play the sound object file are sent 261 to the sound program, and control is returned 262 to the Sound window.

If the user selects the CANCEL 255 pushbutton from the Sound window, control is returned 273 to the Add Question window.

If the user selects the IMAGE 194 pushbutton from the Add Question window, the Image window is activated and the current question field is displayed 264. The image file pop-up list is then displayed 265, and the SELECT FILE 269, SAVE 270, PREVIEW 271, and CANCEL 272 pushbuttons are displayed 266 in the Image window. The temporary image file variable is initialized 267, and the system waits 268 for further user input.

If the user selects the SELECT FILE 269 pushbutton from the Image window, the selected image object file reference is stored 273 to a temporary variable and control is returned 274 to the Image window.

If the user selects the SAVE 270 pushbutton from the Image window, the selected image object file reference is permanently stored 275 and control is returned 276 to the Add Question window.

If the user selects the PREVIEW 271 pushbutton from the Image window, the system establishes 277 a link between the OLE image object file and the image program, thee image object file is displayed 278 in the Preview window, and control is returned to the Image window.

If the user selects the CANCEL 272 pushbutton form the Image window, control is returned to the Add Question window.

Referring to FIGS. 40–52, the Edit Guideline Library feature 20 process is described. First, the database directory is opened 300, and the Guideline Library database in particular is opened 301 from the directory. Then the Background Library database is opened 302. The Background Library database contains guideline background references organized according to keywords. Next, the Rule Library database is opened 303. This database contains guideline decision rules. Finally, health history and patient education databases relative to the selected program are opened 304. The system then indexes 305 the Guideline Library Database according to guideline type, and within each type by domain. The Background Library is indexed 306 according to reprint identifier reference number, and the Rule Library is indexed 307 according to unique rule reference number. The Background Library and Rule Library are then cross referenced 308 to the Guideline Library database.

At this point, Guideline Type, Domain, and Intervention pushbutton lists are created 309. The Guideline Lexicon database is opened 310 and a pop-up list of available guideline types is created 311. Next, pop-up lists of available guideline domains for each guideline type are created 312 and pop-up lists of available guideline interventions for each guideline type and domain are created 313.

A Guideline Developer pushbutton list is then created 314. First, a Guideline Developer database is opened 315. Next, a pop-up list of available guideline developers is created 316 and a pop-up list of reprint identifiers with publication title is created 317.

Next, a Guideline Library window is defined and displayed 318. A number of items are displayed as pushbuttons in the Guideline Library window. The guideline type is displayed 319 as a pushbutton, the default for the guideline type being PREVENTION. Also displayed as pushbuttons are the guideline domain 320, starting with the first domain within the guideline type; the guideline intervention 321, starting with the first intervention within the guideline domain; the first guideline developer 322, the default for the Prevent Guideline being the American College of Physicians; the second guideline developer 323, the default for the Prevent Guideline being the Canadian Task Force; and the third guideline developer 324, the default for Prevent Guidelines being the United States Preventative Services Task Force.

Next, the guideline information for the three displayed guideline developers is organized and displayed 325. First, the system finds and stores 326 the general guideline criteria for the developers, first for the first developer, then for the second, and finally for the third. The system then finds and stores 327 the selective guideline criteria for the guideline developers, in the same order. The system next finds and stores 328 guideline evidence references for the guideline developers and finds and stores 329 the guideline published date for the developers. Next, the name of the user who entered the guideline and the date on which it was entered is found and stored 330, and the name of the user who last edited the guideline and the date on which it was last edited is found and stored 331. The guideline information is then created and displayed as a pushbutton 332, and the system waits for user input, that is, waits for the user to select a displayed pushbutton.

The pushbuttons from which the user may select at this point are DISPLAY First Intervention 334, DISPLAY Last Intervention 335, NEXT Intervention 336, PREVIOUS INTERVENTION 337, CHANGE Guideline Type 338, CHANGE Guideline Domain 339, CHANGE Guideline Intervention 340, CHANGE Guideline Developer 341, EDIT Guideline Information 342, VIEW Corresponding Suggestion 343, VIEW Corresponding Health Risk Statement 344, VIEW Corresponding Patient Education Material 345, and CANCEL 346.

If the user selects the DISPLAY First Intervention 334 pushbutton, the system finds 347 the first intervention for the specified guideline type and domain that is published by a specified guideline developer. The system then retrieves 348 the associated guideline information and displays 349 the first guideline intervention information as a pushbutton. These steps are repeated for the second and third guideline developers, and control is returned 350 to the Guideline Library window.

If the user selects the DISPLAY Last Intervention 335 pushbutton, the system will first find 351 the last intervention for a specified guideline type and domain that is published by a specified guideline developer. The system then retrieves 352 the associated guideline information and displays 353 the last guideline intervention information as a pushbutton. These steps are repeated for the second and third guideline developers, and control is returned 354 to the Guideline Library window.

If the user selects the NEXT Intervention 336 pushbutton, the system finds 355 the next intervention for a specified guideline type and domain that is published by a specified guideline developer. The system then queries 356 the user as to whether the current intervention is the last intervention. If the current intervention is the last intervention, the associated guideline information is retrieved 358. If the current intervention is not the last intervention, the system finds 357 the first intervention and then retrieves 358 the associated guideline information. The system then displays 359 the next guideline intervention information as a pushbutton. These steps are repeated for the second and third guideline developers, and control is returned 360 to the Guideline Library window.

If the user selects the PREVIOUS Intervention 337 pushbutton, the system finds 361 the previous intervention for a specified guideline type and domain that is published by a specified guideline developer. The system then queries 362 the user as to whether the current intervention is the first intervention. If it is, the system retrieves 363 the associated guideline information. If it is not, the system first finds 364 the last intervention and then retrieves 363 the associated guideline information. The system then displays 365 the previous guideline information as a pushbutton. The entire process is repeated for the second and third guideline developers, and control is returned 366 to the Guideline Library window.

If the user selects the CHANGE Guideline Type 338 pushbutton, the system first displays 367 the guideline type pop-up list. The user then selects 368 the desired guideline type and the system changes 369 the guideline domain pop-up list to match the newly selected guideline type. Next, the guideline domain is set 370 to the first domain listed. The system then changes 371 the guideline intervention pop-up list to match the newly selected guideline type and domain and sets 372 the guideline intervention to the first intervention listed. The system then finds 373 the intervention for the specified guideline type and domain and published by a specified guideline developer. The system then queries 374 the user as to whether there is a guideline intervention available for the guideline developer. If there is not, the system displays 375 the guideline intervention information as a pushbutton. If there is, the system retrieves 376 the associated guideline information for the intervention and then displays 375 the guideline intervention information as a pushbutton. These steps are repeated for the second and third guideline developers, and control is returned 377 to the Guideline Library window.

If the user selects the CHANGE Guideline Domain 339 pushbutton, the system first displays 378 the guideline domain pop-up list. The user then selects 379 a guideline domain. The system then changes 380 the guideline intervention pop-up list to match the newly selected guideline domain and sets 381 the guideline intervention to the first intervention listed. Next, the system finds 382 the intervention for a specified guideline type and domain and published by a specified guideline developer and queries 383 the user as to whether there is a guideline intervention available for the guideline developer. If there is not, the system displays 384 the guideline intervention information as a pushbutton. If there is, the system retrieves 385 the associated guideline information for the intervention and then displays 384 the guideline intervention information as a pushbutton. These steps are repeated for the second and third guideline developers, and control is returned 386 to the Guideline Library window.

If the user selects the CHANGE Guideline Intervention 340 pushbutton, the system first displays 387 the guideline intervention pop-up list. The user then selects 388 a guideline intervention. The system then finds 389 the intervention for a specified guideline type and domain and published by a specified guideline developer and queries 390 the user as to whether there is a guideline intervention available for the guideline developer. If there is not, the system displays 391 the guideline intervention information as a pushbutton. If there is, the system retrieves 392 the associated guideline information for the intervention and then displays 391 the guideline intervention information as a pushbutton. These steps are repeated for the second and third guideline developers, and control is returned 393 to the Guideline Library window.

If the user selects the CHANGE Guideline Developer 341 pushbutton, the system first displays 394 the guideline developer pop-up list. The user then selects 395 a guideline developer. The system then finds 396 the intervention for a specified guideline type and domain that is published by a specified guideline developer and queries 397 the user as to whether there is a guideline intervention available for the guideline developer. If there is not, the system displays 399 the guideline intervention information as a pushbutton. If there is, the system retrieves 398 the associated guideline information for the intervention and then displays 399 the guideline intervention information as a pushbutton and returns 400 control to the Guideline Library window.

If the user selects the VIEW Corresponding Suggestion 343 pushbutton, the system first queries 401 the user as to whether there is a corresponding suggestion for the guideline. If there is not, control is returned 409 to the Guideline Library window. If there is, the system hides 402 the second and third guideline developer information panels. The system then finds and displays 403 a guideline recommendation in the recommendation panel, finds and displays 404 a guideline frequency in the recommendation panel, and finds and displays 405 a guideline decision tree prose statement in the recommendation panel. Next, the system queries 406 the user as to whether the user is ready to return to normal view and waits 407 for user input in response to the query. Once the user responds, the system clears and removes 408 the recommendation panel. The system then unhides 409 the second and third guideline developer panels and returns 410 control to the Guideline Library window.

If the user selects the VIEW Corresponding Health Risk Statement 344 pushbutton, the system first queries 411 the user as to whether there are any corresponding health risk statements for the guideline. If there is not, control is returned 412 to the Guideline Library window. If there is, the system hides 413 the second and third guideline developer information panels. The system then finds and displays 414 health risk statement(s) in the risk panel and finds and displays 415 guideline decision tree prose statement(s) in the risk panel. Next, the system queries 416 the user as to whether the user is ready to return to normal view and waits 417 for user input in response to the query. Once the user responds, the system clears and removes 418 the risk panel. The system then unhides 419 the second and third guideline developer panels and returns 412 control to the Guideline Library window.

If the user selects the VIEW Corresponding Patient Education Material 345 pushbutton, the system queries the user as to whether there are any corresponding patient education materials for the guideline. If there are not, control is returned 428 to the Guideline Library window. If there are, the system hides 421 the second and third guideline developer information panels. The system then finds and displays 422 patient education material(s) in the education panel and finds and displays 423 decision tree prose statement(s) in the education panel. Next, the system queries 424 the user as to whether the user is ready to return to normal view and waits 425 for user input in response to the query. Once the user responds, the system clears and removes 426 the education panel. The system then unhides 427 the second and third guideline developer panels and returns 428 control to the Guideline Library window.

If the user selects the CANCEL 346 pushbutton, the system clears and removes 429 the Guideline Library window and returns 430 control to the Main Menu window.

If the user selects the EDIT Guideline Information 342 pushbutton, the system first defines and displays 431 the Edit Guidelines window. The system then displays 432 the guideline developer with a pushbutton to change the developer, displays 433 the guideline type, displays 434 the guideline domain wit a scroll list for changing the domain, displays 435 the guideline intervention with a scroll list to change the intervention, and displays 436 sex and age classification data. Next, the system displays 437 a guideline reprint identifier with a pushbutton for changing the reprint identifier, displays 438 a guideline evidence reprint identifier with a pushbutton for changing the reprint identifier, displays 439 a guideline method reprint identifier with a pushbutton for changing the reprint identifier, displays 440 an evidence graded checklist box, and displays 441 an intervention graded checklist box. The system then displays a change year pushbutton 442, a Change Comment Section pushbutton 443, a Change General Prose pushbutton 444, a Change Selective Prose pushbutton 445, an OK pushbutton and a CANCEL pushbutton 446.

The system is then set up to edit the Guideline window 447. As part of this process, the system first waits for user input 448. The user must choose from among several pushbuttons. The options are: a CHANGE Source pushbutton 449, a CHANGE Guideline Type pushbutton 450, a CHANGE Guideline Intervention pushbutton 451, a CHANGE Age-Sex Classification pushbutton 452, a CHANGE Guideline Reference Reprint Identifier pushbutton 453, a CHANGE Evidence Reference Identifier 454, a CHANGE Method Reference Identifier 455, a CHANGE Evidence Graded pushbutton 456, a CHANGE Recommendation Graded pushbutton 457, a CHANGE Publish, Approval, and Expiration Dates pushbutton 458, a CHANGE Comment Section pushbutton 459, a CHANGE General Description pushbutton 460, a CHANGE Selective Description pushbutton 461, an OK pushbutton 462, and a CANCEL pushbutton 463.

If the user selects the CHANGE Source pushbutton 449, the system displays a guideline developer pop-up list 464. The user then selects a new guideline developer 465, the system displays a revised guideline developer with a change pushbutton 466, and control is returned to the Edit Guideline window 467.

If the user selects the CHANGE Guideline Type pushbutton 450, the system displays a guideline type scroll list 468. The user then reclassifies the guideline type 469, the system displays a revised guideline type with a change pushbutton 470, and control is returned to the Edit Guideline window 471.

If the user selects the CHANGE Guideline Intervention pushbutton 451, the system displays a guideline intervention scroll list 472. The user then changes the guideline intervention 473, the system displays a revised guideline intervention with a change pushbutton 474, and control is returned to the Edit Guideline window 475.

If the user selects the CHANGE Age-Sex Classification pushbutton 452, the user then selects a new age and sex classification using a radio box and get fields 476. The system then displays the revised guideline classification data with a change pushbutton 477, and control is returned to the Edit Guideline window 478.

If the user selects the CHANGE Guideline Reference Reprint Identifier pushbutton 453, the system displays the reference reprint pop-up list 479. The user then selects a new guideline reprint identifier 480, the system displays the revised reprint identifier with a change pushbutton 481, and control is returned to the Edit Guideline window 482.

If the user selects the CHANGE Evidence Reference Identifier 454, the system displays the reference reprint pop-up list 483. The user then selects a new evidence reprint identifier 484, the system displays the revised reprint identifier with a change pushbutton 485, and control is returned to the Edit Guideline window 486.

If the user selects the CHANGE Method Reference Identifier 455, the system displays the reference reprint pop-up list 487. The user then selects a new method reprint identifier 488, the system displays a revised reprint identifier with a change pushbutton 489, and control is returned to the Edit Guideline window 490.

If the user selects the CHANGE Evidence Graded pushbutton 456, the user indicates whether the evidence has been graded 491 and control is returned to the Edit Guideline window 492.

If the user selects the CHANGE Recommendation Graded pushbutton 457, the user indicates whether the recommendation has been graded 493 and control is returned to the Edit Guideline window 494.

If the user selects the CHANGE Publish, Approval, and Expiration Dates pushbutton 458, the system defines and displays the Year window 495, displays the year the guideline was written, the year the guideline was approved, and the year the guideline will expire, for editing purposes 496. The user then changes the year the guideline was written, the year the guideline was approved, and/or the year the guideline will expire, as appropriate 497. The system then asks the user to confirm any changes made 498. If the user does not confirm the changes, the system clears and removes the Year window 499 and control is returned to the Edit Guideline window 501. If the user does confirm changes, the system saves the changes temporarily 500, clears and removes the Year window 499, and returns control to the Edit Guideline window 501.

If the user selects the CHANGE Comment Section pushbutton 459, the system defines and displays the Comment window 502 and displays the comment for editing purposes 503. The user then changes the comment 504. The system then asks the user to confirm any changes made 505. If the user does not confirm the changes, the system clears and removes the Comment window 507 and control is returned to the Edit Guideline window 508. If the user does confirm changes, the system saves the changes temporarily 506, clears and removes the Comment window 507, and returns control to the Edit Guideline window 508.

If the user selects the CHANGE General Description pushbutton 460, the system defines and displays the General window 509 and displays the guideline general criteria prose for editing purposes 510. The user then changes the guideline general criteria prose 511. The system then asks the user to confirm any changes made 512. If the user does not confirm the changes, the system clears and removes the General window 514 and control is returned to the Edit Guideline window 515. If the user does confirm changes, the system saves the changes temporarily 513, clears and removes the General window 514, and returns control to the Edit Guideline window 515.

If the user selects the CHANGE Selective Description pushbutton 461, the system defines and displays the Selective window 516 and displays the guideline selective criteria prose for editing purposes 517. The user then changes the guideline selective criteria prose 518. The system then asks the user to confirm any changes made 519. If the user does not confirm the changes, the system clears and removes the Selective window 521 and control is returned to the Edit Guideline window 522. If the user does confirm changes, the system saves the changes temporarily 520, clears and removes the Selective window 521, and returns control to the Edit Guideline window 522.

If the user selects the OK pushbutton 462, all confirmed changes are saved permanently. The system updates the system database files with revised guideline information 523 and updates the date and user last edited guideline fields with the current date and user 524. The system then clears and removes the Edit Guideline window 525 and control is returned to the Guideline Library window 526.

If the user selects the CANCEL pushbutton 463, the system clears and removes the Edit Guideline window 527 and control is returned to the Guideline Library window 528.

Referring to FIGS. 53–75, the Rules Editor feature 32 of the present invention is described. First, the necessary databases are opened 600. The Rules Library database is opened 601, as is the Health Risk database 602, the Suggestion database 603, the Patient Education database 604, the Questionnaire database 605, and the Report Format database 606. Next, the Rules Library, Health Risk, Suggestion, and Patient Education databases are indexes on the rule identifier 607 and on the rule order 608. The Health Risk, Suggestion, and Patient Education databases are then indexed on the format group identifier 609. The Report Layout database is indexed on the format group identifier 610 and the Questionnaire database is indexed on a unique question identifier 611. The Rules Library, Health Risk, Suggestion, and Patient Education databases are then cross referenced on the rule identifier 612 and on the rule order 613. Finally, the Health Risk, Suggestion, Patient Education, and Report Layout databases are cross referenced on the format group identifier 614.

Next, the system creates pop-up lists 615. First, the system creates a group format pop-up list for the Health Risk, Suggestion, and Patient Education available format groups 616. Guideline type, domain, and intervention pop-up lists are then created 617, followed by category, subcategory, and keyword pop-up lists 618 and CPT and ICD code pop-up lists 619.

The system then defines the appropriate windows 620. The Rule Editor window is defined 621, followed by the Edit Feedback window 622, the Report Format window 623, the Audit Report window 624, and the Feedback Editor window 625. These windows will be used to enter data into the system.

Next, pushbuttons to be used in the Rules Editor window are displayed 626. These pushbuttons are: the rule number pushbutton 627, the rule order pushbutton 628, the format pushbutton 629, the priority (high, low, usual, N/A) pushbutton 630, the readiness (high, usual, N/A) pushbutton 631, the filter pushbutton 632, the report type pushbutton 633, the add pushbutton 634, and the remove pushbutton 635.

The Display Feedback Routine is now performed 636. The user is now presented with three options: to display the Health Risk Feedback (which is the default choice on start-up) 637, to display the Suggestion Feedback 638, or to display the Patient Education Feedback 639.

If the user opts to display the Health Risk Feedback 637, the heading is first displayed 640, along with the date the health risk statement was written 641, the date the health risk statement was last updated 642, a feedback note (regarding the health risk statement) 643, a category classification 644, a subcategory classification 645, the date the applicable rule was written 646, the date the rule was last updated 647, and the rule in prose form 648. Other information is displayed on a pushbutton. For example, the rule number is displayed on the rule number pushbutton 649. Likewise, the rule order 650, the group format numbers 651, the priority rating 652, and the readiness indicator 653 are all displayed on the corresponding pushbutton. Control is then returned 654 to the call routine.

If the user chooses to display the Suggestion Feedback 638, the appropriate heading is displayed 655, along with the recommended frequency 656, the date the suggestion was written 657, the date the suggestion was last updated 658, a feedback note relative to the suggestion 659, a footnote by the physician 660, a guideline intervention 661, a guideline type classification 662, a guideline domain classification 663, a keyword classification 664, the date the applicable rule was written 665, the date the rule was last updated 666, and the rule in prose form 667. Other information is displayed on a pushbutton. For example, the rule number is displayed on the rule number pushbutton 668. Likewise, the rule order 669, the group format numbers 670, the priority rating 671, and the readiness indicator 672 are all displayed on the corresponding pushbutton. Control is then returned 673 to the call routine.

If the user chooses to display the Patient Education Feedback 639, the appropriate heading is displayed 674, along with the date the patient education materials were written 675, the date the patient education materials were last updated 676, a feedback note relative to patient education 677, a category classification 678, a subcategory classification 679, a keyword classification 680, the date the applicable rule was written 681, the date the rule was last updated 682, and the rule in prose form 683. Other information is displayed on a pushbutton. For example, the rule number is displayed on the rule number pushbutton 684. Likewise, the rule order 685, the group format numbers 686, the priority rating 687, and the readiness indicator 688 are all displayed on the corresponding pushbutton. Control is then returned 689 to the call routine.

After returning control to the call routine 654, 673, or 689, the edit region around the feedback (health risk, suggestion, patient education) window is defined and displayed 690, as is the edit region around the rule (health risk, suggestion, patient education) window 691. The system then waits for user input 692.

The choices presented to the user for input are: FIND the rule using the rule number 693; FIND the rule using the rule order 694; CHANGE the priority rating 695; CHANGE the readiness indicator 696; FORMAT, EDIT the format group 697; FORMAT, ASSIGN the format group 698; FORMAT, REMOVE the format group 699; FORMAT, ADD to the format group 700; FILTER 701; CHANGE the report type 702; AUDIT 703; EDIT FEEDBACK 704, and EDIT FEEDBACK RULE 705.

If the user chooses to find a rule using the rule number 693, the user enters the rule number 706. The system checks to ensure that the rule number exists 707. If it does, control is returned to the Edit Feedback window 708. If it does not exist, the last rule number is found 709 and the display feedback routine previously described is performed 710. After control is returned from the display feedback routine, control is returned to the Edit Feedback window 708.

If the user choses to find a rule using the rule order 694, the user enters the rule order 711. The system checks to ensure that the rule order exists 712. If it does, control is returned to the Edit Feedback window 713. If it does not exist, the last rule order is found 714 and the display feedback routine previously described is performed 715. After control is returned from the display feedback routine, control is returned to the Edit Feedback window 713.

If the user chooses to change the priority rating 695, the priority rating toggle (High, Low, Usual, N/A) is displayed 714. The user then selects a new priority rating 715, and the system displays the revised priority rating 716. Control is then returned to the Edit Feedback window 717.

If the user chooses to change the readiness indicator 696, the readiness indicator toggle (High, Low, Usual, N/A) is displayed 718. The user then selects a new readiness indicator 719, and the system displays the revised readiness indicator 720. Control is then returned to the Edit Feedback window 721.

If the user chooses to assign the format group 698, the system first displays the group format pop-up list (Health Risk, Suggestion, or Patient Education, depending on the edit mode) 722. The user then selects the group format 723 and the system displays the report feedback type (note or footnote) 724. The user then selects the feedback type 725 and the system changes and displays the group format for the selected feedback type 726. Control is then returned to the Edit Feedback window 727.

If the user chooses to remove the format group 699, the system first displays the group format pop-up list (Health Risk, Suggestion, or Patient Education, depending on the edit mode) 737. The user then selects the group format 738 and the system displays the report feedback type (note or footnote) 739. The user then selects the feedback type 740 and the system removes the selected group format from the format group pop-up list 741 and removes all feedback that uses this group format 742. Control is then returned to the Edit Feedback window 743.

If the uses chooses to add a format group 700, the user enters the group title 744, the description 745, the format width specification 746, and the format height specification 747. The user is then asked if the new format group is to be saved 748. If not, control is returned to the Edit Feedback window 749. If it is to be saved, the new format group is added to the format group pop-up list 750. The user is then queried as to whether the current format should be replaced with the new group format 751. If not, control is returned to the Edit Feedback window 749. If so, the current format is changed to the new group format 752 and then control is returned to the Edit Feedback window 749.

If the user chooses to edit the format group 697, the system displays 753 the Report Format window and queries 754 the user as to whether the note format or the footnote format will be changed. If the note format is to be changed, the system displays the note format group title 755, the note format description 756, the note fromat width specification 757, and the note format height specification 758. If the footnote format is to be changed, the system displays the footnote format group title 759, the footnote format description 760, the footnote fromat width specification 761, and the footnote format height specification 762.

After the note or footnote format parameters are displayed, the system waits for further user input 763. At this point, the user has four options: CHANGE Format Group Title 764, CHANGE Description 765, CHANGE Format Width Specification 766, or CHANGE Format Height Specification 767.

If the user opts to change the format group title 764, the user enters a new format group title and describes the feedback to follow 768. The system asks if the user wishes to save the changes 769. If not, control is returned to the Edit Feedback window 770. If so, the format group title field is changed to the revised title 771 and control is returned to the Edit Feedback window 770.

If the user opts to change the description 765, the user enters a new description 772. The system asks if the user wishes to save the changes 773. If not, control is returned to the Edit Feedback window 774. If so, the description field is changed to the revised description 775 and control is returned to the Edit Feedback window 774.

If the user opts to change the format width specification 766, the user enters a new format width, which determines the maximum report print width for the current group 776. The system asks if the user wishes to save the changes 777. If not, control is returned to the Edit Feedback window 778. If so, the format width field is changed to the revised width 779 and control is returned to the Edit Feedback window 778.

If the user opts to change the format height specification 767, the user enters a new format height, which determines the maximum report print height for the current group 780. The system asks if the user wishes to save the changes 781. If not, control is returned to the Edit Feedback window 782. If so, the format height field is changed to the revised height 783 and control is returned to the Edit Feedback window 782.

If the user chooses FILTER 701 from the Rules Editor window, the system displays the report format pop-up list 784 for the appropriate edit mode. The user then selects a report format 785 and the system filters the appropriate feedback database based on the selected report format 786. Control is then returned to the Edit Feedback window 787 and the feedback report is displayed only for the selected report format 788.

If the user chooses change report type 702 from the Rules Editor window, the user is presented with three options: HEALTH RISK Feedback 789, SUGGESTION Feedback 790, and PATIENT EDUCATION Feedback 791.

If the user opts for HEALTH RISK Feedback 789, the system displays 792 the Edit Report Type toggle. The user then selects the Health Risk Report type 793 and the system stores the present settings (current feedback, filter status, and filter report format) 794. The system then retrieves and sets the settings to the settings last used when the Health Risk feedback was edited 795. The Display Feedback Routine, as previously described, is then performed as it relates to the Health Risk mode 796. Control is then returned to the Edit Feedback window 797.

If the user opts for SUGGESTION Feedback 790, the system displays 798 the Edit Report Type toggle. The user then selects the Suggestion Report type 799 and the system stores the present settings (current feedback, filter status, and filter report format) 800. The system then retrieves and sets the settings to the settings last used when the Suggestion feedback was edited 801. The Display Feedback Routine, as previously described, is then performed as it relates to the Suggestion mode 802. Control is then returned to the Edit Feedback window 803.

If the user opts for PATIENT EDUCATION Feedback 791, the system displays 804 the Edit Report Type toggle.

The user then selects the Patient Education Report type 805 and the system stores the present settings (current feedback, filter status, and filter report format) 806. The system then retrieves and sets the settings to the settings last used when the Patient Education feedback was edited 807. The Display Feedback Routine, as previously described, is then performed as it relates to the Patient Education mode 808. Control is then returned to the Edit Feedback window 809.

If the user chooses AUDIT 703 from the Rules Editor window, the system displays the audit report window 810 and performs a series of verifications and displays the results. The system verifies that all feedback classifications match standardized lexicons 811, that all rule identifier numbers are valid 812, that all rule risk identifier names are valid 813, that all rule question references are valid 814, that all rule observed data references are valid 815, and that all feedback has been assigned a format group 816. The user is then queried as to whether the report should be printed 817. If not, control is returned to the Risk Factor window 818. If so, the system prints the audit result with a header identifying the date and time at which the audit was performed 819 and then control is returned to the Risk Factor window 818.

If the user chooses to edit the feedback 704, the Edit Feedback routine is performed 820 and control is returned to the risk factor window 822. The system begins the Edit Feedback routine by waiting for user input 821. The user at this point has the following options: CHANGE Heading 823, CHANGE Priority Rating (Suggestion Only) 824, CHANGE Readiness Indicator (Suggestion Only) 825, CHANGE Frequency (Suggestion Only) 826, CHANGE Note Feedback 827, CHANGE Note Feedback Format Group 828, CHANGE Feedback Footnote (Suggestion Only) 829, CHANGE Feedback Footnote Format Group (Suggestion Only) 830, CHANGE ICD Code (Health Risk Only) 831, CHANGE CPT Code (Suggestion Only) 832, SAVE 833, and CANCEL 834.

If the user opts to change the heading 823, the system performs an Edit Feedback routine 835. The Display Edit Feedback routine brings up a Feedback Editor window 837 that displays a number of items. The window displays a heading 838, as well as a priority rating 839, a frequency 840, a note feedback 841, a note feedback format group 842, a footnote 843, a footnote feedback format group 844, an ICD code 845, a CPT code 846, and OK and Cancel pushbuttons 847, where applicable. Control is then returned to the call routine 848. The user then enters the revised heading 849. The system asks whether the changes are to be saved 850. If not, control is returned to the Feedback Editor window 851. If so, the heading display is changed to the revised heading 852 and control is returned to the Feedback Editor window 851.

If the user opts to change the priority rating 824, the system performs the Edit Feedback routine 853 previously described. Control is then returned to the call routine 848. The system then displays the priority rating toggle (High, Low, Usual) 854. The user selects a new priority rating 855, and the system displays 856 the revised priority rating and returns control 857 to the Feedback Editor window.

If the user opts to change the readiness indicator 825, the system performs the Edit Feedback routine 858 previously described. Control is then returned to the call routine 848. The system then displays the readiness indicator toggle (High, Low, Usual) 859. The user selects a new readiness indicator 860, and the system displays 861 the revised readiness indicator and returns control 862 to the Feedback Editor window.

If the user opts to change the frequency 826, the system performs the Edit Feedback routine 863 previously described. Control is then returned to the call routine 848. The user then enters the revised frequency 864. The system asks whether the changes are to be saved 865. If not, control is returned to the Feedback Editor window 866. If so, the frequency display is changed to the revised frequency 867 and control is returned to the Feedback Editor window 866.

If the user opts to change the note feedback 827, the system performs the Edit Feedback routine 868 previously described. Control is then returned to the call routine 848. The user then enters the revised note feedback 869. The system asks whether the changes are to be saved 870. If not, control is returned to the Feedback Editor window 871. If so, the note feedback field is changed to the revised note 872 and control is returned to the Feedback Editor window 871.

If the user opts to change the note feedback format group 828, the system performs the Edit Feedback routine 872 previously described. Control is then returned to the call routine 848. The system then displays the group format pop-up list relative to the appropriate mode 873. The user selects a revised format group 874, and the system changes the note feedback format group field to the revised group 875, displays 876 the revised note format group, and returns control 877 to the Feedback Editor window.

If the user opts to change the feedback footnote 829, the system performs the Edit Feedback routine 878 previously described. Control is then returned to the call routine 848. The user then enters the revised footnote feedback 879. The system asks whether the changes are to be saved 880. If not, control is returned to the Feedback Editor window 881. If so, the footnote feedback field is changed to the revised footnote 882 and control is returned to the Feedback Editor window 881.

If the user opts to change the feedback footnote format group 830, the system performs the Edit Feedback routine 882 previously described. Control is then returned to the call routine 848. The system then displays the group format pop-up list relative to the appropriate mode 883. The user selects a revised format group 884, and the system changes the footnote feedback format group field to the revised group 885, displays 886 the revised footnote format group, and returns control 887 to the Feedback Editor window.

If the user opts to change the ICD code 831, the system performs the Edit Feedback routine 888 previously described. Control is then returned to the call routine 848. The system then displays the ICD Code pop-up list 889. The user selects a revised ICD code 890, and the system changes the ICD code field to the revised code 891, displays 892 the revised ICD code, and returns control 893 to the Feedback Editor window.

If the user opts to change the CPT code 832, the system performs the Edit Feedback routine 894 previously described. Control is then returned to the call routine 848. The system then displays the CPT Code pop-up list 895. The user selects a revised CPT code 896, and the system changes the CPT code field to the revised code 897, displays 898 the revised CPT code, and returns control 899 to the Feedback Editor window.

If the user opts to save, the system saves the feedback changes 900 and returns control to the call procedure 901, that is, to the Edit Feedback window.

If the user opts to cancel, the system returns control to the call procedure 902, that is, to the Edit Feedback window.

If the user chooses to edit the feedback rule 705 from the Rules Editor window, the system performs an Edit Feedback Rule Routine 903 and then returns control to the Risk Factor window 904. The system begins the Edit Feedback Rule routine by waiting for user input 905. The user is presented with the following options: CHANGE guideline type classification 906, CHANGE guideline domain 907, CHANGE guideline intervention 908, CHANGE category classification 909, CHANGE subcategory classification 910, CHANGE keywords 911, and EDIT Rule feature 912.

If the user opts to change the guideline type classification 906, the system performs a Suggestions Edit Feedback Rule routine 913. The Edit Feedback Rule routine 913 causes the system to present a Feedback Rules Editor window 922, which displays a number of items, including a guideline type 923, a guideline domain 924, a guideline intervention 925, comments 926, a rule in prose form 927, an edit rule pushbutton 928, and OK and Cancel pushbuttons 929. Control is then returned to the call routine 930, in this case the change guideline type classification routine 906. The system then displays the guideline type pop-up list 914. The user selects the guideline type classification 915, and the system changes the guideline domain pop-up list to match the newly selected guideline type 916. The system then sets the guideline domain to the first domain listed 917, changes the guideline intervention pop-up list to match the newly selected guideline type and domain 918, sets the guideline intervention to the first intervention listed 919, reminds the user that the guideline domain and the intervention classifications have changed 920, and returns control to the Feedback Rule Editor window 921.

If the user opts to change the guideline domain 907, the system calls 931 the Suggestion Edit Feedback Rule routine previously described. On return from that routine, the system displays the guideline domain pop-up list 932. The user selects the guideline domain classification 933, and the system changes the guideline intervention pop-up list to match the newly selected guideline domain 934. The system then sets the guideline intervention to the first intervention listed 935, reminds the user that the guideline intervention classification has changed 936, and returns control to the Feedback Rule Editor window 937.

If the user opts to change the guideline intervention 908, the system calls 938 the Suggestion Edit Feedback Rule routine previously described. On return from that routine, the system displays the guideline intervention pop-up list 939. The user selects the guideline intervention classification 940, and control is returned to the Feedback Rule Editor window 941.

If the user opts to change the category classification 909, the system calls the Health Risk, Patient Education Edit Feedback Rule routine 942. This Edit Feedback Rule routine 942 causes the system to present a Rules Editor window 949, which displays a number of items, including a category classification 950, a subcategory classification 951, comments 952, a rule in prose form 953, an edit rule pushbutton 954, and OK and Cancel pushbuttons 955. Control is then returned to the call routine 956, in this case the change category classification routine 909. The system then displays the category pop-up list 943. The user selects the category classification 944, and the system changes the subcategory pop-up list to match the newly selected category 945. The system then sets the subcategory to the first intervention listed 946, reminds the user that the subcategory classification has changed 947, and returns control to the Feedback Rule Editor window 948.

If the user opts to change the subcategory classification 910, the system calls 949 the Health Risk, Patient Education Edit Feedback Rule routine previously described. The system then displays the subcategory pop-up list 950. The user selects the subcategory classification 951, and the system returns control to the Feedback Rule Editor window 952.

If the user opts to change the keywords 911, the system calls 953 the Health Risk, Patient Education, and Suggestions Edit Feedback Rule routines previously described. The system then displays the keyword pop-up list 954. The user selects the keyword classification(s) 955, and the system returns control to the Feedback Rule Editor window 956.

If the user opts to edit the rule feature 912, the system finds and stores 957 the lookup variable prose (observed name, reported text, score name) to the clause variable. The system also finds and stores 958 the relational operator (=, >, <, <>) prose to the clause variable. The system then stores the compare-to-answer (number, questionnaire response, risk score) 959 and the logical operator (and, or, end) 960 to the clause variable and displays 961 the current clause variable as a pushbutton. The system then checks for a logical end 962 to determine if all rule clauses have been edited (a rule can be up to 15 clauses long). If not, the entire process is repeated for all rule clauses.

If all rule clauses have been edited, the first rule clause is displayed 963. First, the system displays the lookup variable as a pushbutton 964. The system then displays the relational operator pushbutton list 965, the compare-to-answer as a pushbutton list 966, and the logical operator pushbutton list 967.

The system then displays the edit clause pushbuttons 968. These pushbuttons include an insert pushbutton 969, a clear pushbutton 970, a move pushbutton 971, and save and cancel pushbuttons 972.

The system then creates a temporary rule 973. The system first creates a clause array (15,4) dimension 974. The system then copies each rule clause to an array 975. The user will modify the array and can permanently change a rule by selecting the Save pushbutton. The system then waits for user input 976.

At this point, the user is presented with numerous options. These options are: CHANGE current edit clause 977, INSERT new rule clause 978, CLEAR current rule clause 979, MOVE current rule clause 980, CHANGE current lookup variable (observed) 981, CHANGE current lookup variable (reported) 982, CHANGE current lookup variable (risk score) 983, CHANGE current relational operator 984, CHANGE current compare-to-answer (observed data) 985, CHANGE current compare-to-answer (reported data) 986, CHANGE current compare-to-answer (risk score data) 987, CHANGE current logical operator 988, SAVE 989, and CANCEL 990.

If the user opts to change the current edit clause 977, the user selects a clause pushbutton to edit 991. The system then displays the lookup variable as a pushbutton 992, displays the relational operator pushbutton list 993, displays the compare-to-answer as a pushbutton list 994, displays the logical operator pushbutton list 995, and returns control to the Rule Editor window 996.

If the user opts to insert a new rule clause 978, the user enters the new clause 997, which may be a lookup variable, a relational operator, a compare-to-answer, or a logical operator. The system then asks the user if the new clause is to be saved 998. If so, the system increments succeeding clause numbers by 1 999, inserts the new clause into the rule 1000, and returns control to the Rule Editor window 1001.

If the user opts to clear the current rule clause 979, the current edit clause data is first removed from the rule 1002. The system then queries the user as to whether the current edit clause is the last clause in the rule 1003. If not, succeeding clause numbers are decremented by 1 1004 in order to compact the rule. The current edit clause is then changed 1006 and control is returned to the Rule Editor window 1007. If the current edit clause is the last clause in the rule, the logical operator of the previous clause is changed to END 1005. The current edit clause is then changed 1006 and control is returned to the Rule Editor window 1007.

If the user opts to move the current rule clause 980, the user selects the clause pushbutton corresponding to the clause after which the current clause will be inserted 1008. The system then queries the user as to whether the current edit clause number comes before the move clause number 1009. If not, clause numbers between the current edit clause number and the move position number are incremented by 1 1010 and control is returned to the Rule Editor window 1011. If the current edit clause number comes before the move clause number, clause numbers between the current edit clause number and the move position number are decremented by 1 1012 and control is returned to the Rule Editor window 1011.

If the user opts to change the current observed lookup variable 981, the system displays the observed data pop-up list 1013. The user then selects a lookup variable 1014 and the system displays the lookup variable 1015. The system then sets the compare-to-answer to NONE 1016, reminds the user to change the compare-to-answer 1017, and returns control to the Rule Editor window 1018.

If the user opts to change the current reported lookup variable 982, the system displays the reported data pop-up list 1019. The user then selects a reported data 1020 and the system displays the reported data 1021. The system then queries the user as to whether the lookup variable changed from one reported data to another 1022. If so, control is returned to the Rule Editor window 1023. If not, the system sets the compare-to-answer to NONE 1024, reminds the user to change the compare-to-answer 1025, and returns control to the Rule Editor window 1023.

If the user opts to change the current risk score lookup variable 983, the system displays the risk score pop-up list 1024. The user then selects a risk score 1025 and the system displays the risk score 1026. The system then queries the user as to whether the lookup variable changed from one risk score to another 1027. If so, control is returned to the Rule Editor window 1028. If not, the system sets the compare-to-answer to NONE 1029, reminds the user to change the compare-to-answer 1030, and returns control to the Rule Editor window 1028.

If the user opts to change the current relational operator 984, the system displays the relational operator pop-up list 1031. The user then selects a new relational operator 1032 and the system displays the new relational operator 1033. Control is then returned to the Rule Editor window 1034.

If the user opts to change the current observed data compare-to-answer 985, the system displays the observed data window 1035, displays the observed data information 1036, and either enters a new observed data value or selects a new observed data answer 1037. The new observed data value or answer is then displayed 1038 and control is returned to the Rule Editor window 1039.

If the user opts to change the current reported data compare-to-answer 986, the system displays a reported data window 1040 as well as all possible reported data responses depending on the reported data type 1041. The user then selects a new reported data response 1042, and the new reported data response is displayed 1043 and control is returned to the Rule Editor window 1044.

If the user opts to change the current risk score data compare-to-answer 987, the system first displays a risk score data window 1045 as well as risk score information 1046. A new risk score value is entered 1047, the new risk score value is displayed 1048, and control is returned to the Rule Editor Window 1049.

If the user opts to change the current logical operator 988, the system first displays a logical operator pop-up list 1050. The user then selects a new logical operator 1051, and the new logical operator is displayed 1052 before control is returned to the Rule Editor window 1053.

If the user opts to save 989, the rule field is changed in the Rule database based on changes found in the clause array 1054. Control is then returned to the Edit Feedback Rule window 1055 and the revised rule is displayed in the Edit Feedback Rule window 1056.

If the user opts to cancel 990, the Rule Editor window is deactivated 1057 and control is returned to the Edit Feedback Rule window 1058.

Referring to FIGS. 76–81, the Risk Score Editor feature 1100 is described. First, the appropriate databases are opened 1101, including the Risk Factor database 1102, the Risk Score Identifier database 1103, and the Questionnaire database 1104. Next, the Risk Factor database is indexed on the identifier and question identifier fields 1105, the Risk Identifier database is indexed on the identifier fields 1106, and the Questionnaire database is indexed on the unique question identifier 1107. Finally, the risk identifier and the question identifier are cross referenced among the Risk Factor, the Risk Identifier, and the Questionnaire databases 1108.

Next, the Risk Identifier window is defined and displayed 1109. The risk identifier number is displayed 1110, along with the risk identifier name 1111, the risk interpretation prose 1112, and the risk baselines 1113. The edit region around the risk identifier name and the interpretation window are defined and displayed 1114, and the add risk score 1115 and remove risk score 1116 pushbuttons are displayed.

The Risk Factor window is then defined and displayed 1117. The question text or the observed data is displayed 1118, along with the risk factor weights 1119, the edit pushbutton for each risk factor 1120, and the add risk factor 1121, remove risk factor 1122, and audit 1123 pushbuttons.

The system then displays the Move pushbuttons 1124, including the next risk score 1125, last risk score 1126, scroll next risk factor 1127, and scroll previous risk factor 1128 pushbuttons.

Next, the optional windows are defined 1129, including the Risk Identifier window 1130, the Risk Factor window 1131, and the Audit Report window 1132. The system then waits for user input 1133.

At this point, several options are available to the user, including DISPLAY next risk score data 1134, DISPLAY previous risk score data 1135, SCROLL to next risk factor 1136, SCROLL to previous risk factor 1137, CHANGE risk score identifier number 1138, CHANGE risk score identifier variable 1139, CHANGE risk score LOW baseline value and interpretation 1140, CHANGE risk score HIGH baseline value and interpretation 1141, ADD risk factor 1142, EDIT risk factor weights 1143, REMOVE risk factor 1144, and AUDIT risk factor and risk identifier databases 1145.

If the user chooses to display the next risk score data 1134, the system first checks whether the current risk score is the last risk score 1146. If it is, control is returned to the Risk Factor window 1147. If not, the system finds the next risk score identifier 1148, retrieves and displays the risk identifier data in the Risk Identifier window 1149, retrieves and displays the risk factor data in the Risk Factor window 1150, and returns control to the Risk Factor window 1147.

If the user chooses to display the previous risk score data 1135, the system first checks whether the current risk score is the first risk score 1151. If it is, control is returned to the Risk Factor window 1152. If not, the system finds the previous risk score identifier 1153, retrieves and displays the risk identifier data in the Risk Identifier window 1154, retrieves and displays the risk fator data in the Risk Factor window 1155, and returns control to the Risk Factor window 1152.

If the user chooses to scroll to the next risk factor 1136, the system first checks whether the last displayed risk factor is the last risk factor 1156. If it is, control is returned to the Risk Factor window 1157. If not, the system finds the next risk factor 1158, retrieves and displays the question text or observed data 1159, retrieves and displays the weights for the risk factor 1160, displays an edit pushbutton for each risk factor 1161, and returns control to the Risk Factor window 1157.

If the user chooses to scroll to the previous risk factor 1137, the system first checks whether the current risk factor is the first risk factor 1162. If it is, control is returned to the Risk Factor window 1163. If not, the system finds the previous risk factor 1164, retrieves and displays the question text or observed data 1165, retrieves and displays weights for the risk factor 1166, displays an edit pushbutton for each risk factor 1167, and returns control to the Risk Factor window 1163.

If the user chooses to change the risk score identifier number 1138, the system displays a Risk Identifier Editor window 1168 and changes the risk identifier number 1169. The system then asks the user if the changes are to be saved 1170. If not, the Risk Identifier Editor window is deactivated and any changes are displayed 1171. Control is then returned to the Risk Factor window 1172. If changes are to be saved, the system changes the risk identifier number in the Risk Identifier database 1173 and changes all corresponding risk identifier numbers in the Risk Factor database to a revised identifier number 1174. The Risk Identifier Editor window is deactivated and any changes are displayed 1171. Control is then returned to the Risk Factor window 1172.

If the user chooses to change the risk score identifier variable 1139, the system displays a Risk Identifier Editor window 1175 and changes the risk identifier variable 1176. The system then asks the user if the changes are to be saved 1177. If not, the Risk Identifier Editor window is deactivated and any changes are displayed 1178. Control is then returned to the Risk Factor window 1179. If changes are to be saved, the system changes the risk variable identifier in the Risk Identifier database 1180 and changes all corresponding risk identifier variable references in the Rule database to a revised variable 1181. The Risk Identifier Editor window is deactivated and any changes are displayed 1178. Control is then returned to the Risk Factor window 1179.

If the user chooses to change the risk score low baseline value 1140, the system displays a Risk Identifier Editor window 1182 and changes the low baseline value and interpretation messages 1183. The system then asks the user if the changes are to be saved 1184. If not, the Risk Identifier Editor window is deactivated and any changes are displayed 1185. Control is then returned to the Risk Factor window 1186. If changes are to be saved, the system changes the low baseline value and interpretation messages in the Risk Identifier database 1187. The Risk Identifier Editor window is deactivated and any changes are displayed 1185. Control is then returned to the Risk Factor window 1186.

If the user chooses to change the risk score high baseline value 1141, the system displays a Risk Identifier Editor window 1188 and changes the high baseline value and interpretation messages 1189. The system then asks the user if the changes are to be saved 1190. If not, the Risk Identifier Editor window is deactivated and any changes are displayed 1191. Control is then returned to the Risk Factor window 1192. If changes are to be saved, the system changes the high baseline value and interpretation messages in the Risk Identifier database 1193. The Risk Identifier Editor window is deactivated and any changes are displayed 1191. Control is then returned to the Risk Factor window 1192.

If the user chooses to add a risk factor 1142, the system displays a Risk Factor Editor window 1194 and adds the risk factor 1195. The system then asks the user if the changes are to be saved 1196. If not, the Risk Factor window is deactivated and any changes are displayed 1197. Control is then returned to the Risk Factor window 1198. If changes are to be saved, the system adds the risk factor to the Risk Factor database 1199 and reminds the user that the baseline values may need to be changed 1200. The Risk Factor window is deactivated and any changes are displayed 1197. Control is then returned to the Risk Factor window 1198.

If the user chooses to edit the risk factor weights 1143, the system displays a Risk Factor Editor window 1201 and changes the risk factor weights 1202. The system then asks the user if the changes are to be saved 1203. If not, the Risk Factor window is deactivated and any changes are displayed 1204. Control is then returned to the Risk Factor window 1205. If changes are to be saved, the system changes the risk factor weights in the Risk Factor database 1206 and reminds the user that the baseline values may need to be changed 1207. The Risk Factor window is deactivated and any changes are displayed 1204. Control is then returned to the Risk Factor window 1205.

If the user chooses to remove a risk factor 1144, the system displays a Risk Factor Editor window 1208 and removes the risk factor 1209. The system then asks the user if the changes are to be saved 1210. If not, the Risk Factor window is deactivated and any changes are displayed 1211. Control is then returned to the Risk Factor window 1212. If changes are to be saved, the system removes the risk factor from the Risk Factor database 1213 and reminds the user that the baseline values may need to be changed 1214. The Risk Factor window is deactivated and any changes are displayed 1211. Control is then returned to the Risk Factor window 1212.

If the user chooses to audit the risk factor and risk identifier databases 1145, the system first displays an Audit Report window 1215. The system then verifies that all question references are valid and displays the results 1216, verifies that all risk identifier numbers are valid and displays the results 1217, and verifies that all risk identifiers have baseline low-high values and interpretation messages and displays the results 1218. The system then asks the user if the Audit Report is to be printed 1219. If not, control is returned to the Risk Factor window 1220. If the report is to be printed, the system prints the audit result with a header identifying the date and time at which the audit was performed 1221 and returns control to the Risk Factor window 1220.

Referring to FIGS. 82 and 83, a system Guidelines listing is shown. The heading shows that all categories and subcategories have been selected, and that the topic for the Guideline Listing is blood pressure measurement. References are listed and the guideline associated with each reference are presented. Rules and algorithms pertaining to blood pressure measurement are also listed.

Referring to FIGS. 84 and 85, a system Risk Score listing is shown. As shown, this form shows risk scores for various behaviors relating to the cardiovascular system, and the questions that are asked to elicit responses corresponding to these risk scores. As shown, responses corresponding to higher numbers indicate high risk.

Referring to FIG. 86, a system Risk Statement listing is shown. This listing shows notes in prose form and relates these to rules within particular groups. The listing also shows the date each note was written and the date each was last revised.

Referring to FIGS. 87–92, an Algorithm Listing/Rules Report is shown. The report lists rule numbers and shows the questions associated with each rule. These are the questions that will be asked of the patient in order to apply the rules. At the end of each question is a logic connector linking the question to the following question so that the rule algorithm may be applied.

Referring to FIG. 93, a Short Patient Note Listing is shown. This note listing presents messages regarding conclusions reached as a result of applying the guidelines to the reported data supplied by the patient. The purpose of this listing education of the patient, either for strictly academic reasons or to enable the patient to take preventative measures in the future.

Referring to FIGS. 94 and 95, a Suggestions Listing is shown. This listing presents recommended interventions applicable to a particular patient. These recommended interventions are generated as a result of the guidelines being applied to the reported data.

Preferred and alternate embodiments of the present invention have now been described in detail. It is to be noted, however, that this description of these embodiments is merely illustrative of the principles underlying the inventive concept. It is therefore contemplated that various modifications of the disclosed embodiments will, without departing from the spirit and scope of the invention, be apparent to persons of ordinary skill in the art.

What is claimed is:

1. An expert system data processing means for generating guideline-based information tools, comprising:

A) input means for accepting input data, the input data including reported data, guidelines, and algorithms;

B) memory means, connected to the input means, for storing the input data and for storing a first application program and a second application program;

C) logic means, connected to the memory means, for manipulating the input data and for running the first application program and the second application program, the first application program adapted to accept the reported data and to manipulate the reported data according to the guidelines and the algorithms in order to produce output data; and D) presentation means, connected to the logic means, for presenting output data, the output data including means for eliciting additional reported data;

E) the logic means being adapted to generate the second application program as a result of manipulating the input data through the first application program;

F) the second application program adapted to accept the additional reported data and to manipulate the additional reported data according to the guidelines and the algorithms in order to produce an output report.

2. The expert system data processing means of claim 1, further comprising a second data processing means, the second data processing means comprising:

A) second input means for accepting additional reported data;

B) second memory means, connected to the second input means, for storing the additional reported data and for storing the guidelines, the algorithms, and the second application program;

C) second logic means, connected to the second memory means, for manipulating the additional reported data and for running the second application program, the second application program adapted to accept the additional reported data and to manipulate the additional reported data according to the guidelines and the algorithms in order to produce an output report; and D) second presentation means, connected to the second logic means, for presenting the output report.

3. The expert system data processing means of claim 1, further comprising guideline editing means, for accepting guideline edit input data and modifying the guidelines according to the guideline edit input data.

4. The expert system data processing means of claim 1, further comprising algorithm editing means, for accepting algorithm edit input data and modifying the algorithms according to the algorithm edit input data.

5. A process for generating guideline-based information tools, comprising the steps of:

A) accepting input report data;

B) manipulating the report data in accordance with guidelines using a computer application program;

C) generating a second computer application program as a result of manipulating the report data;

D) eliciting additional report data as a result of manipulating the report data;

E) manipulating the additional report data in accordance with guidelines using the second computer application program;

F) generating an output report; and

G) taking action based on the output report.

6. The process of claim 5, further comprising the step of eliciting the input report data by asking questions of a data subject.

7. The process of claim 6, wherein the input report data are responses to the questions asked of the data subject.

8. The process of claim 7, wherein the step of manipulating the report data includes the step of applying the guidelines to the answers in order to determine a next question.

9. An expert system data processing means for generating guideline-based information tools, comprising:

A) input means for accepting input data, the input data including reported data, guidelines, and algorithms;

B) memory means, connected to the input means, for storing the input data and for storing a first application program and a second application program;

C) logic means, connected to the memory means, for manipulating the input data and for running the first application program and the second application program, the first application program adapted to accept the reported data and to manipulate the reported data according to the guidelines and the algorithms in order to produce output data; and D) presentation means, connected to the logic means, for presenting output data, the output data including means for eliciting additional reported data;

E) the logic means being adapted to generate the second application program as a result of manipulating the input data through the first application program without requiring any intervention from a person skilled in computer programming;

F) the second application program adapted to accept the additional reported data and to manipulate the additional reported data according to the guidelines and the algorithms in order to produce an output report.

* * * * *